(12) United States Patent
Ewaisha et al.

(10) Patent No.: US 11,208,640 B2
(45) Date of Patent: Dec. 28, 2021

(54) MODULATING HUMAN CAS9-SPECIFIC HOST IMMUNE RESPONSE

(71) Applicant: Arizona Board of Regents on behalf of Arizona State University, Scottsdale, AZ (US)

(72) Inventors: Radwa Ewaisha, Tempe, AZ (US); Samira Kiani, Pittsburgh, PA (US); Shayesteh Roshdi Ferdosi, Tempe, AZ (US); Karen Anderson, Scottsdale, AZ (US); Farzaneh Moghadam, Tempe, AZ (US); Sri Krishna, Tempe, AZ (US); Mo Reza Ebrahimkhani, Pittsburgh, PA (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/632,782

(22) PCT Filed: Apr. 27, 2018

(86) PCT No.: PCT/US2018/029937
§ 371 (c)(1),
(2) Date: Jan. 21, 2020

(87) PCT Pub. No.: WO2019/018041
PCT Pub. Date: Jan. 24, 2019

(65) Prior Publication Data
US 2020/0377871 A1 Dec. 3, 2020

Related U.S. Application Data

(60) Provisional application No. 62/556,061, filed on Sep. 8, 2017, provisional application No. 62/535,516, filed on Jul. 21, 2017.

(51) Int. Cl.
*C12N 9/22* (2006.01)
*G01N 33/573* (2006.01)
*A61K 48/00* (2006.01)

(52) U.S. Cl.
CPC .............. *C12N 9/22* (2013.01); *G01N 33/573* (2013.01); *A61K 48/00* (2013.01); *C12N 2310/20* (2017.05); *C12N 2800/80* (2013.01); *G01N 2333/922* (2013.01)

(58) Field of Classification Search
CPC .. C12N 9/22; C12N 2310/20; C12N 2800/80; G01N 33/573; G01N 2333/922; A61K 48/00; C07K 14/70517
See application file for complete search history.

(56) References Cited

U.S. PATENT DOCUMENTS

| 9,857,374 | B2 | 1/2018 | LaBaer |
| 2014/0273226 | A1 | 9/2014 | Wu |
| 2015/0362497 | A1 | 12/2015 | Anderson |
| 2017/0045515 | A1 | 2/2017 | Anderson |
| 2017/0059563 | A1 | 3/2017 | Smith |
| 2017/0176423 | A1 | 6/2017 | Anderson |
| 2017/0177788 | A1 | 6/2017 | Anderson |
| 2017/0205409 | A1 | 7/2017 | Anderson |
| 2017/0363631 | A1 | 12/2017 | LaBaer |
| 2018/0067117 | A1 | 3/2018 | LaBaer |
| 2018/0172681 | A1 | 6/2018 | Katchman |
| 2018/0320230 | A1 | 11/2018 | LaBaer |
| 2019/0290248 | A1 | 9/2019 | Katchman |
| 2019/0302122 | A1 | 10/2019 | Katchman |

FOREIGN PATENT DOCUMENTS

| WO | 2012021887 | A2 | 2/2012 |
| WO | 2014120902 | A1 | 8/2014 |
| WO | 2015148202 | A1 | 10/2015 |
| WO | 2015148216 | A1 | 10/2015 |
| WO | 2015148273 | A2 | 10/2015 |
| WO | 2015167678 | A1 | 11/2015 |
| WO | 2015167678 | A8 | 11/2015 |
| WO | 2015168515 | A1 | 11/2015 |
| WO | 2016089866 | A1 | 6/2016 |
| WO | 2016094558 | A1 | 6/2016 |
| WO | 2016112242 | A1 | 7/2016 |
| WO | 2016195918 | A1 | 12/2016 |
| WO | 2017075141 | A1 | 5/2017 |
| WO | 2017075141 | A8 | 5/2017 |
| WO | 2017081288 | A1 | 5/2017 |
| WO | 2017197238 | A1 | 11/2017 |
| WO | 2018013531 | A1 | 1/2018 |
| WO | 2018013531 | A8 | 1/2018 |
| WO | 2018013579 | A1 | 1/2018 |
| WO | 2019099723 | A2 | 5/2019 |

OTHER PUBLICATIONS

Chew WL et al. A multi-functional AAV-CRISPR Cas9 and its host response. 2016. Nature Methods. 13(10):868-874. (Year: 2016).*
Chew WL et al. A multi-functional AAV-CRISPR Cas9 and its host response. 2016. Nature Methods. Supplemental Materials, p. 1-33 (Year: 2016).*
Tangri S et al. Rationally Engineered Therapeutic Proteins with Reduced Immunogenecity. 2005. Journal of Immunology. 174:3187-3196. (Year: 2005).*
U.S. Appl. No. 16/743,906, filed Jan. 15, 2020, Labaer et al.
U.S. Appl. No. 16/743,906, filed Feb. 7, 2020, Katchman et al.
Robinson, M.D., et al. edgeR: a Bioconductor package for differential expression analysis of digital gene expression data. Bioinformatics 26, 139-140 (2010).

(Continued)

*Primary Examiner* — Paul J Holland
(74) *Attorney, Agent, or Firm* — Quarles & Brady LLP

(57) ABSTRACT

Provided herein are methods and compositions for reducing an undesirable T cell immune response in human patients prior to and/or during gene therapy using CRISPR/Cas9-based genetic modulation.

6 Claims, 19 Drawing Sheets

Specification includes a Sequence Listing.

(56) References Cited

OTHER PUBLICATIONS

Salvat, R.S. et al. Computationally optimized deimmunization libraries yield highly mutated enzymes with low immunogenicity and enhanced activity. Proc Natl Acad Sci U S A 114, E5085-E5093 (2017).
Scallan, C.D. et al. Human immunoglobulin inhibits liver transduction by AAV vectors at low AAV2 neutralizing titers in SCID mice. Blood 107, 1810-1817 (2006).
Tangri, S. et al. Rationally engineered therapeutic proteins with reduced immunogenicity. J Immunol 174, 3187-3196 (2005).
Tenzer, S. et al. Modeling the MHC class I pathway by combining predictions of proteasomal cleavage, TAP transport and MHC class I binding. Cellular and Molecular Life Sciences 62, 1025-1037 (2005).
Thwaite, R., et al. AAVrh.10 immunogenicity in mice and humans. Relevance of antibody cross-reactivity in human gene therapy. Gene Ther 22, 196-201 (2015).
Trapnell, C. et al. Differential gene and transcript expression analysis of RNA-seq experiments with TopHat and Cufflinks. Nature Protocols 7, 562-578 (2012).
Tscharke, DC et al. "From mice to humans-murine intelligence for human CD8+ T cell vaccine design." Expert opinion on biological therapy 5.2 (2005): 263-271.
Vita, R. et al. The immune epitope database (IEDB) 3.0. Nucleic Acids Res 43, D405-412 (2015).
Wang, D. et al. Adenovirus-Mediated Somatic Genome Editing of Pten by CRISPR/Cas9 in Mouse Liver in Spite of Cas9-Specific Immune Responses. Hum Gene Ther 26, 432-442 (2015).
Wang, J. et al. A versatile protein microarray platform enabling antibody profiling against denatured proteins. Proteomics Clin Appl 7, 378-383 (2013).
Wolfl, M. et al. Activation-induced expression of CD 137 permits detection, isolation, and expansion of the full repertoire of CD8+ T cells responding to antigen without requiring knowledge of epitope specificities. Blood 110, 201-210 (2007).
Yeung, V.P. et al. Elimination of an Immunodominant CD4+ T Cell Epitope in Human IFN-β Does Not Result in an In Vivo Response Directed at the Subdominant Epitope. The Journal of Immunology 172, 6658-6665 (2004).
Yin, H. et al. Non-viral vectors for gene-based therapy. Nat Rev Genet 15, 541-555 (2014).
Zetsche, B. et al. Cpf1 is a single RNA-guided endonuclease of a class 2 CRISPR-Cas system. Cell 163, 759-771 (2015).
Zoller, M. J., et al. "Oligonucleotide-directed mutagenesis using M13-derived vectors: an efficient and general procedure for the production of point mutations in any fragment of DNA." Nucleic Acids Research 10.20 (1982): 6487-6500.
Ahi, Y.S., et al. Adenoviral Vector Immunity: Its Implications and circumvention strategies. Current gene therapy 11, 307-320 (2011).
Aldhamen, Y.A. et al, 16—Methods to Mitigate Immune Responses to Adenoviral Vectors A2—Curiel, David T, in Adenoviral Vectors for Gene Therapy (Second Edition). 2016, Academic Press: San Diego, p. 391-422.
Anderson, K.S. et al. HPV16 antibodies as risk factors for oropharyngeal cancer and their association with tumor HPV and smoking status. Oral oncology 51, 662-667 (2015).
Bartel, M., et al. Enhancing the Clinical Potential of AAV Vectors by Capsid Engineering to Evade Pre-Existing Immunity. Front Microbiol 2, 204 (2011).
Belz, G. T., et al. "A previously unrecognized H-2Db-restricted peptide prominent in the primary influenza A virus-specific CD8+ T-cell response is much less apparent following secondary challenge." Journal of virology 74.8 (2000): 3486-3493.
Boutin, S., et al., Prevalence of serum IgG and neutralizing factors against adeno-associated virus (AAV) types 1, 2, 5, 6, 8, and 9 in the healthy population: implications for gene therapy using AAV vectors. Hum Gene Ther, 2010. 21(6): p. 704-12.

Brunetti-Pierri, N. et al, Progress towards liver and lung-directed gene therapy with helper-dependent adenoviral vectors. Curr Gene Ther, 2009. 9(5): p. 329-40.
Cantor, J.R. et al. Therapeutic enzyme deimmunization by combinatorial T-cell epitope removal using neutral drift. Proc Natl Acad Sci U S A 108, 1272-1277 (2011).
Carapetis, J.R., et al., The global burden of group A streptococcal diseases. Lancet Infect Dis, 2005. 5(11): p. 385-94.
Carter, P., et al. "Improved oligonudeotide site-directed rautagenesis using M13 vectors." Nucleic Acids Research 13.12 (1985): 4431-4443.
Cavazzana-Calvo, M. et al. Gene therapy of human severe combined immunodeficiency (SCID)-X1 disease. Science 288, 669-672 (2000).
Chen, W., et al. "Determinant selection of major histocompatibility complex class I-restricted antigenic peptides is explained by class I-peptide affinity and is strongly influenced by nondominant anchor residues." Journal of Experimental Medicine 180.4 (1994): 1471-1483.
Chen, W., et al. "Dissecting the multifactorial causes of immunodominance in class I-restricted T cell responses to viruses." Immunity 12.1 (2000): 83-93.
Chew, W.L. et al. A multifunctional AAV-CRISPR-Cas9 and its host response. Nat Methods 13, 868-874 (2016).
Chowell, D., et al., TCR contact residue hydrophobicity is a hallmark of immunogenic CD8+ T cell epitopes. Proc Natl Acad Sci U S A, 2015. 112(14): p. E1754-62.
Cyranoski, D. Chinese scientists to pioneer first human CRISPR trial. Nature News 535, 476 (2016).
Dobin, A. et al. STAR: ultrafast universal RNA-seq aligner. Bioinformatics 29, 15-21 (2013).
Esvelt, K.M., et al., Orthogonal Cas9 proteins for RNA-guided gene regulation and editing. Nat Methods, 2013. 10(11): p. 1116-21.
Ferdosi, S. R., et al. "Multifunctional CRISPR/Cas9 with engineered immunosilenced human T cell epitopes." bioRxiv (2018): 360198.
Festa, F., et al. "High-throughput cloning and expression library creation for functional proteomics." Proteomics 13.9 (2013): 1381-1399.
Gao, G. et al. Adeno-associated virus-mediated gene transfer to nonhuman primate liver can elicit destructive transgene-specific T cell responses. Hum Gene Ther 20, 930-942 (2009).
Gaspar, H.B., et al., Gene therapy of X-linked severe combined immunodeficiency by use of a pseudotyped gammaretroviral vector. Lancet, 2004. 364(9452): p. 2181-7.
Hacein-Bey-Abina, S., et al., Sustained correction of X-linked severe combined immunodeficiency by ex vivo gene therapy. N Engl J Med, 2002. 346(16): p. 1185-93.
Halbert, C.L., et al., Successful readministration of adeno-associated virus vectors to the mouse lung requires transient immunosuppression during the initial exposure. J Virol, 1998. 72(12): p. 9795-805.
Hirano, H. et al. Structure and Engineering of Francisella novicida Cas9. Cell 164, 950-961 (2016).
Hoof, I. et al. NetMHCpan, a method for MHC class I binding prediction beyond humans. Immunogenetics 61, 1 (2009).
Howe, S.J., et al., Insertional mutagenesis combined with acquired somatic mutations causes leukemogenesis following gene therapy of SCID-X1 patients. J Clin Invest, 2008. 118(9): p. 3143-50.
International Searching Authority, International Search Report and Written Opinion for application PCT/US2018/029937, dated Aug. 31, 2018.
Jiang, H., et al., Effects of transient immunosuppression on adenoassociated, virus-mediated, liver-directed gene transfer in rhesus macaques and implications for human gene therapy. Blood, 2006. 108(10): p. 3321-8.
Jinek, M. et al. Structures of Cas9 endonucleases reveal RNA-mediated conformational activation. Science 343, 1247997 (2014).
Jinek, M., et al. "RNA-programmed genome editing in human cells." elife 2 (2013): e00471.
Kay, M.A. State-of-the-art gene-based therapies: the road ahead. Nat Rev Genet 12, 316-328 (2011).

(56) References Cited

OTHER PUBLICATIONS

King, C. et al. Removing T-cell epitopes with computational protein design. Proc Natl Acad Sci U S A 111, 8577-8582 (2014).
Krishna et al, Vaccine Design: Methods and Protocols: vol. 1: Vaccines for Human Diseases, 779-796 (2016).
Maggi, E., et al, Technological advances in precision medicine and drug development. Expert Rev Precis Med Drug Dev, 2016. 1(3): p. 331-343.
Manno, C.S., et al., Successful transduction of liver in hemophilia by AAV-Factor IX and limitations imposed by the host immune response. Nat Med, 2006. 12(3): p. 342-7.
Marshall, E. Gene Therapy Death Prompts Review of Adenovirus Vector. Science 286, 2244-2245 (1999).
Martino, A.T. et al. Engineered AAV vector minimizes in vivo targeting of transduced hepatocytes by capsid-specific CD8+ T cells. Blood 121, 2224-2233 (2013).
Mays, L.E. et al. The complex and evolving story of T cell activation to AAV vector-encoded transgene products. Mol Ther 19, 16-27 (2011).
Mazor, R. et al. Rational design of low immunogenic anti CD25 recombinant immunotoxin for T cell malignancies by elimination of T cell epitopes in PE38. Cell Immunol 313, 59-66 (2017).
Mingozzi, F. et al. CD8(+) T-cell responses to adeno-associated virus capsid in humans. Nat Med 13, 419-422 (2007).
Mingozzi, F. et al. Immune responses to AAV vectors: overcoming barriers to successful gene therapy. Blood 122, 23-36 (2013).
Mingozzi, F. et al. Overcoming preexisting humoral immunity to AAV using capsid decoys. Sci Transl Med 5, 194ra192 (2013).
Mok, H., et al. Enhancement of the CD8+ T cell response to a subdominant epitope of respiratory syncytial virus by deletion of an immunodominant epitope. Vaccine 26, 4775-4782 (2008).
Moutaftsi, M. et al. A consensus epitope prediction approach identifies the breadth of murine TCD8+-cell responses to vaccinia virus. Nature biotechnology 24, 817 (2006).
Nathwani, A.C. et al. Adenovirus-associated virus vector-mediated gene transfer in hemophilia B. N Engl J Med 365, 2357-2365 (2011).
Nayak, S. et al. Progress and prospects: immune responses to viral vectors. Gene Ther 17, 295-304 (2010).
Rammensee, H.-G., et al. SYFPEITHI: database for MHC ligands and peptide motifs. Immunogenetics 50, 213-219 (1999).
Ran, F.A. et al. In vivo genome editing using *Staphylococcus aureus* Cas9. Nature 520, 186-191 (2015).
Reardon, S. First CRISPR clinical trial gets green light from US panel. Nature (2016).

\* cited by examiner

FIG. 7C

| Peptide Code (Position) | Peptide Sequence | | Peptide Code (Position) | Peptide Sequence | |
|---|---|---|---|---|---|
| α (240-248) | NLIALSLGL | SEQ ID NO:27 | β (615-623) | ILEDIVLTL | SEQ ID NO:28 |
| α2 | NGIALSLGL | SEQ ID NO:77 | β2 | IGEDIVLTL | SEQ ID NO:80 |
| α9 | NLIALSLGG | SEQ ID NO:78 | β9 | ILEDIVLTG | SEQ ID NO:81 |
| α29 | NGIALSLGG | SEQ ID NO:79 | β29 | IGEDIVLTG | SEQ ID NO:82 |

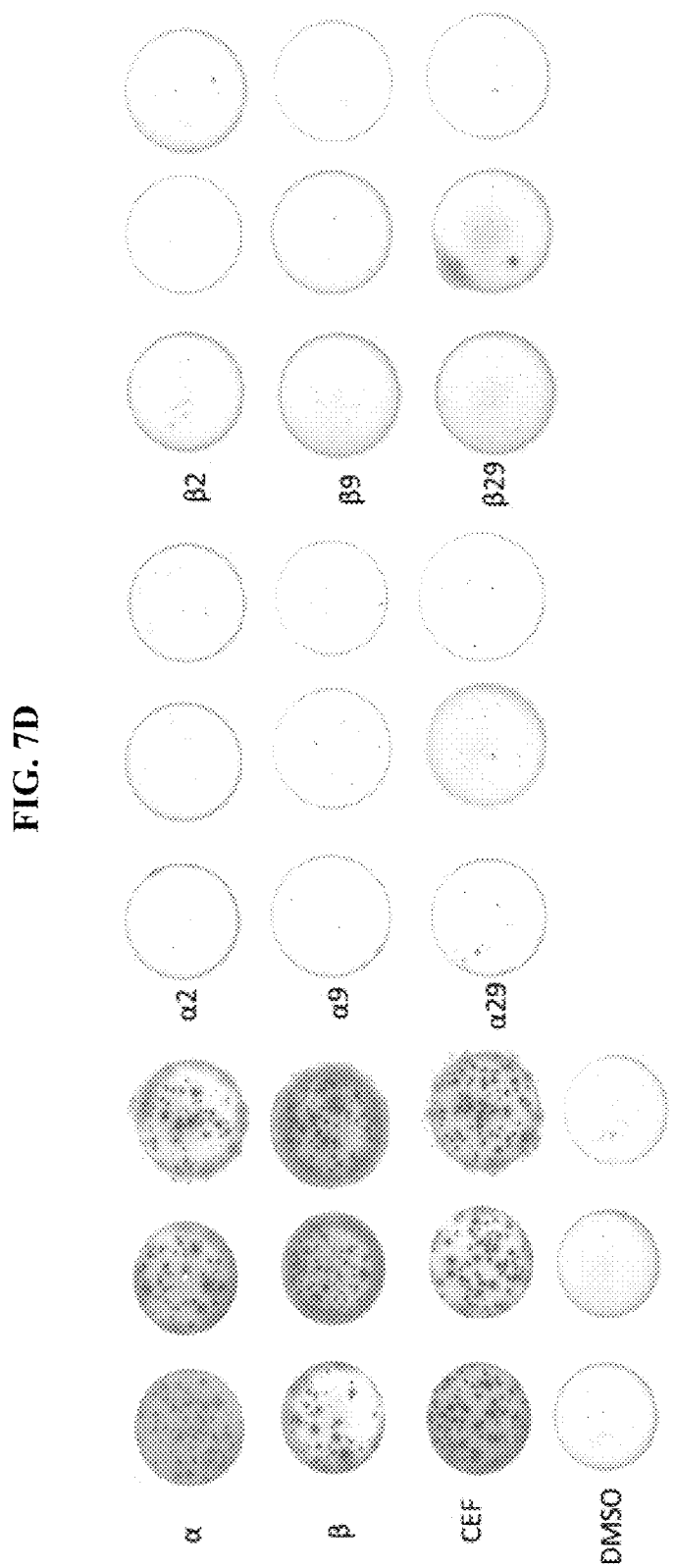

MDKKYSIGLDIGTNSVGWAVITDEYKVPSKKFKVLGNTDRHSIKKNLIGALLFDSGETAEATRL
KRTARRRYTRKNRICYLQEIFSNEMAKVDDSFFHRLEESFLVEEDKKHERHPIFGNIVDEVA
YHEKYPTIYHLRKKLVDSTDKADLRLIYLALAHMIKFRGHFLIEGDLNPDNSDVDKLFIQLVQTY
NQLFEENPINASGVDAKAILSARLSKSRRLENLIAQLPGEKKNGLFGNLIALSGLTPNFKSNF
DLAEDAKLQLSKDTYDDDLDNLLAQIGDQYADLFLAAKNLSDAILLSDILRVNTEITKAPLSASM
IKRYDEHHQDLTLLKALVRQQLPEKYKEIFFDQSKNGYAGYIDGGASQEEFYKFIKPILEKMDG
TEELLVKLNREDLLRKQRTFDNGSIPHQIHLGELHAILRRQEDFYPFLKDNREKEKILTFRIPY
YVGPLARGNSRFAWMTRKSEETITPWNFEEVDKGASAQSFIERMTNFDKNLPNEKVLPKH
SLLYEYFTVYNELTKVKYVTEGMRKPAFLSGEQKKAIVDLLFKTNRKVTVKQLKEDYFKKIECF
DSVEISGVEDRFNASLGTYHDLLKIIKDKDFLDNEENEDILEDIVLTILFEDREMIEERLKTYAH
LFDDKVMKQLKRRYTGWGRLSPRKLINGRDKQSGKTILDFLKSDGFANRNFMQLIHDDSLT
FKEDIQKAQVSGQGDSLHEHIANLAGSPAIKKGILOTVKVVDELVKVMGRHKPENIVIEMARE
NQTTQKGQKNSRERMKRIEEGIKELGSQILKEHPVENTQLONEKLYLYLONGRDMYVDQEL
DINRLSDYDVDHIVPQSFLKDDSIDNKVLTRSDKNRGKSDNVPSEEVVKKMKNYWRQLLNAK
LITQRKFDNLTKAERGGLSELDKAGFIKRQLVETRQITKHVAQILDSRMNTKYDENDKLIREVK
VITLKSKLVSDFRKDFQFYKVREINNYHHADAYLNAVVGTALIKKYPKLESEFVYGDYKVYDV
RKMIAKSEQEIGKATAKYFFYSNIMNFFKTEITLANGEIRKRPLIETNGETGEIWDKGRDFATV
RKVLSMPQVNIVKKTEVQTGGFSKESILPKRNSDKLIARKKDWDPKKYGGFDSPTVAYSVLV
VAKVEKGKSKKLKSVKELLGITIMERSSFEKNPIDFLEAKGYKEVKKDLIIKLPKYSLFELENGR
KRMLASAGELQKGNELALPSKYVNFLYLASHYEKLKGSPEDNEOKQLFVEQHKHYLDEIIEQI
SEFSKRVILADANLDKVLSAYNKHRDKPREQAENIHLFTLTNLGAPAAFKYFDTTIDRKRYTS
TKEVLDATLIHQSITGLYETRIDLSQLGGD (SEQ ID NO:1)

FIG. 14

ATGGATAAGAAATACTCAATAGGCTTAGATATCGGCACAAATAGCGTCGGATGGGCGGTGATCACTGATGAATATAAG
GTTCCGTCTAAAAAGTTCAAGGTTCTCGGGAAATACAGACCGCCACAGTATCAAAAAAATCTTATAGGGCTCTTTAT
TTGACAGTGGAGAGACAGCGGAAGCGGACTCGTCTCAAACGACAGCTCGTAGAAGTAGTATACACGTCGGAAGAATCGTA
TTTGTTATCTACAGGAGATTTTTCAATGAGATGGCGAAAGTAGATGATAGTTCTTCATCGACTTGAAGAGTCTTTT
TTGGTGGAAGAAGACAAGAAGCATGAACGTCATCCTATTTTGGAAATATAGTAGTGCTTATCATGAGAAA
TATCCAACTATCTATCTCTGCGAAAAAAATTGGTAGATTCTACTGATAAAGCGGATTTGCGCTTAATCTATTGGCCTT
AGCGCATATGATTAAGTTCGTGGTCATTTTTGATTGAGGGAGATTTAAATCCTGATAATAGTGATGTGGACAAACTA
TTTATCCAGTTGGTACAAACCTACAATCAATTATTTGAAGAAAAACCCTATTAACGCAAGTGGAGTAGATGCTAAAGCGA
TTCTTTCTGCACGATTGAGTAAATCAAGACGATTAGAAATCTCATTGCTCAGCTCCCCGGTGAGAAGAAAAATGGCTT
ATTTGGGAATCTCATTGCTTTGTCATTGGGTTTGACCCCTAATTTAAATCAAATTTGATTGGCAGAAGATGCTAAAT
TACAGCTTTCAAAGATACTTACGATGATGATTTAGATATGCTATTTCACTTTCAGATATCCTAAGAGTAAATACTGAAATAACTAAGGCTCCC
TTGGCAGCTAAGCTCAATGATTTATCAGATGCTATTTACTTTCAGATATCCTAAGAGTAAATACTGAAATAACTAAGGCTCCCC
TATCAGCTTCAATGAAACGCTACGATGAACATCATCAAGACTGACTCTTTAAAGCTTAGTTGCGACAACAACT
TCCAGAAAAGTATAAAGAATATCTTTTTGATCAATCAAAAAAACGGATATGCAGGTTATATTGATGGGGGAGCTAGCCA
AGAAGAATTTTATAAATTTATCAAACCAATTTTAGAAAAAAATGGATGGTACTGAGGAATTATTGGTGAAACTAAATCGT
GAAGATTTGCTGCGCAACAAGAAGACTTTTATCCATTTTAAAAGACAATCGTGATGACGAAGATTGAAAAATCTTGACTTTTCGAAT
TTTTGAGAAGACAAGAAGACTTTTATCCATTTTAAAAGACAATCGTGATGACGAAGATTGAAAAATCTTGACTTTTCGAAT
TCCTTATTATGTGGTCCATTGGCCGTGCAATAGGTGCTTCAGCTCATAAAGGTGTCGATAAAGGTGTCGATAAAGGTGTCGATAAAGGTGTCGATAAACTTGATAAAA
CCATGGAATTTGAAGAAGTGTCGATAACTACCAAAACATAGTTGCTTATGAGTATTTACGGTTTATAACGAATTGACAAAGGT
ATCTTCCAAATGAAAAGTACTACCAAAACATAGTTGCTTATGAGTATTTACGGTTTATAACGAATTGACAAAGGT
CAAATATGTTACTGTATTAGGAGGAATAAGCCAGCATTTCTTTCAGGTGAACAATTTCAAAAAATAGAATGTTTTGATAGTGTTGAA
AAAACAAATGAAAAGTAACCGTTAAGCAATTTAAAAGAAGATTATTCAAAAATAATTGCTAAACCTTATTGACCTTATTGAAGATAGGGAGATGAT
ATTTCAGGAGTTGAAGATAGATTTAATGAAGAAATGAAGATATCTCACCTCTTTGATGATAAGGTGATGAAACAGTTAACGCGCCGTTATACTGGT
TGGGGACGTTTGTCTCGAAATCGCAAATTGATTAATGGTATTAGGCGGATAAGCAATCGGCAAAACAATTAGATTTTTTGAAAT
CAGATGGTTTTGCCAATCGCAATTTTATGCAGCTGATCCATGATAGTTTGACATTTAAAGAAGACATTCAAAAGC
ACAAGTGTCTGGACAAGGCGATAGTTTACATGAACATATTGCAAATTGCAAATTGCAAATTTACATGAACATATTAAAAAAGGTATT

FIG. 14 (cont.)

TTACAGACTGTAAAGTTGTTGATGAATTGGTCAAAGTAATGGTGGGCGCATAAGCCAGAAATATCGTTATTGAAATG
GCACGTGAAAATCAGACAACTCAAAGGGCCAGAAAATTCGCGAGAGCGTATGAAACGAATCGAAGAAGTATCAA
AGAATTAGGAAGTCAGATTCTTAAAGAGCATCCTGTTGAAATACTCAATTGCAAATGAAAAGCTCTATCTATTAT
CTCCAAAATGGAAGAGACATGTATGTGGACCAAGAATTAGATATATTAATCGTTTAAGTGATTATGATGTCGATCACATTG
TTCCACAAAGTTTCCTTAAAGACGATTCAATAGACATAAGGTCTTAACGCGTTCTGATAAAAATCGTGGTAAATCGGA
TAACGTTCCAAGTGAAGAAGTAGTCAAAAGATGAAAAACTATTGGAGACAACTTCTAAACGCCAAGTTAATCACTCA
ACGTAAGTTTGATAATTTAACGAAAGCTGAACGTGGAGGTTTGAGTGAACTTGATAAAGCTGGTTTATCAACGCCAA
TTGGTTGAAACTCGCCAAATCACTAAGCATGTGGCACAAATTTGGATAGTCGCATGAATACTAAATACGATGAAAATG
ATAAACTTATTCGAGAGGTTAAAGTGATTACCTTAAAATCTAAATTAGTTTCTGACTTCCGAAAAGATTTCCAATTCTAT
AAAGTACGTGAGATTAACAATTACCATCGCCATGTATCTAAAATGCCGTCGTTGGAACTGCTTTGATTAAGA
AATATCCAAAACTGAATCGGAGTTTGTCTATGGTGATTATAAAGTTTATGATGTTCGTAAAATGATTGCTAAGTCTGA
GCAAGAATAGGCAAAGCAACCGCAAAATATTTCTTTACTCTAGAACTTCTTCAAAACAGAAATTACACTTT
GCAAATGGAGAGATTCGCAAACGCCCTCTAATCGAAACTGGAAACTGGATAAAGGGCG
AGATTTTGCCACAGTGCGCAAAGTATTGTCCATGCCCCAAGTCAATATTGTCAAGAAAACAGAAGTACAGACAGGGCGG
ATTCTCCAAGGAGTCAATTTACCAAAAGAATTCGGACAAGCTTATTGCTCGTAAAAAGACTGGATCCAAAAA
ATATGGTGGTTTTGATAGTCCAAGGGTAGCTTATTCAGGATCACAATTATGGAAAGAAGTTCCTTTGAAAAAATCGATTGACTTTTA
GTTAAAATCCGTTAAAGAGTTACTAGGGATCAAGTTAAAAAGACTTAATCATTAACAAAAGGAAATTACTACCTAAATATAGTCTTTTGAGTTAGAAAAC
GAAGCTAAAGGATAAGGAAGTTAAAAAAGACTTAAAAAGACTTAATCATTACAAAAGGAAATTACTACCTAAATATAGTCTTTTGAGTTAGAAAAC
GGTCGTAAACGGATGCTAGTGCCGGAGAATTGAAGGTAGTCCAGAAGATAACGAAATGAGCTGGCTCTGCCAAGCACAAAACAATTGTTGTGAGAAT
TTTTTATATTGTAGTAGTGCATATAACAAACATAGAGACAAACCAATAGTGAACAAGCAGAAATATTATTCATTTATTT
AGCATAAGCATTATTAGATGAGATTATTGAGCAAATCAGTGAATTTCTAAGCGTTATTTAGCAGATGCCAATTT
AGATAAAGTTCTTAGTGCATATAACAAACATAGAGACAAACCAATAGTGAACAAGCAGAAATATTATTCATTTATTT
ACGTTGACGAATCTTGGAGCTCCCGCTGCTTTAAATATTTGATACAACAATTGATCGTAAACGATATACGTCTACAA
AAGAAGTTTAGATGCCACTCTTATCCATCAATCCATCACTGGTCTTATGAAACACGCATTGATTGAGTCAGCTAGG
AGGTGACTGA (SEQ ID NO:5)

MODULATING HUMAN CAS9-SPECIFIC HOST IMMUNE RESPONSE

CROSS-REFERENCE TO RELATED APPLICATIONS

This application represents the national stage entry of PCT International Application No. PCT/US2018/029937, filed on Apr. 27, 2018, and claims the benefit of U.S. Provisional Application Ser. No. 62/535,516, filed Jul. 21, 2017, and 62/556,061, filed Sep. 8, 2017, each of which is incorporated by reference herein as if set forth in its entirety.

BACKGROUND

The CRISPR/Cas9 gene-editing tool is currently in clinical trials as the excitement about its therapeutic potential is exponentially growing. Being a bacterial protein, Cas9 is likely to trigger cellular and humoral immune reaction in humans, as has been recently demonstrated in naïve mice. The potential consequences of this immune response include neutralization of the gene product; destruction of the cells expressing it leading to loss of therapeutic activity or tissue destruction; memory effect that prevents re-administration; and violent innate inflammatory response.

Cas9-specific T cell activation and proliferation were confirmed in an expanded CD45+ cell population following in vivo expression of Cas9 delivered by an AAV vector or DNA electroporation in mice. These data highlight the need to characterize the immunogenicity of Cas9 in humans as this gene-editing technology is moving to the clinic. Accordingly, there remains a need for strategies for decreasing the immunogenicity of CRISPR/Cas9 system components and improving the safety of CRISPR-based gene therapies for human subjects.

SUMMARY

Provided herein are methods and compositions for decreasing an undesired T cell immune response in human subjects undergoing gene therapy using a CRISPR/Cas9 system.

In a first aspect, provided herein is a method of identifying and treating a subject at risk of having a Cas9 antigen-specific CD8+ T cell immune response. The method can comprise or consist essentially of (a) detecting one or more immunodominant Cas9 epitopes in a biological sample obtained from the subject, wherein the detection of the one or more immunodominant Cas9 epitopes identifies the subject as having pre-existing immunity to Cas9; and (b) treating the subject identified in (a) with CRISPR/Cas9-based gene therapy, wherein treating comprises introducing into a cell from the identified subject an engineered, non-naturally occurring Type II CRISPR-Cas system comprising a multifunctional Cas9 protein and at least one guide RNA that targets and hybridizes to a target sequence of a DNA molecule in a cell, wherein the DNA molecule encodes and the cell expresses at least one gene product, and wherein the Cas9 protein comprises a mutation selected from the group consisting of L241G, L616G, and L241G/L616G with reference to the position numbering of a *Streptococcus pyogenes* Cas9 protein (SEQ ID NO:1), whereby expression of the at least one gene product is altered and a disease associated with the gene product is treated. The introducing step can be performed ex vivo or in vivo.

In another aspect, provided herein is a method of reducing an undesired Cas9-specific CD8+ T cell immune response in a subject who will receive CRISPR/Cas9-based gene therapy. The method can comprise or consist essentially of the method introducing into a cell from a subject identified as having pre-existing immunity to Cas9 an engineered, programmable, non-naturally occurring Type II CRISPR-Cas system comprising a multifunctional Cas9 protein and at least one guide RNA that targets and hybridizes to a target sequence of a DNA molecule in a cell, wherein the DNA molecule encodes and the cell expresses at least one gene product, and wherein the Cas9 protein comprises a mutation selected from the group consisting of L241G, L616G, and L241G/L616G as numbered relative to SEQ ID NO:1, whereby expression of the at least one gene product is altered and whereby a Cas9-specific CD8+ T cell immune response is reduced relative to that produced by a cell comprising a naturally occurring Cas9 or an engineered, programmable, non-naturally occurring Type II CRISPR-Cas system wherein the Cas9 protein does not comprise the mutation. The introducing step can be performed ex vivo or in vivo.

In another aspect, provided herein is a variant Cas9 protein encoded by the amino acid sequence of SEQ ID NO:2, a variant Cas9 protein encoded by the amino acid sequence of SEQ ID NO:3, and a variant Cas9 protein encoded by the amino acid sequence of SEQ ID NO:4.

In a further aspect, provided herein is an isolated polynucleotide encoding a variant Cas9 polypeptide, a vector comprising such a polynucleotide, and a host cell comprising such a vector.

In another aspect, provided herein is a method of making a variant of a Cas9 polypeptide shown in SEQ ID NO:1. The method can comprise or consist essentially of using a polynucleotide mutagenesis procedure to generate a population of mutants of the Cas9 polynucleotide shown in SEQ ID NO:5, wherein the population of mutant Cas9 polynucleotides encodes Cas9 polypeptide variants having at least one amino acid substitution selected from the group consisting of L241G and L616G as numbered relative to SEQ ID NO:1; and expressing a population of Cas9 polypeptide variants encoded by the population of Cas9 polynucleotide mutants; so that a variant of a Cas9 polypeptide shown in SEQ ID NO:1 is made. The method can further comprise screening one or more members of the population of Cas9 polypeptide variants so as to identify a variant that exhibits a decreased immunogenicity as compared to the Cas9 polypeptide shown in SEQ ID NO:1 but retains cleavage and/or binding activity relative to the activity of a Cas9 polypeptide without the at least one amino acid substitution.

In a further aspect, provided herein is a variant Cas9 protein made by the method described above, wherein the variant Cas9 protein is encoded by an amino acid sequence selected from the group consisting of SEQ ID NO:2, SEQ ID NO:3, and SEQ ID NO:4.

BRIEF DESCRIPTION OF THE DRAWINGS

The present invention will be better understood and features, aspects, and advantages other than those set forth above will become apparent when consideration is given to the following detailed description thereof. Such detailed description makes reference to the following drawings, wherein:

FIGS. 7A-7J demonstrate pCas9 immunodominant epitope-specific CD8+ T cell recognition is abolished after anchor residue mutation while the mutated SpCas9 protein retains its function and specificity. (A) Epitope $\beta$-specific CD8+ T cell response detected using $\beta$-specific pentamer in PBMCs stimulated with peptide $\beta$-pulsed antigen presenting cells. (B) The percentage of CD8+$\beta$-pentamer+ T cells was reduced to 0.3% when APCs were pulsed with the mutated peptide $\beta$2. (C) Sequences of epitopes $\alpha$ and $\beta$ before and after mutation of the anchor (2nd and/or 9th) residues. Sb, normalized binding score; Si, normalized immunogenicity score. (D) IFN-$\gamma$ ELISpot assay in triplicate wells comparing T cell reactivity to wild type or mutated epitopes $\alpha$ and $\beta$. These results are representative of 12 donors and two independent replicates. (E) Schematic of the experiment assessing mutagenesis capacity of Cas9-$\beta$2. Cells were transfected with either WT-Cas9, Cas9-$\beta$2, or an empty plasmid as well as 20 nt gRNA targeting FAX-1 locus. 72 hr after the transfection, percent cleavage was assessed by DNA extraction and illumine sequencing. (F) Percentage of indel formation in EMX-1 locus. Each individual dot represents an individual transfection. (G) Schematic of the experiment assessing gRNA binding, DNA targeting and transcriptional modulation with Cas9-$\beta$2. Cells were transfected with either WT-Cas9, Cas9-$\beta$2, or an empty plasmid as well as 14 nt gRNA targeting TTN or MIAT in the presence of MS2-P65-HSF1 (transcriptional modulation). 72 hr after the transfection, mRNA was assessed by qRT-PCR. (H and I) Shown is the mRNA level relative to an untransfected control experiment. Each individual dot represents an individual transfection. (J) Mean expression levels of 24,078 protein coding and non-coding RNA genes for WT-Cas9 and Cas9-$\beta$2 (each in duplicate) are shown. For visualization purposes, the values were transformed to a log 2(CPM+1) scale. MIA T, the gRNA target gene, is highlighted in red, and R denotes Pearson correlation coefficient between two groups.

Figure 1:
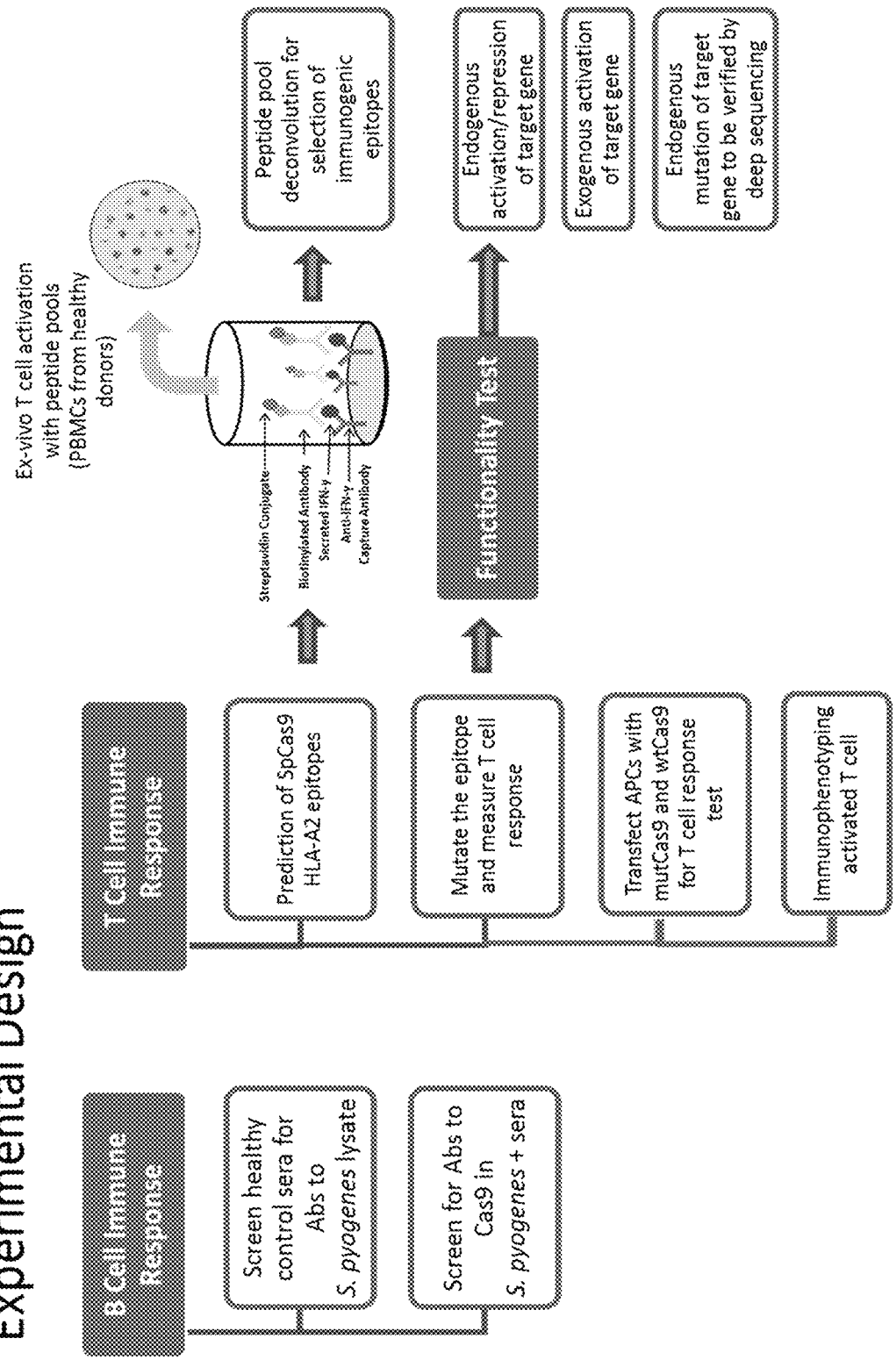
FIG. 1 is a schematic illustrating a workflow for selecting immunogenic epitopes.

shows EYFP expression in cells expressing >2×10² A.U of the transfection marker (BV421). (B) Flow cytometry gating for analysis of Cas9 pentamer+CD8+T lymphocytes. Cells were gated based on FSC and SSC and negatively gated on CD4/CD14/CD19/CD56. The CD8-, CD8+, and Cas9 pentamer+population are shown (bottom right).

Figure 12:
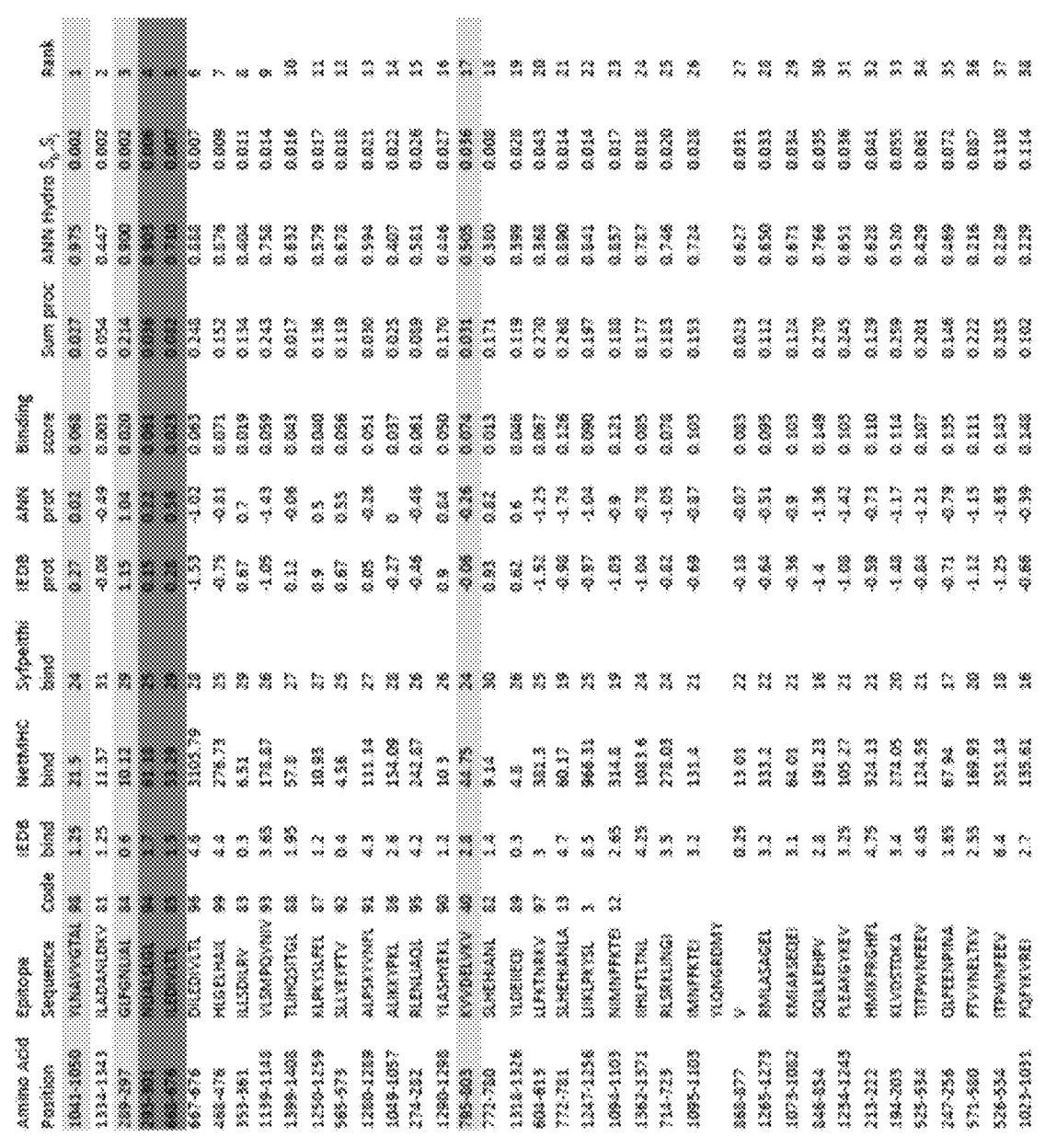

FIG. 12 is a table presenting Cas9 HLA-A*02:01 epitopes (SEQ ID NOs:24-61 for epitopes ranked 1-38, respectively) predicted using the prediction model described herein and ranked according to their $S_i$-$S_b$ score.

FIG. 13 is an amino acid sequence encoding CRISPR-associated endonuclease Cas9/Csn1 of Streptococcus pyogenes (UniProtKB Q99ZW2) (SEQ ID NO:1).

FIG. 14 is a nucleotide sequence encoding CRISPR-associated endonuclease Cas9 of Streptococcus pyogenes (NCBI Reference Sequence: NC_002737.2) (SEQ ID NO:5).

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

Although the following description refers to certain aspects or embodiments, such aspects or embodiments are illustrative and non-exhaustive in nature. Having reviewed the present disclosure, persons of ordinary skill in the art will readily recognize and appreciate that numerous other possible variations or alternative configurations or aspects are possible and were contemplated within the scope of the present disclosure.

Provided herein are compositions, methods, and systems based at least in part on the inventors' identification of immunodominant T cell epitopes of Streptococcus pyogenes Cas9 (SpCas9).

In a first aspect, provided herein is a method of making a genetically modified Cas protein and variant Cas proteins made by such methods. Modifications to a Cas9 protein sequence are made based on immunodominant T cell epitopes of Cas proteins, including wild-type and modified (variant) versions of Cas9. In some embodiments, a Cas9 protein has been genetically modified to remove immunogenically dominant epitopes (also known as "immunodominant epitopes") associated with suboptimal results in clinical gene therapy. As used herein, the term "immunodominant" refers to an epitope capable of stimulating an immune response over other potential epitopes contained within a protein or organism. Deletion or mutation of immunodominant epitopes can potentially decrease the risk of the potentially disruptive immune response in individuals before or during receiving CRISPR/Cas treatment. This method specifically modifies a Cas protein to reduce the risk of the potentially disruptive immune response in individuals (regardless of their HLA type) while preserving its function. In this manner, immunogenic epitopes will be silenced to generate a CRISPR/Cas tool that induces minimal host immune response. As used herein, the term "epitope," also known as an immunogenic epitope or antigenic determinant, refers to the set of amino acid residues that is involved in recognition by a particular immunoglobulin, or in the context of T cells, those residues necessary for recognition by T cell receptor proteins and/or Major Histocompatibility Complex (MHC) receptors. In an immune system setting, in vitro or in vivo, an epitope is the collective features of a molecule, such as primary, secondary and tertiary peptide structure, and charge, that together form a site recognized by an immunoglobulin, T cell receptor, or Human Leukocyte Antigen (HLA) molecule.

Immunodominance is the observation that in spite of a large number of possible epitopes (antigen fragments) in an antigen, the immune system focuses its response on a limited number of epitopes and can be ordered as a reproducible hierarchy (Sercarz et al. 1993). Immunodominance holds true for immune responses to artificial antigens, human viruses including influenza and vaccinia, and intracellular bacteria (Chen W S 1994, Belze G T et al. 2000, Chen W 2000, Tscharke D C 2005). As used herein, the term "dominant antigen" or "dominant epitope" (also referred to herein as an "immunodominant epitope") refers to an antigen or epitope that evokes a strong tolerance or immune response, which may be characterized by the presence of T cells specific for that antigen or epitope in an amount greater than about 70% of the total number of responding T cells. As used herein, the term "subdominant antigen" or "subdominant epitope" refers to an antigen or epitope that evokes a weaker tolerance or immune response than that of a dominant antigen or epitope.

As used herein, the term "immune response" refers to a response of a cell of the immune system, such as a B cell, T cell, or monocyte, to a stimulus. In one embodiment, the response is specific for a particular antigen (an "antigen-specific response"). In one embodiment, an immune response is a T cell response, such as a CD4+ response or a CD8+ response. In another embodiment, the response is a B cell response, and results in the production of specific antibodies.

In some cases, the method of making a mutant multifunctional Cas9 protein (e.g., having DNA binding activity and nuclease activity) or mutant nuclease-null Cas9 protein comprises identifying one or more immunodominant epitopes among full length amino acid sequences of wild-type and/or modified Cas9 proteins, identifying a nucleic acid sequence for the one or more immunodominant epitopes, generating a nucleic acid sequence for a target Cas9 protein which introduces one or more mutations to disrupt the one or more immunodominant epitopes, and generating a mutant Cas9 protein from the generated nucleic acid sequence.

In certain embodiments, the mutations alter one or more amino acid residues in the amino acid sequence of a target Cas protein. In some cases, the mutation replaces a leucine (L) residue at position 241 with a glycine (G), as numbered relative to the position numbering of a Streptococcus pyogenes Cas9 amino acid sequence (SEQ ID NO:1). A Cas9 protein variant comprising L241G is identified herein as Cas9-α2 (SEQ ID NO:2). In other cases, the mutation replaces a leucine (L) residue at position 616 with a glycine (G) as numbered relative to the position numbering of a Streptococcus pyogenes Cas9 protein. A Cas9 protein variant comprising a L241G mutation is identified herein as Cas9-β2 (SEQ ID NO:3). In some cases, mutations are generated at both positions, such that the Cas9 protein variant comprises amino acid substitutions at one or both amino acid positions L241 and L616, as numbered relative to the position numbering of a *Streptococcus pyogenes* Cas9 protein. A Cas9 protein variant comprising L241G and L616G mutations is identified herein as Cas9-α2-β2 (SEQ ID NO:4). Preferably, the Cas9 variant protein retains its wild-type enzymatic activity (e.g., nuclease, nickase, DNA-binding activity). In some cases, the mutant/modified Cas9 protein is encoded by the amino acid sequence of SEQ ID NO:2. In other cases, the mutant/modified Cas9 protein is encoded by the amino acid sequence of SEQ ID NO:3 or SEQ ID NO:4. Preferably, the mutant Cas9 protein retains DNA binding and nuclease activity but is less likely to trigger an adverse immune response in a subject having pre-existing immunity to Cas9.

In some cases, the wild type Cas protein is *Streptococcus pyogenes* Cas9 (SpCas9). In other cases, the wild type Cas protein is a Cas9 ortholog from another bacterial species such as, for example, *Staphylococcus aureus* and *Streptococcus thermophiles*. SpCas9 is the most extensively studied Cas9 protein but other orthologs are being explored to overcome some of the limitations of SpCas9. These include the large size that leaves little space for packaging additional sequences.

Linear immunogenic epitopes of a Cas9 protein, a modified Cas9 protein, or any portion of the Cas protein to be applied in a CRISPR/Cas system are identified using, without limitation, publicly available algorithms (e.g., Immune Epitope Database and Analysis Resource (IEDB)). Predicted peptides are ranked according to their immunogenicity score and will be synthesized to be used to detect the T cell response.

As used herein, the term "CRISPR/Cas" (Clustered Regularly Interspaced Palindromic Repeats/CRISPR associated) refers to a targeted genome editing system that harnesses sequence-specific nuclease activity of a Cas protein. CRISPR systems belong to different classes, with different repeat patterns, sets of genes, and species ranges.

Immunodominant epitopes can be identified and silenced to generate a CRISPR/Cas tool that induces minimal host immune response. In some cases, identified epitopes are modified by mutation or deletion of the necessary amino acids to abolish MHC binding, or by mutation or deletion of the necessary amino acids to abolish TCR contact residues. In some cases, mutagenesis strategies employ the following steps: (a) designing Cas gene fragments containing the desired mutations; (b) designing PCR primers to amplify regions of a Cas gene that do not contain mutations; (c) performing a recombination-based cloning reaction (e.g., Golden Gate or variant thereof) or a BP reaction (i.e., using a BP clonase enzyme) in order to produce different Cas mutants (e.g., three different SpCas9 mutants; single and double mutations); and (d) performing LR reaction (i.e., using a LR clonase enzyme) to clone the mutated Cas gene in a plasmid containing a promoter and Poly A to be able to express the gene. For review of the recombination based cloning systems, see Festa et al., *Proteomics*. 2013; 13(9): 1381-1399.

To assess Cas9 functionality and off-target effects after modification, nuclease activity of genetically modified Cas9 variants is measured. Cells are transfected with Cas9 mutants and gRNA targeting endogenous or exogenous genes, and on-target CRISPR/Cas9 mutations in cultured cells caused by nuclease function of Cas9 are identified using deep sequencing and/or a surveyor nuclease assay. In other cases, Cas9 target recognition and binding function is achieved by transfecting cells with Modified Cas9s and gRNA targeting endogenous or exogenous genes and activation/repression mediators (e.g., SAM, VP64, p65AD, VPR, KRAB) and measuring the expression of genes. In some cases, off-target activity of WT and modified Cas9 proteins are assessed using next generation sequencing.

Due to natural exposure, pre-existing immunity directed against the vector and less commonly the transgene is a common challenge in gene therapy. Being a bacterial protein, SpCas9 is likely to trigger cellular and humoral immune reaction in humans, as was demonstrated in naïve mice. More alarmingly, the ubiquity of *S. pyogenes* with 700 million infections annually, suggests that pre-existing immunity to SpCas9 in healthy individuals is a reasonable concern. Accordingly, in another aspect, this disclosure provides a method for screening human patients to identify patients more likely to have an adverse immune response to gene therapy using a CRISPR/Cas9 system. In this manner, human patients can be classified as good or poor candidates to receive CRISPR/Cas9-based gene therapy based on the likelihood of the subject having an adverse reaction to one or more components of the CRISPR/Cas9 system. For example, candidate patients can be screened for pre-existing immunity to Cas9. In some cases, pre-existing Cas9 immunity is a predictive biomarker of toxicity or adverse response to CRISPR/Cas9-based gene therapy.

Upon identification of a human patient having pre-existing immunity to Cas9, a genetically modified Cas9 having reduced immunogenicity as described herein could be used in place of an unmodified Cas9 for that patient's CRISPR/Cas9-based gene therapy. In some cases, Cas9 immunogenicity in such a patient can also be limited or reduced by co-expressing molecules associated with immune evasion including, but not limited to, PD-LI, CTLA-4, IL-10, IDO-1, antisense HLA class I, and $\beta_2$M.

In order to identify immunogenic epitopes that can potentially be removed or mutated, peripheral blood mononuclear cells (PBMCs) are collected from individuals who have been infected with specific pathogens, individuals with known autoimmune disorders, healthy individuals, etc. and are exposed to (i) Cas9 protein or any specific fragments of it; (ii) a modified Cas9 protein or any specific fragment of a modified Cas9 protein; or (iii) antigen presenting cells (APCs) expressing Cas9, modified Cas9, a fragment of Cas9, a fragment of modified Cas9, or cells targeted with CRISPR/Cas9 system (in any form) expressing Cas9, modified Cas9, a fragment of Cas9, or a fragment of modified Cas9.

As used herein, the term "antigen presenting cells" or "APCs" refers to cells of the immune system used for presenting antigen to T cells. APCs include dendritic cells, monocytes, macrophages, marginal zone Kupffer cells, microglia, Langerhans cells, T cells, and B cells. Preferably, the APCs are an individual's own APCs (meaning, derived or obtained from the individual) that can be briefly cultured and transduced with genetic material (e.g., lentiviral clones) ex vivo. This is a preferred method because it would enable the clinical study of an individual's own T cell repertoire. In some cases, the APCs are an established cell line that acts as an APC and has a human leukocyte antigen (HLA) type that matches the T cells. With established cell lines, it may be possible to maintain a population of cells already programmed with a wide variety of antigens that can be used in repeated experiments. In other cases, the APCs are an established APC cell line that displays a highly common HLA type; an established APC cell line that is programmed to display an HLA type that matches the T cells; an established APC cell line that has been engineered to produce a detectable marker protein (e.g., eGFP, mCherry, luciferase, etc.) upon induction by an activated T cell, an established APC cell line that has been engineered to produce any other detectable signal when induced by an activated T cell; or APCs into which a reporter gene construct is introduced simultaneously with the cDNA. This reporter gene construct would be triggered to signal if the APC is induced to mature after T cell activation.

APCs comprising particular gene constructs can be obtained by cDNA delivery. Preferably, cDNA is introduced into a cell in a form that supports protein expression. The cDNA could be a gene encoding Cas9 from any organism, a library encoding fragments of Cas9 protein that include potentially immunogenic peptides (to map specific epitopes), a gene encoding a modified version of Cas9, or a sequence encoding fragments of Cas9 or Modified Cas9 to investigate which epitope(s) induces a T cell response. cDNA can be introduced into the cells using any appropriate method including, without limitation, lentivirus transduction, retrovirus transduction, other viral delivery systems, electroporation or nucleoporation, delivery of RNA, chemical transfection, or delivery of an exogenous protein or proteins traceable to the library.

To perform the screening method, a population of T cells (e.g., experimentally produced cells or cells from individuals who have been infected with specific pathogens, individuals with known autoimmune disorders, healthy individuals, etc.) is mixed with a portion of Cas9 protein as an antigen. Activated T cells will be measured as an indication of epitope recognition by T cells (effector T cells, cytotoxic T cells, helper T cells, memory T cells, natural killer T cells, or regulatory T cells). T cell activation can be measured using any appropriate method including, without limitation, methods for measuring T cell proliferation (e.g., limiting dilutions culture); cytokine secretion (e.g., ELISPOT, intracellular staining); cytokine capture (e.g. Miltenyi Biotec commercial IFN-γ secretion assay); tetramer (or any MHC-multimer) staining; spectratyping and biosensor assays to detect specific CDR3 of T cell populations of interest; and immunophenotyping of activated T cells (e.g., CD25, CD69, CD137, CD107).

In another aspect, provided herein is a method of identifying and treating a subject at risk of having a Cas9 antigen-specific CD8+ T cell immune response. In some cases, the method comprises (a) detecting one or more immunodominant Cas9 epitopes in a biological sample obtained from the subject, wherein the detection of the one or more immunodominant Cas9 epitopes identifies the subject as having pre-existing immunity to Cas9; (b) treating the subject identified in (a) with CRISPR/Cas9-based gene therapy, wherein treating comprises introducing into a cell from the identified subject an engineered, non-naturally occurring Type II CRISPR-Cas system comprising a multifunctional Cas9 protein and at least one guide RNA that targets and hybridizes to a target sequence of a DNA molecule in a cell, wherein the DNA molecule encodes and the cell expresses at least one gene product, and wherein the Cas9 protein comprises one or more mutations selected from the group consisting of L241G and L616G (including double mutant L241G/L616G) with reference to the position numbering of a *Streptococcus pyogenes* Cas9 protein (SEQ ID NO:1), whereby expression of the at least one gene product is altered and a disease associated with the gene product is treated. Exemplary immunodominant Cas9 epitopes are shown in Table 3. As used herein, the term "identifying" refers to any action or set of actions that allows a clinician to recognize a subject as one who may benefit from the methods and compositions provided herein. Preferably, the identified subject is one who is in need of a tolerogenic antigen-specific (e.g., Cas9-specific) immune response prior to or during CRISPR/Cas-based gene therapy as provided herein.

As used herein, the term "antigen-specific" refers to any immune response that results from the presence of the antigen, or portion thereof, or that generates molecules that specifically recognize or bind the antigen. For example, where the immune response is antigen-specific antibody production, antibodies are produced that specifically bind the antigen. As another example, where the immune response is antigen-specific CD8+ T cell proliferation and/or activity, the proliferation and/or activity can result from recognition of the antigen, or portion thereof, alone or in complex with MHC molecules. In some cases, the antigen-specific immune response is a Cas9-specific immune response.

For the methods provided herein, foreign nucleic acids (i.e., those which are not part of a cell's natural nucleic acid composition) may be introduced into a cell using any method known to those skilled in the art for such introduction. Such methods include transfection, transduction, viral transduction, microinjection, lipofection, nucleofection, nanoparticle bombardment, transformation, conjugation and the like. One of skill in the art will readily understand and adapt such methods using readily identifiable literature sources. As used herein, the term "undesired immune response" refers to any undesired immune response that results from exposure to an antigen, promotes or exacerbates a disease, disorder or condition provided herein (or a symptom thereof), or is symptomatic of a disease, disorder or condition provided herein. Such immune responses generally have a negative impact on a subject's health or is symptomatic of a negative impact on a subject's health. Undesired immune responses include Cas9 antigen-specific CD8+ T cell proliferation and/or activity. Desired immune responses, therefore, include the inhibition in the stimulation or activation of CD8+ T cells, the inhibition of CD8+ T cell proliferation, the inhibition of the production of cytokines by CD8+ T cells, etc. Methods for testing these immune responses are provided herein or are otherwise known to those of ordinary skill in the art.

In another aspect, provided herein is a method of reducing an undesired Cas9-specific CD8+ T cell immune response in a subject who will receive CRISPR/Cas9-based gene therapy. In certain embodiments, the method comprises introducing into a cell from a subject identified as having pre-existing immunity to Cas9 an engineered, programmable, non-naturally occurring Type II CRISPR-Cas system comprising a multifunctional Cas9 protein and at least one guide RNA that targets and hybridizes to a target sequence of a DNA molecule in a cell, wherein the DNA molecule encodes and the cell expresses at least one gene product, and wherein the Cas9 protein comprises one or more amino acid substitutions selected from the group consisting of L241G, L616G, and L241G/L616G as numbered relative to SEQ ID NO:1, whereby expression of the at least one gene product is altered and whereby a Cas9-specific CD8+ T cell immune response is reduced relative to that produced by a cell comprising a naturally occurring Cas9 protein, a synthetic wild-type Cas9 protein, or an engineered non-naturally occurring Type II CRISPR/Cas system wherein the Cas9 protein does not comprise the mutation. The introducing step can be performed ex vivo or in vivo.

In a further aspect, provided herein is a method of generating a variant Cas9 protein, where the Cas9 variant is less immunogenic when expressed in a human cell yet retains its DNA binding/targeting capacity and its capacity for transcriptional activation or repression. For example, a variant Cas9 generated according to a method described herein retains its capacity to modulate transcription of endogenous genes and reporter genes (e.g., TTN, MIAT genes). In certain embodiments, a variant Cas9 protein made by a method provided herein is less immunogenic relative to a non-variant Cas9 protein when expressed in a human cell yet retains its DNA cleavage activity. In some cases, the method comprises using a polynucleotide mutagenesis procedure to generate a population of mutants of the Cas9 polynucleotide shown in SEQ ID NO:5, wherein the population of mutant Cas9 polynucleotides encodes Cas9 polypeptide variants having at least one amino acid substitution selected from the group consisting of L241G and L616G as numbered relative to SEQ ID NO:1; and expressing a population of Cas9 polypeptide variants encoded by the population of Cas9 polynucleotide mutants; so that a variant of a Cas9 polypeptide shown in SEQ ID NO:1 is made.

In some cases, the method further comprises screening members of a population of Cas9 polypeptide variants so as to identify a variant that exhibits a decreased immunogenicity when expressed in a human cell as compared to the Cas9 polypeptide shown in SEQ ID NO:1 but retains cleavage and/or binding activity relative to the activity of a Cas9 polypeptide without the at least one amino acid substitution.

Illustrative methods of mutagenesis protocols are shown, for example, in the following Examples. In addition, a wide variety of techniques for generating variant polynucleotides and polypeptides have been well known in the art for many years, for example site-directed mutagenesis (see, e.g. Carter et al., 1986, *Nucl. Acids Res.* 13:4331; Zoller et al., 1987, *Nucl. Acids Res.* 10:6487), In another aspect, provided herein is a variant Cas9 protein made by a method provided herein. Typically, the substitution variant exhibits one or more altered properties as compared to the Cas9 polypeptide shown in SEQ ID NO:1, for example, a decreased immunogenicity.

Embodiments of this disclosure also include polynucleotides encoding the Cas9 variants disclosed herein, for example an isolated polynucleotide having at least a 90%-100% sequence identity to a polynucleotide encoding a variant Cas9 polypeptide as disclosed herein. In some cases, a polynucleotide encoding a variant Cas9 polypeptide as disclosed herein is in a vector. In some cases, the vector is in a host cell (e.g., a bacterial cell, a human cell, or other eukaryotic cell).

A nucleic acid sequence encoding the desired variant Cas9 polypeptide once isolated or synthesized, can be cloned into any suitable expression vector using convenient restriction sites. Expression vectors usually include an origin of replication, a promoter, a translation initiation site, optionally a signal peptide, a polyadenylation site, and a transcription termination site. These vectors also usually contain an antibiotic marker gene for selection. Suitable expression vectors may be plasmids, cosmids, or viruses including retroviruses. The coding sequence for the polypeptide is placed under the control of an appropriate promoter, control elements and a transcriptional terminator so that the DNA sequence encoding the polypeptide is transcribed into RNA in the host cell transformed by the expression vector construct. The coding sequence may or may not contain a signal peptide or leader sequence for secretion of the polypeptide out of the host cell. Numerous expression vectors and systems are known, both for prokaryotes and eukaryotes, and the selection of an appropriate system is a matter of choice. Expression and purification of the polyprotein product of the invention can be easily performed by one skilled in the art. See, Sambrook et al., "Molecular cloning-A Laboratory Manual, second edition."

The techniques and procedures described or referenced herein are generally well understood and commonly employed using conventional methodology by those skilled in the art, such as, for example, the widely utilized molecular cloning methodologies described in Ausubel et al., Current Protocols in Molecular Biology, Wiley Interscience Publishers, (1995). As appropriate, procedures involving the use of commercially available kits and reagents are generally carried out in accordance with manufacturer defined protocols and/or parameters unless otherwise noted.

So that the methods and compositions provided herein may more readily be understood, certain terms are defined:

As used in this specification and the appended claims, the singular forms "a," "an," and "the" include plural references unless the context clearly dictates otherwise. Any reference to "or" herein is intended to encompass "and/or" unless otherwise stated.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

The terms "nucleic acid" and "nucleic acid molecule," as used herein, refer to a compound comprising a nucleobase and an acidic moiety, e.g., a nucleoside, a nucleotide, or a polymer of nucleotides. Typically, polymeric nucleic acids, e.g., nucleic acid molecules comprising three or more nucleotides are linear molecules, in which adjacent nucleotides are linked to each other via a phosphodiester linkage. In some embodiments, "nucleic acid" refers to individual nucleic acid residues (e.g. nucleotides and/or nucleosides). In some embodiments, "nucleic acid" refers to an oligonucleotide chain comprising three or more individual nucleotide residues. As used herein, the terms "oligonucleotide" and "polynucleotide" can be used interchangeably to refer to a polymer of nucleotides (e.g., a string of at least three nucleotides). In some embodiments, "nucleic acid" encompasses RNA as well as single and/or double-stranded DNA. Nucleic acids may be naturally occurring, for example, in the context of a genome, a transcript, an mRNA, tRNA, rRNA, siRNA, snRNA, a plasmid, cosmid, chromosome, chromatid, or other naturally occurring nucleic acid molecule. On the other hand, a nucleic acid molecule may be a non-naturally occurring molecule, e.g., a recombinant DNA or RNA, an artificial chromosome, an engineered genome, or fragment thereof, or a synthetic DNA, RNA, DNA/RNA hybrid, or include non-naturally occurring nucleotides or nucleosides. Furthermore, the terms "nucleic acid," "DNA," "RNA," and/or similar terms include nucleic acid analogs, i.e. analogs having other than a phosphodiester backbone. Nucleic acids can be purified from natural sources, produced using recombinant expression systems and optionally purified, chemically synthesized, etc. Where appropriate, e.g., in the case of chemically synthesized molecules, nucleic acids can comprise nucleoside analogs such as analogs having chemically modified bases or sugars, and backbone modifications. A nucleic acid sequence is presented in the 5' to 3' direction unless otherwise indicated. In some embodiments, a nucleic acid is or comprises natural nucleosides (e.g. adenosine, thymidine, guanosine, cytidine, uridine, deoxyadenosine, deoxythymidine, deoxyguanosine, and deoxycytidine); nucleoside analogs (e.g., 2-aminoadenosine, 2-thiothymidine, inosine, pyrrolo-pyrimidine, 3-methyl adenosine, 5-methylcytidine, 2-aminoadenosine, C5-bromouridine, C5-fluorouridine, C5-iodouridine, C5-propynyl-uridine, C5-propynyl-cytidine, C5-methylcytidine, 2-aminoadeno sine, 7-deazaadenosine, 7-deazaguanosine, 8-oxoadenosine, 8-oxoguanosine, O(6)-methylguanine, and 2-thiocytidine); chemically modified bases; biologically modified bases (e.g., methylated bases); intercalated bases; modified sugars (e.g., 2'-fluororibose, ribose, 2'-deoxyribose, arabinose, and hexose); and/or modified phosphate groups (e.g., phosphorothioates and 5'-N-phosphoramidite linkages).

The terms "protein," "peptide," and "polypeptide" are used interchangeably herein and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof. A protein may comprise different domains, for example, a nucleic acid binding domain and a nucleic acid cleavage domain. In some embodiments, a protein comprises a proteinaceous part, e.g., an amino acid sequence constituting a nucleic acid binding domain, and an organic compound, e.g., a compound that can act as a nucleic acid cleavage agent.

As used herein, "modifying" ("modify") one or more target nucleic acid sequences refers to changing all or a portion of a (one or more) target nucleic acid sequence and includes the cleavage, introduction (insertion), replacement, and/or deletion (removal) of all or a portion of a target nucleic acid sequence. All or a portion of a target nucleic acid sequence can be completely or partially modified using the methods provided herein. For example, modifying a target nucleic acid sequence includes replacing all or a portion of a target nucleic acid sequence with one or more nucleotides (e.g., an exogenous nucleic acid sequence) or removing or deleting all or a portion (e.g., one or more nucleotides) of a target nucleic acid sequence. Modifying the one or more target nucleic acid sequences also includes introducing or inserting one or more nucleotides (e.g., an exogenous sequence) into (within) one or more target nucleic acid sequences.

A polynucleotide or polypeptide has a certain percent "sequence identity" to another polynucleotide or polypeptide, meaning that, when aligned, that percentage of bases or amino acids are the same, and in the same relative position, when comparing the two sequences. Sequence similarity can be determined in a number of different manners. To determine sequence identity, sequences can be aligned using the methods and computer programs, including alignment algorithms such as BLAST (available on the World Wide Web at ncbi.nlm.nih.gov/BLAST) and FASTA (available in the Genetics Computing Group (GCG) package).

As used herein, a "coding sequence" can be a sequence which "encodes" a particular gene, such as a Cas9 gene, for example. A coding sequence is a nucleic acid sequence which is transcribed (in the case of DNA) and translated (in the case of mRNA) into a polypeptide in vitro or in vivo when placed under the control of appropriate regulatory sequences. The boundaries of the coding sequence are determined by a start codon at the 5' (amino) terminus and a translation stop codon at the 3' (carboxy) terminus. A transcription termination sequence will usually be located 3' to the coding sequence.

As used herein, the term "operably linked" refers to an arrangement of elements wherein the components so described are configured so as to perform their usual function. Thus, control sequences (e.g., promoter sequences, ribosome binding sites, polyadenylation signals, transcription termination sequences, upstream regulatory domains, enhancers, and the like) operably linked to a coding sequence are capable of effecting the expression of the coding sequence. The control sequences need not be contiguous with the coding sequence, so long as they function to direct the expression thereof.

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

The present invention is further illustrated by the following Examples, which in no way should be construed as further limiting. The entire contents of all of the references (including literature references, issued patents, published patent applications, and co-pending patent applications) cited throughout this application are hereby expressly incorporated herein by reference.

EXAMPLES

Presented in this example are experiments demonstrating that immunodominant Cas9 epitopes can be mutated to reduce immunogenicity in human cells without loss of Cas9 DNA binding or nuclease activity.

Materials & Methods

Detection of Cas9-Specific Serum Antibodies in Healthy Controls: Healthy control sera (n=183) used in this study, and previously described (Anderson et al., Oral oncology 51:662-667 (2015)), are a subset of a molecular epidemiology study of head and neck cancer at the MD Anderson Cancer Center, collected between January 2006 and September 2008. S pyogenes lysate was prepared by sonication of bacterial pellets from overnight cultures of S. pyogenes ATCC 19615 in the presence of 1 pill of complete Protease Inhibitor (Sigma-Aldrich) after 3 cycles of freezing and thawing. Serum antibody detection was performed using ELISA. 96-well plates were coated with 20 µg/mL of recombinant S. pyogenes Cas9 nuclease (New England Biolabs, Ipswich, Mass.) or *S. pyogenes* lysate. Sera were diluted 1:50 in 10% *E. coli* lysate prepared in 5% milk-PBST (0.2% tween)(Wang et al., *Proteomics Clin App*7:378-383 (2013)), incubated with shaking for 2 hours at room temperature, and added to the specified wells in duplicate. Horseradish peroxidase (HRP) anti-human IgG Abs (Jackson ImmunoResearch Laboratories, West Grove, Pa.) were added at 1:10,000, and detected using Supersignal ELISA Femto Chemiluminescent substrate (Thermo Fisher Scientific, Waltham, Mass.). Luminescence was detected as relative light units (RLU) on a Glomax 96 Microplate Luminometer (Promega, Madison, Wis.) at 425 nm. To establish cut-off values, a RLU ratio >(the mean +3 standard deviations) of 125 randomly chosen control samples was designated positive (FIG. 2, dotted and dashed lines for bacterial lysate and Cas9 protein, respectively).

Cas9 candidate T cell epitope prediction: Previously described prediction strategies were used to predict candidate Cas9 T cell epitopes. Briefly, we predicted MHC class I restricted 9-mer and 10-mer candidate epitopes derived from the Cas9 protein (Uniprot—Q99ZW2) for HLA A*02: 01. The protein reference sequence was entered into 5 different prediction algorithms; 3 MHC-binding: IEDB-consensus binding (Moutaftsi et al., *Nature biotechnology* 24:817 (2006)), NetMHCpan binding (Hoof et al., *Immunogenetics* 61:1 (2009)), Syfpeithi (Rammensee et al., *Immunogenetics* 50:213-219 (1999)), and 2 antigen-processing algorithms: IEDB consensus processing, ANN processing (Tenzer et al., *Cellular and Molecular Life Sciences* 62, 1025-1037 (2005)). The individual scores from each of the prediction algorithms were then normalized within the pool of predicted peptides after exclusion of poor binders as previously detailed (Chowell et al., *Proc Natl Acad Sci USA* 112:E1754-1762 (2015); Krishna & Anderson, *Vaccine Design: Methods and Protocols: Volume 1: Vaccines for Human Diseases*, 779-796 (2016)), and the average normalized binding scores were used to rerank the candidate peptides. The top 38 candidate peptides (Table 3) were selected for experimental testing. The IEDB consensus MHC-binding prediction algorithm (available at iedb.org on the World Wide Web) was applied to obtain a list of high binding Cas9 peptides, each of which was assigned a normalized binding score (Sb). The immunogenicity score (Si) was calculated for each peptide based on its amino acid hydrophobicity (ANN-Hydro) (Chowell, D. et al., *Proc Natl Acad Sci USA* 112:E1754-1762 (2015)).

Ex vivo stimulation and epitope mapping of Cas9 by ELISpot: All peripheral blood mononuclear cells (PBMCs) were obtained from healthy individuals with written informed consent under ASU's Institutional Review Board. PBMCs were isolated from fresh heparinized blood by Ficoll-Hypaque (GE Healthcare, UK) density gradient centrifugation and stimulated as previously described (Krishna & Anderson, *Vaccine Design: Methods and Protocols: Volume 1: Vaccines for Human Diseases*, 779-796 (2016)). Briefly, predicted Cas9 peptides with Sb<0.148 (N=38) were synthesized (>80% purity) by Proimmune, UK. Each peptide was reconstituted at 1 mg/mL in sterile PBS and pools were created by mixing 3-4 candidate peptides. Sterile multiscreen ELISpot plates (Merck Millipore, Billerica, Mass., USA) were coated overnight with 5 µg/well of anti-IFN-γ capture antibody (clone DIK, Mabtech, USA) diluted in sterile PBS. Frozen PBMCs were thawed rapidly and recombinant human IL-2 (20U/mL, R&D Systems) was added. They were then stimulated in triplicates with 10 µg/mL Cas9 peptide pools (or individual peptides), pre-mixed CEF pool as a positive control (ProImmune, UK), or DMSO as a negative control in the anti-IFN-γ-coated ELISpot plates, (Merck Millipore, Billerica, Mass., USA) and incubated in a 37° C., 5% $CO_2$ incubator for 48 hours. Plates were washed three times for 5 min each with ELISpot buffer (PBS +0.5% FBS) and incubated with 1 µg/mL anti-IFN-γ secondary detection antibody (clone 7-B6-1, Mabtech, USA) for 2 hrs at room temperature, washed and incubated with 1 µg/mL Streptavidin ALP conjugate for 1 hour at room temperature. The wells were washed again with ELISpot buffer and spots were developed by incubating for 8-10 min with detection buffer (33 µL NBT, 16.5 µL BCIP, in 100 mM Tris-HCl pH 9, 1 mM $MgCl_2$, 150 mM NaCl). Plates were left to dry for 2 days and spots were read using the AID ELISpot reader (Autoimmun Diagnostika GmbH, Germany). The average number of spot forming units for each triplicate was calculated for each test peptide or peptide pool and subtracted from the background signal.

Autologous APC generation from healthy individual PBMCs: Autologous CD40L-activated B cell APCs were generated from healthy donors by incubating whole PBMCs with irradiated (32 Gy) K562-cell line expressing human CD40L (KCD40L) at a ratio of 4:1 (800,000 PBMCs to 200,000 irradiated KCD40Ls) in each well. The cells were maintained in B cell media (BCM) consisting of IMDM (Gibco, USA), 10% heat-inactivated human serum (Gemini Bio Products, CA, USA), and Antibiotic-Antimycotic (Anti-Anti, Gibco, USA). BCM was supplemented with 10 ng/mL recombinant human IL-4 (R&D Systems, MN, USA), 2 µg/mL Cyclosporin A (Sigma-Aldrich, CA, USA), and insulin transferrin supplement (ITES, Lonza, Md., USA). APCs were re-stimulated with fresh irradiated KCD40Ls on days 5 and 10, after washing with PBS and expanding into a whole 24-well plate. After two weeks, APC purity was assessed by CD19+CD86+ expressing cells using flow cytometry, and were used for T cell stimulation after >90% purity. APCs were either restimulated up to 4 weeks or cryopreserved for re-expansion as necessary.

T cell stimulation by autologous APCs: Antigen-specific T cells were generated by stimulating healthy donor B cell APCs by peptide pulsing of specific Cas9 epitopes. Peptide pulsing of APCs was done under BCM 5% human serum, with recombinant IL-4. Twenty-four hours later, on day 1, APCs were washed and incubated with thawed whole PBMCs at a ratio of 1:2 (200,000 APCs: 400,000 PBMCs) in a 24-well plate in BCM supplemented with 20U/mL recombinant human IL-2 (R&D Systems, MN, USA) and 5 ng/mL IL-7 (R&D Systems, MN, USA). On day 5, partial media exchange was performed by replacing half the well with fresh BCM and IL-2. On day 10, fresh APCs were peptide pulsed in a new 24-well plate. On day 11, expanded T cells were restimulated with peptide-pulsed APCs similar to day 1. T cells were used for T cell assays or immunophenotyped after day 18.

Flow cytometry staining for T cells: Cells were washed once in MACS buffer (containing PBS, 1% BSA, 0.5 mM EDTA), centrifuged at 550 g for 5 min and re-suspended in 200 µL MACS buffer. Cells were stained in 100 µL of staining buffer containing anti-CD137, conjugated with phycoerythrin (PE, clone 4B4-1; BD Biosciences, USA), anti-CD8-PC5 (clone B9.11; Beckman Coulter 1:100), anti-CD4 (clone SK3; BioLegend, 1:200), anti-CD14 (clone 63D3; BioLegend, 1:200), and anti-CD19 (clone HIB19; BioLegend, 1:200), all conjugated to Fluorescein isothiocyanate (FITC) for exclusion gates, for 30 min on ice. Samples were covered and incubated for 30 min on ice, washed twice in PBS, and resuspended in 1 mL PBS prior to analysis. Measurements were performed using an Attune Acoustic Focusing Cytometer. Lymphocytes were first identified by forward (FSC) and side scatter (SSC) gating. CD4/CD14/CD19/CD56-negative cells (bin gate) were selected, and activated Pentamer+(or CD137+) T cells were identified within the CD8+ gate. Analysis was performed using Attune Cytometric Software V2.1.

Pentamer staining for T cell immunophenotyping: The following HLA-A*02:01 PE-conjugated Cas9 pentamers were obtained from ProImmune: F2A-D-CUS-A*02:01-ILEDIVLTL-Pentamer, F2A-D-CUS-A*02:01-NLIA-LSLGL-Pentamer, 007—Influenza A MP 58-66-GILGFVFTL-Pentamer. T cells were washed twice in MACS buffer with 5% human serum and centrifuged at 550 g for 5 min each time. They were then re-suspended in 100 μL staining buffer (MACS buffer, with 5% human serum and 1 mM Dasatanib (ThermoFisher Scientific, MA, USA). Each of the pentamers was added to resuspended T cells, stimulated with the respective peptide or APCs at a concentration of 1:100. Samples were incubated at room temperature for 30 min in the dark, then washed twice in MACS buffer. Cells were stained in 100 μL MACS buffer with anti-CD8-PC5, anti-CD4-FITC, anti-CD14-FITC, and anti-CD19-FITC for exclusion gates, Samples were then washed twice with PBS and analyzed by flow cytometry. For flow cytometric analysis, all samples were acquired with Attune flow cytometer (ThermoFisher Scientific, MA, USA) and analyzed using the Attune software. Gates for expression of different markers and pentamers were determined based on flow minus one (FMO) samples for each color after doublet discrimination. Percentages from each of the gated populations were used for the analysis.

Vector Design and Construction:

Modified Cas9 plasmids—Human codon-optimized *Streptococcus pyogenes* Cas9 sequence was amplified from pSpCas9 (pX330; Addgene plasmid ID: 42230), using forward and reverse primers and inserted within gateway entry vectors using golden gate reaction. Desired mutations were designed within gBlocks (Integrated DNA Technologies). The gblocks and amplicons were then cloned into entry vectors using golden gate reaction. All the primers and gblocks sequences are listed in supplementary notes. Next, the Cas9 vectors and CAG promoter cassettes were cloned into an appropriate gateway destination vector via LR reaction (Invitrogen).

U6-sgRNA-MS2 plasmids—These plasmids were constructed by inserting either 14-bp or 20-bp spacers of gRNAs into sgRNA (MS2) cloning backbone (Addgene plasmid ID: 61424) at BbsI site. gRNA sequences are listed in Table 1.

TABLE 1

Sequences of gRNAs

| | |
|---|---|
| MIAT-14bp gRNA | GAGGCTGAGCGCAC (SEQ ID NO: 9) |
| TTN-14bp gRNA | GGAAGTCTCCTTTG (SEQ ID NO: 10) |
| Reporter2-20bp gRNA | GTCCCCTCCACCCCACAGTG (SEQ ID NO: 11) |
| CR10-14bp-gRNA | GCATCAGGAACATGT (SEQ ID NO: 12) |
| EMX1-20bp gRNA | CACC GAGTCCGAGCAGAAGAAGAA (SEQ ID NO: 13) |

Cell culture for endogenous target mutation and activation: HEK293FT cell line was purchased from ATCC and maintained in Dulbecco's modified Eagle's medium (DMEM—Life Technologies) containing 10% fetal bovine serum (FBS—Life Technologies), 2 mM glutamine, 1.0 mM sodium pyruvate (Life Technologies) and 1% penicillinstreptomycin (Life Technologies) in incubators at 37° C. and 5% $CO_2$. Polyethylenimine (PEI) was used to transfect HEK293FT cells seeded into 24-well plates. Transfection complexes were prepared according to manufacturer's instructions.

Figure 11A:
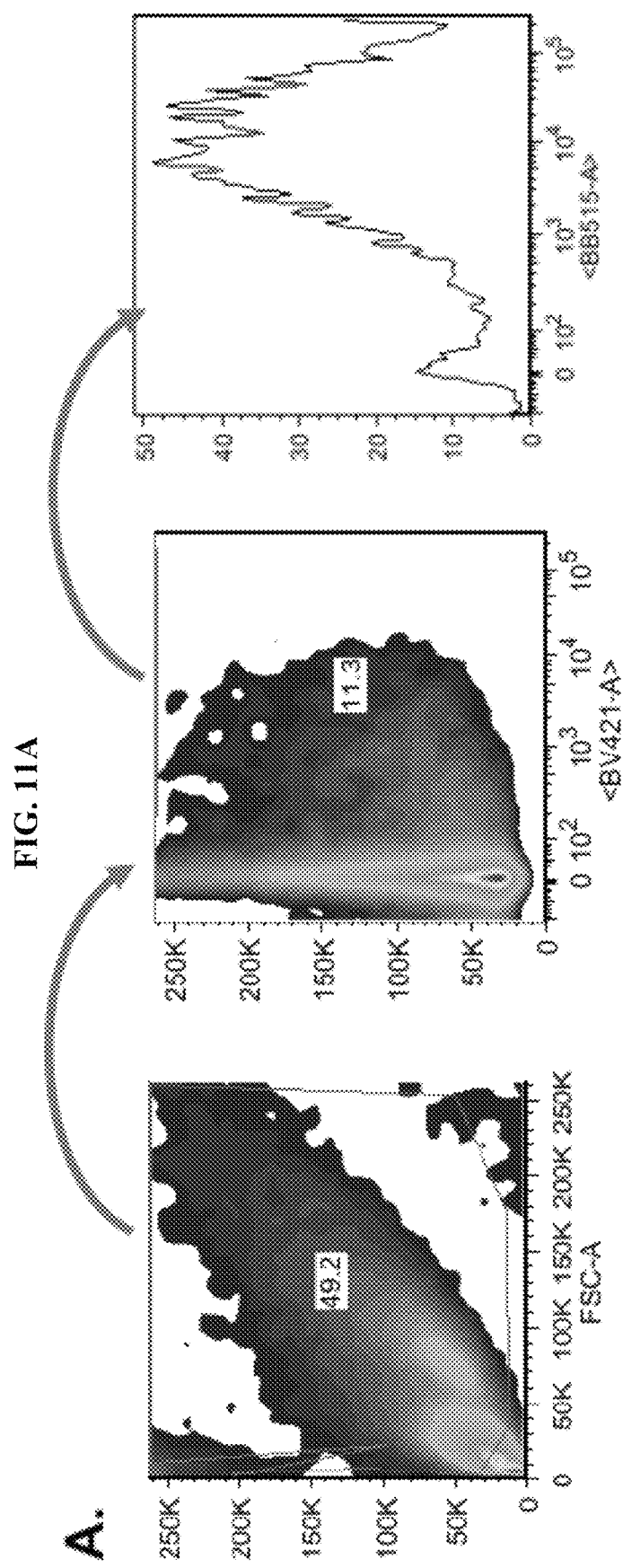
FIGS. 11A-11B. (A) Representative flow cytometry gating for analysis of Cas9 function on synthetic promoters. Cells are gated based on Forward (FSC) and Side Scatter (SSCs). Transfected population then was gated based on expression of EBFP (BV421-A) more than 2×10$^2$. The geometric mean of the output (EYFP) or iRFP was determined in this population. The BB515-A graph (far right)
Figure 11B:
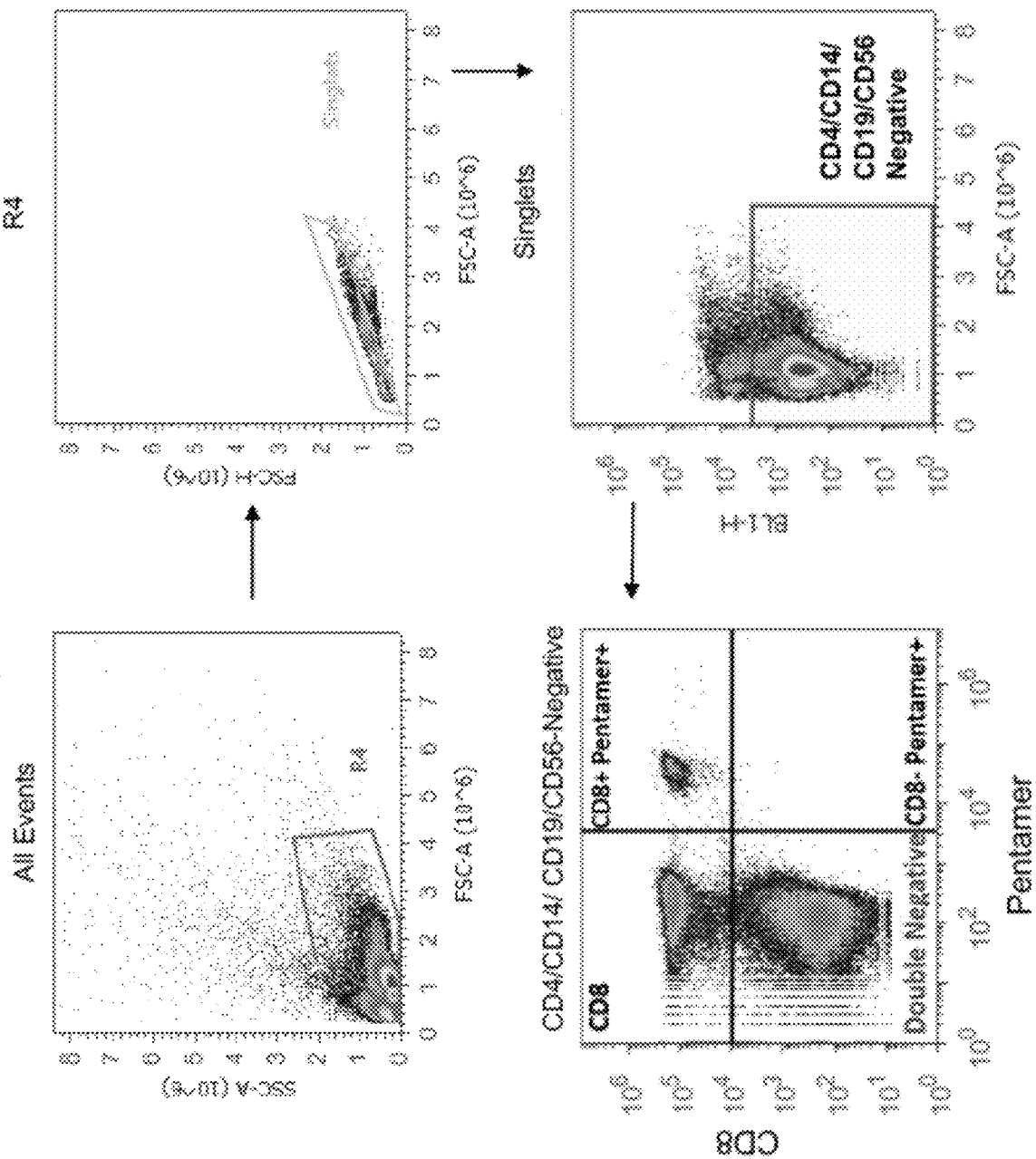

Flow cytometry for Quantifying Cas9 Function: HEK293FT cells were co-transfected with 10 ng gRNA, 200 ng Cas9 constructs, 100 ng reporter plasmid and 25 ng EBFP2 expressing plasmid as the transfection control. Flow cytometry data were collected 48 h after transfection. Cells were trypsinized and centrifuged at 500 g for 5 min at 4C. The supernatant was then removed, and the cells were resuspended in Hank's Balanced Salt Solution without calcium or magnesium supplemented with 2.5% FBS. BD Celesta was used to obtain flow cytometry measurements in synthetic gene circuits with the following settings: EBFP, measured with a 405 nm laser and a 407/421 filter; EYFP, measured with a 488 nm laser and a 490/515 filter, iRFP, measured with a 640 nm laser and a 50/785 filter. At least 200,000 events were gathered from each sample. Flow cytometry data was analyzed using FlowJo software Briefly, cells expressing more than $>2\times10^2$ A.U of EBFP (transfection marker) were gated after gating the cells based on FSC and SSC (to exclude debris) and the geometric mean of EYFP was calculated. A sample was excluded if there were less than 300 events in the gated population. A representative flow cytometry gating is depicted in FIG. 11B.

Quantitative RT-PCR Analysis: HEK293FT cells were co-transfected with 10 ng gRNA, 200 ng Cas9 constructs, 100 ng MS2-P65-HSF1 (Addgene plasmid ID: 61423) and 25 ng transfection control. Cells were lysed, and RNA was extracted using RNeasy Plus mini kit (Qiagen) 72 hours post transfection, followed by cDNA synthesis using the High-Capacity RNA-to-cDNA Kit (Thermo fisher). qRT-PCR was performed using SYBR Green PCR Master Mix (Thermo fisher) using a QuantStudio 3 by Applied Biosystems. All analyses were normalized to 18s rRNA (ΔCt) and fold-changes were calculated against un-transfected controls (2-ΔΔCt). Primer sequences for qPCR are listed in Table 2.

TABLE 2

Sequences of primers

| | |
|---|---|
| Cas9 fragment1-FW | ttttGGTCTCTAGGTCCACCATGGACTATAAGG ACCACGA (SEQ ID NO: 14) |
| Cas9 fragment1-RV | tttggtctcaGAACAGCTGGTTGTAGGTCTGCA (SEQ ID NO: 15) |
| Cas9 fragment2-FW | ttttGGTCTCTACCAACCGGAAAGTGACCGTGA AG (SEQ ID NO: 16) |
| Cas9 fragment2-RV | ttttGGTCTCAAAGCTTACTTTTTCTTTTTTGC C (SEQ ID NO: 17) |
| qPCRMIAT-FW | TGGCTGGGGTTTGAACCTTT (SEQ ID NO: 18) |
| qPCR-MIAT RV | AGGAAGCTGTTCCAGACTGC (SEQ ID NO: 19) |
| qPCRTTN FW | TGTTGCCACTGGTGCTAAAG (SEQ ID NO: 20) |
| qPCR-TTN-RV | ACAGCAGTCTTCTCCGCTTC (SEQ ID NO: 21) |

TABLE 2-continued

Sequences of primers

| | |
|---|---|
| PCR-EMX1-FW | CCATCCCCTTCTGTGAATGT (SEQ ID NO: 22) |
| PCR-EMX1-RV | GGAGATTGGAGACACGGAGA (SEQ ID NO: 23) |

Endogenous Indel Analysis: HEK293FT cells were co-transfected with 200 ng of Cas9 plasmids, 10 ng of gRNA coding cassette and 25 ng transfection control. 72 hours later, transfected cells were dissociated and spun down at 200 g for 5 minutes at room temperature. Genomic DNA was extracted using 50 µl of QuickExtract DNA extraction solution (Epicentre) according to the manufacturer's instructions. Genomic DNA was amplified by PCR using primers flanking the targeted region. Illumina Tru-Seq library was created by ligating partial adaptors and a unique barcode to the DNA samples. Next, a small number of PCR cycles were performed to complete the partial adaptors. Equal amounts of each sample were then pooled and sequenced on Illumina Tru-Seq platform with 2×150 run parameters, which yielded approximately 80,000 reads per sample. Sequencing was performed using a 2×150 paired-end (PE) configuration by CCIB DNA Core Facility at Massachusetts General Hospital (Cambridge, Mass., USA). The reads were aligned to the target gene reference in *Mus musculus* genome using Geneious software, 9-1-5. To detect the indels (insertions and deletions of nucleic acid sequence at the site of double-strand break), each mutation was evaluated carefully in order to exclude the ones that are caused by sequencing error or any off-target mutation. The variant frequencies (percentage to total) assigned to each read containing indels were summed up. i.e., indel percentage=total number of indel containing reads/total number of reads. The minimum number of analyzed reads per sample was 70,000.

RNA Sequencing for Quantifying Activator Specificity: HEK293FT cells were co-transfected with 10 ng gRNA for MIAT locus, 200 ng Cas9 constructs, 100 ng MS2-P65-HSF1 (Addgene plasmid ID: 61423) and 25 ng transfection control. Total RNA was extracted 72 hours post transfection using RNeasy Plus mini kit (Qiagen) and sent to UCLA TCGB core on dry ice. Ribosomal RNA depletion, and single read library preparation were performed at UCLA core followed by RNA sequencing using NextSeq500. Coverage was 14 million reads per sample. FASTQ files with single-ended 75 bp reads were then aligned to the human GRCh38 reference genome sequence (Ensembl release 90) with STAR 54, and uniquely-mapped read counts (an average of 14.8 million reads per sample) were obtained with Cufflink (Trapnell et al., *Nature Protocols* 7:562-578 (2012)). The read counts for each sample were then normalized for the library size to CPM (counts per million reads) with edgeR (Robinson et al., *Bioinformatics* 26:139-140 (2010)). Custom R scripts were then used to generate plots.

Results

Figure 2:
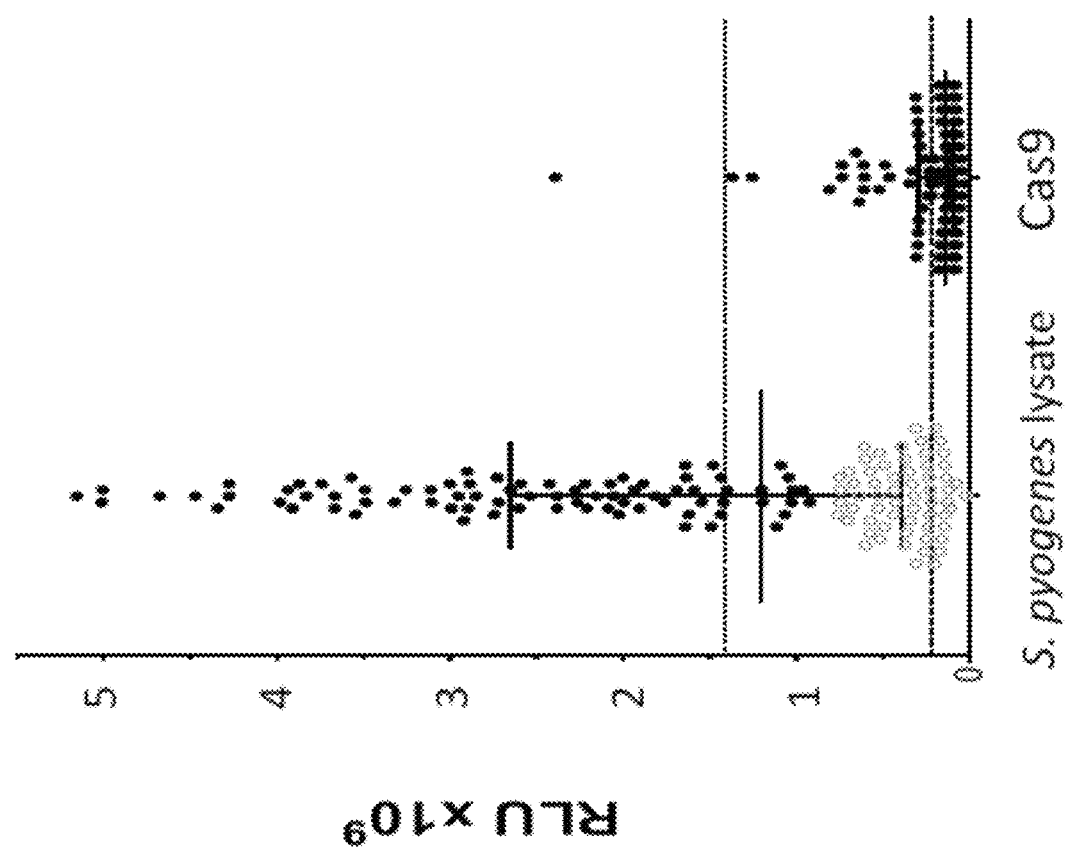
FIG. 2 demonstrates detection of specific serum antibodies (Abs) against *S. pyogenes* lysate in 49.0% (above the dotted line) of 143 healthy controls (left). The subset shown in black circles was screened for Abs against synthetic wild-type Cas9 protein (right), of which 36.6% (21.0% of total samples screened) were positive (above the dashed line). Lines represent median and interquartile range. The mean Relative Light Units (RLU) of positive sera was comparable to the mean RLU detected against the EBNA-1 protein for sera with known EBNA-1 seropositivity.

Detection of Cas9-Specific Serum Antibodies in Healthy Controls: The inventors first investigated whether healthy donors, in particular those with previous exposure to *Streptococcus pyogenes*, have detectable IgG antibodies (Abs) to *Streptococcus pyogenes* Cas9 (SpCas9). Of 143 healthy control sera screened, 49.0/had detectable Abs against *S. pyogenes* lysate as detected using ELISA (FIG. 2). This positive subset (closed circles) along with 12 of the sera negative for *S. pyogenes* lysate that had the highest RLU value were screened for Abs against synthetic wild-type Cas9. At least 21.0% (n=30) of healthy individuals in this study had Cas9-specific Abs (FIG. 2), confirming pre-existing immune response to Cas9.

Figure 3:
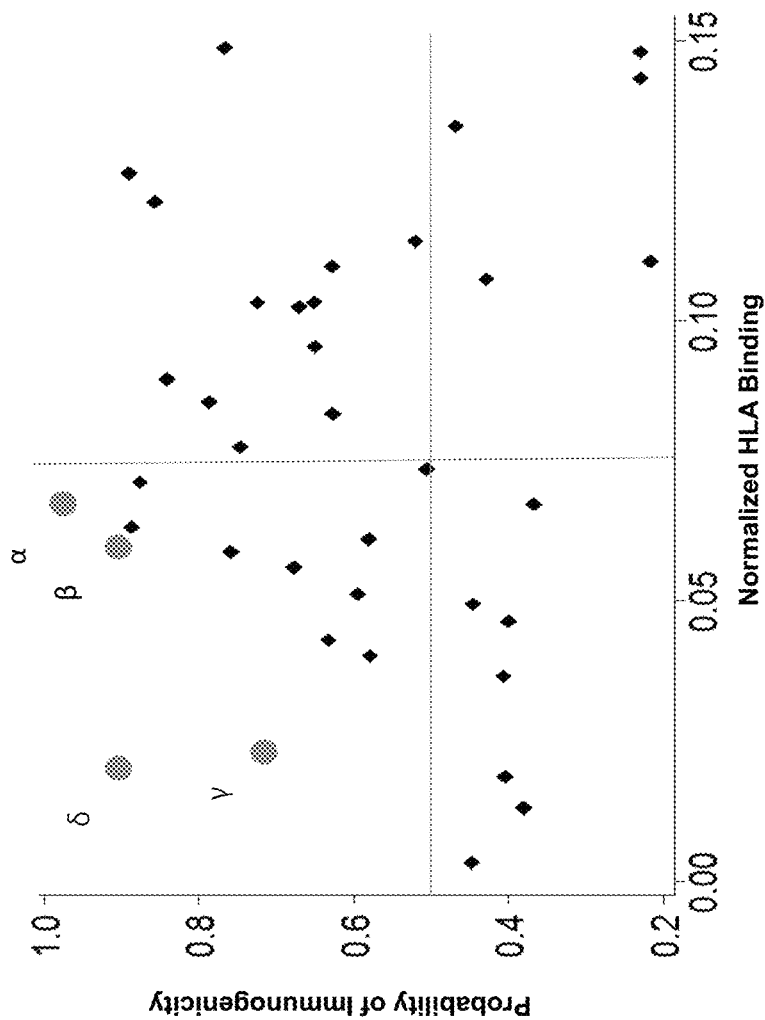
FIG. 3 demonstrates the detection of pre-existing immune response to SpCas9 in healthy donors and identification of two immunodominant T-cell epitopes. The top 5 predicted SpCas9 T cell epitopes and their predicted Sb and Si scores and ranking (based on the Sb.Si value). These top 5 peptides include the identified immunodominant ($\alpha$ and $\beta$; gray) and subdominant ($\gamma$ and $\delta$) epitopes that were shown to be immunogenic by IFN-$\gamma$ ELISpot. The plot shows Sb and Si of predicted HLA-A*02:01 epitopes for the SpCas9 protein. Red dots represent the immunodominant ($\alpha$ and $\beta$) and subdominant ($\gamma$ and $\delta$) epitopes.

Next, HLA-A*02:01-restricted T cell epitopes derived from SpCas9 were predicted using a model based on both HLA binding and biochemical properties of immunogenicity (Table 3; the top 5 are shown in FIG. 3). Using the inventors' previously reported prediction model (Chowell, D., et al., *Proc Nat Acad Sci USA*, 2015. 112(14):E1754-62), based on a MHC class I binding probability and a peptide immunogenicity probability, Cas9 peptides with predicted high binding and high immunogenicity were prioritized. In brief, IEDB consensus MHC-binding prediction algorithm (available at iedb.org on the World Wide Web) was applied to obtain a list of high binding Cas9 peptides for HLA-A*02: 01, each of which was assigned a normalized binding score ($S_b$). Next, an immunogenicity score ($S_i$) was calculated for each peptide based on its amino acid hydrophobicity. According to this prediction model, peptides with low $S_b$ (high binders) and high $S_i$ (more hydrophobic) are expected to be more immunogenic. The calculated normalized binding ($S_b$) and immunogenicity ($S_i$) scores for each peptide (FIG. 3) were plotted to predict the more immunogenic epitopes, which are expected to have both high HLA binding (low $S_b$) and more hydrophobicity (high $S_i$).

TABLE 3

Predicted Cas9 immunogenic T cell epitopes

| Rank | Position | Sequence | SEQ ID NO: | Code | Binding | | | Protein Processing | | $S_b$ | $S_i$ | $S_b \cdot S_i$ |
| | | | | | IEDB | NetMHC | Syfpeithi | IEDB | ANN | | | |
|---|---|---|---|---|---|---|---|---|---|---|---|---|
| 1 | 988-997 | YLNAVVGTAL | 24 | γ | 1.25 | 21.5 | 24 | 0.27 | 0.02 | 0.068 | 0.975 | 0.002 |
| 2 | 1281-1290 | ILADANLDKV | 25 | | 1.25 | 11.37 | 31 | -0.06 | -0.49 | 0.003 | 0.447 | 0.002 |
| 3 | 236-244 | GLFGNLIAL | 26 | δ | 0.6 | 10.12 | 29 | 1.15 | 1.04 | 0.020 | 0.900 | 0.002 |
| 4 | 240-248 | NLIALSLGL | 27 | α | 1.7 | 61.18 | 25 | 0.15 | 0.22 | 0.061 | 0.903 | 0.006 |
| 5 | 615-623 | ILEDIVLTL | 28 | β | 1.5 | 53.29 | 29 | 0.28 | 0.56 | 0.023 | 0.710 | 0.007 |
| 6 | 614-623 | DILEDIVLTL | 29 | | 4.6 | 3105.79 | 28 | -1.53 | -1.02 | 0.063 | 0.888 | 0.007 |
| 7 | 719-727 | SLHEHIANL | 30 | | 1.4 | 9.14 | 30 | 0.93 | 0.82 | 0.013 | 0.380 | 0.008 |
| 8 | 415-423 | HLGELHAIL | 31 | | 4.4 | 276.73 | 25 | -0.75 | -0.81 | 0.071 | 0.876 | 0.009 |
| 9 | 300-308 | ILLSDILRV | 32 | | 0.3 | 6.51 | 29 | 0.67 | 0.7 | 0.019 | 0.404 | 0.011 |
| 10 | 1086-1095 | VLSMPQVNIV | 33 | | 3.65 | 178.87 | 26 | -1.05 | -1.43 | 0.059 | 0.758 | 0.014 |
| 11 | 719-728 | SLHEHIANLA | 34 | | 4.7 | 60.17 | 19 | -0.98 | -1.74 | 0.126 | 0.890 | 0.014 |
| 12 | 1194-1203 | LIKLPKYSL | 35 | | 8.5 | 966.31 | 25 | -0.97 | -1.04 | 0.090 | 0.841 | 0.014 |
| 13 | 1346-1355 | TLIHQSITGL | 36 | | 1.95 | 57.8 | 27 | 0.12 | -0.06 | 0.043 | 0.632 | 0.016 |

TABLE 3-continued

Predicted Cas9 immunogenic T cell epitopes

| Rank | Position | Sequence | SEQ ID NO: | Code | Binding IEDB | NetMHC | Syfpeithi | Protein Processing IEDB | ANN | $S_b$ | $S_i$ | $S_b \cdot S_i$ |
|---|---|---|---|---|---|---|---|---|---|---|---|---|
| 14 | 1197-1207 | KLPKYSLFEL | 37 | | 1.2 | 10.93 | 27 | 0.9 | 0.5 | 0.040 | 0.579 | 0.017 |
| 15 | 1041-1050 | NIMNFFKTEI | 38 | | 2.65 | 314.8 | 19 | −1.03 | −0.9 | 0.121 | 0.857 | 0.017 |
| 16 | 512-520 | SLLYEYFTV | 39 | | 0.4 | 4.56 | 25 | 0.67 | 0.55 | 0.056 | 0.678 | 0.018 |
| 17 | 1309-1318 | IIHLFTLTNL | 40 | | 4.25 | 1083.6 | 24 | −1.04 | −0.78 | 0.085 | 0.787 | 0.018 |
| 18 | 661-670 | RLSRKLINGI | 41 | | 3.5 | 278.03 | 24 | −0.82 | −1.05 | 0.078 | 0.746 | 0.020 |
| 19 | 1227-1236 | ALPSKYVNFL | 42 | | 4.3 | 111.14 | 27 | 0.05 | −0.26 | 0.051 | 0.594 | 0.021 |
| 20 | 996-1004 | ALIKKYPKL | 43 | | 2.6 | 154.09 | 28 | −0.27 | 0 | 0.037 | 0.407 | 0.022 |
| 21 | 221-229 | RLENLIAQL | 44 | | 4.2 | 242.87 | 26 | −0.46 | −0.46 | 0.061 | 0.581 | 0.026 |
| 22 | 1237-1245 | YLASHYEKL | 45 | | 1.2 | 10.3 | 26 | 0.9 | 0.84 | 0.050 | 0.446 | 0.027 |
| 23 | 1265-1273 | YLDEIIEQI | 46 | | 0.3 | 4.8 | 26 | 0.62 | 0.6 | 0.046 | 0.399 | 0.028 |
| 24 | 1042-1050 | IMNFFKTEI | 47 | | 3.2 | 131.4 | 21 | −0.69 | −0.87 | 0.103 | 0.724 | 0.028 |
| 25 | 815-824 | YLQNGRDMYV | 48 | | 0.25 | 13.01 | 22 | −0.18 | −0.07 | 0.083 | 0.627 | 0.031 |
| 26 | 1212-1220 | RMLASAGEL | 49 | | 3.2 | 333.2 | 22 | −0.64 | −0.51 | 0.095 | 0.650 | 0.033 |
| 27 | 1020-1029 | KMIAKSEQEI | 50 | | 3.1 | 64.01 | 21 | −0.36 | −0.9 | 0.103 | 0.671 | 0.034 |
| 28 | 793-801 | SQILKEHPV | 51 | | 2.8 | 191.23 | 16 | −1.4 | −1.36 | 0.149 | 0.766 | 0.035 |
| 29 | 742-750 | KVVDELVKV | 52 | | 2.8 | 44.75 | 24 | −0.06 | −0.26 | 0.074 | 0.505 | 0.036 |
| 30 | 1181-1190 | FLEAKGYKEV | 53 | | 3.25 | 105.27 | 21 | −1.08 | −1.42 | 0.103 | 0.651 | 0.036 |
| 31 | 160-169 | HMIKFRGHFL | 54 | | 4.75 | 324.13 | 21 | −0.59 | −0.73 | 0.110 | 0.628 | 0.041 |
| 32 | 551-559 | LLFKTNRKV | 55 | | 3 | 381.3 | 25 | −1.52 | −1.25 | 0.067 | 0.368 | 0.043 |
| 33 | 141-149 | KLVDSTDKA | 56 | | 3.4 | 274.05 | 20 | −1.48 | −1.17 | 0.114 | 0.520 | 0.055 |
| 34 | 472-481 | TITPVVNFEEV | 57 | | 4.45 | 124.55 | 21 | −0.84 | −1.21 | 0.107 | 0.429 | 0.061 |
| 35 | 194-203 | QLFEENPINA | 58 | | 1.65 | 67.94 | 17 | −0.71 | −0.79 | 0.135 | 0.469 | 0.072 |
| 36 | 518-527 | FTVYNELTKV | 59 | | 2.55 | 169.93 | 20 | −1.12 | −1.15 | 0.111 | 0.216 | 0.087 |
| 37 | 473-481 | ITPWNFEEV | 60 | | 6.4 | 351.14 | 18 | −1.25 | −1.65 | 0.143 | 0.229 | 0.110 |
| 38 | 970-978 | FQFYKVREI | 61 | | 2.7 | 135.61 | 16 | −0.66 | −0.39 | 0.148 | 0.229 | 0.114 |

The table shows Cas9 HLA-A*02:01 epitopes predicted using an integrative prediction model and ranked according to their $S_b \cdot S_i$ score (the lower the more immunogenic). The immunodominant epitopes (α and β) and subdominant epitopes (γ and δ) as confirmed by ELISpot are noted in lines 1 and 3 (bold) and 4-5 (bold and italics) of the above table, respectively.
$S_b$, binding score; $S_i$, immunogenicity score.

Figure 4:
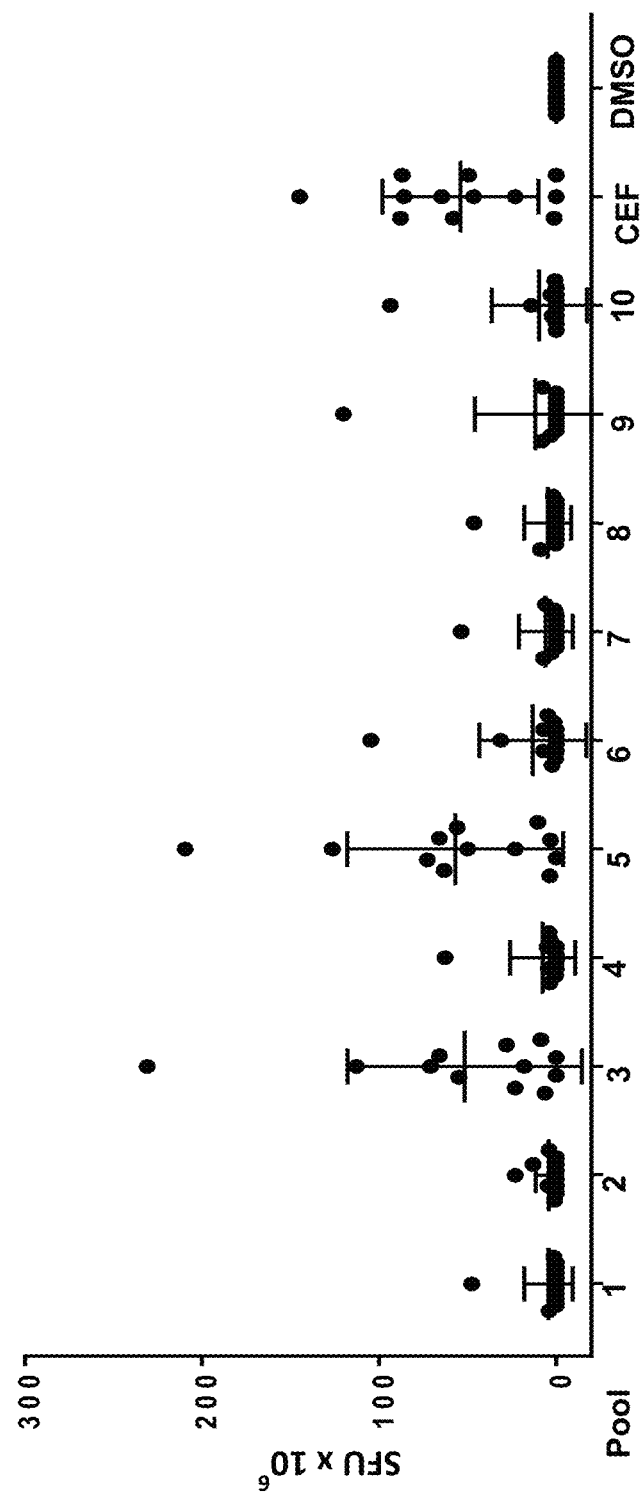
FIG. 4 presents scatter dot plots (median with interquartile range) of IFN-$\gamma$ ELISpot measurements of T cell reactivity of 12 healthy donors to 38 predicted epitopes grouped in 10 pools, CEF (positive control), and DMSO (negative control). Dots represent the means of triplicate wells for each sample and 2 independent replicates.
Figure 5:
FIG. 5 is three-dimensional (3D) representation of the structure of SpCas9 protein, showing the location of the identified immunodominant epitopes $\alpha$ (previously identified as epitope 85) and $\beta$ (previously identified as epitope 94).
Figure 6:
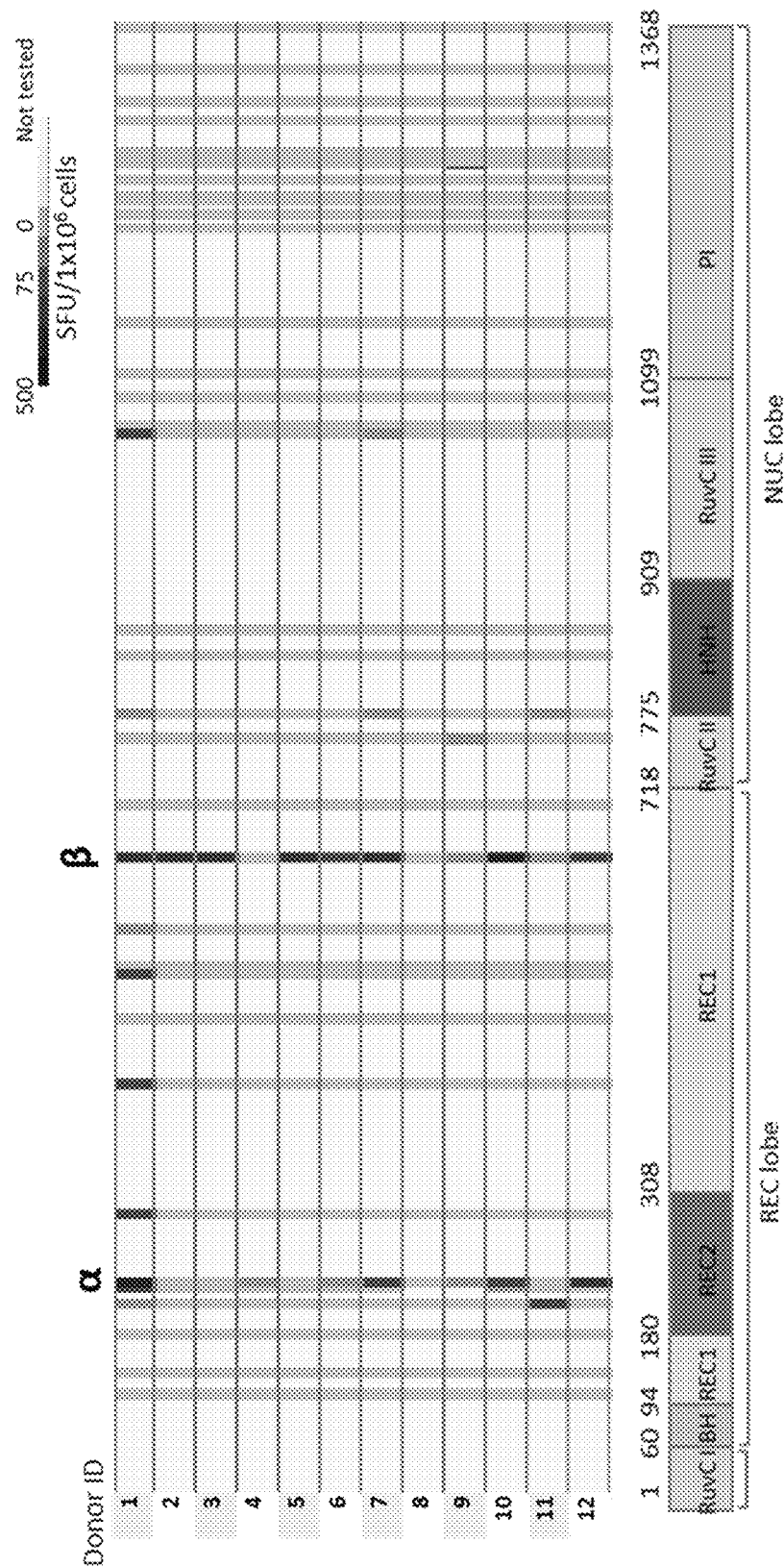
FIG. 6 shows IFN-$\gamma$ ELISpot reactivity of healthy donor T cells (n=12) to epitopes across the different domains of the Cas9 protein. Epitopes $\alpha$ and $\beta$ were the most reactive. Results represent the means of triplicate wells for each sample and 2 independent replicates.

Identification of two Cas9 immunodominant T cell epitopes: To determine whether healthy donor peripheral blood mononuclear cells (PBMCs) had measurable T cell reactivity against predicted Cas9 MHC class I epitopes, the top 38 peptides (Table 1) were synthesized and grouped into 10 pools (each containing 3-4 peptides) for screening memory T cell response in healthy individuals using ELISpot. Peptide-specific T cell immunity was measured using IFN-γ secretion ELISpot assays with PBMCs derived from 12 healthy individuals, and immunoreactive epitopes were identified within pools 3 or 5 in 83.0% of the donors tested (FIG. 4). The seven individual peptides from pools 3 and 5 were evaluated by IFN-γ ELISpot and the dominant immunogenic epitopes were SpCas9_293-301 and SpCas9_668-676, designated peptides α and β, from pools 3 and 5, respectively. The position of peptides α and β within the protein structure is shown in FIG. 5. The individual peptides within pools that were positive for any donor were evaluated for this donor by IFN-γ ELISpot. The immunoreactivity and position of the 38 predicted peptides (a few of which are overlapping) within the Cas9 protein are shown in FIG. 6.

Peptides α and β are shown as red dots on the epitope prediction plot and their sequences and predicted ranking are shown in FIG. 3 and Table 3. As predicted, these peptides had low Sb and high Si values. Both the immunodominant (α and β) and subdominant (γ and δ) T cell epitopes identified by IFN-γ ELISpot were within the top 5 epitopes predicted by our previously described immunogenicity model. Sequence similarity of peptides α (previously identified by inventors as immunodominant epitope 85) and β (previously identified by inventors as immunodominant epitope 94) to amino acid sequences in known proteins was investigated using Protein BLAST and the IEDB epitope database. A peptide was considered 'similar' to α or β if at least 7 of 9 (78%) amino acid residues (that are not the second or ninth) were matching. None of these two peptides resembled known epitopes in the IEDB database, but similarity to other Cas9 orthologs and other bacterial proteins was detected (Tables 4 and 5). Epitope β has sequence similarity to a peptide derived from the *Neisseria meningitidis* peptide chain release factor 2 protein (ILEDIVLTL (SEQ ID NO:28) versus ILEGIVLTL (SEQ ID NO:72)).

TABLE 4

Sequence homology of epitope α to amino acid sequences from known proteins

| | Sequence | Epitope SEQ ID NO: | Similarity (%) | Protein | Sequence ID | Source |
|---|---|---|---|---|---|---|
| 1 | NLIALSLGL | 27 | 9/9 (100%) | type II CRISPR RNA-guided endonuclease Cas9 | WP014612333.1 | *Streptococcus dysgalactiae* |
| 2 | NLIALSLGL | 27 | 9/9 (100%) | type II CRISPR RNA-guided endonuclease Cas9 | WP054279288.1 | *Streptococcus phocae* |
| 3 | NLIALSLGL | 27 | 9/9 (100%) | type II CRISPR RNA-guided endonuclease Cas9 | WP067062573.1 | *Streptococcus pantholopis* |

TABLE 4-continued

Sequence homology of epitope α to amino acid sequences from known proteins

| | Sequence | Epitope SEQ ID NO: | Similarity (%) | Protein | Sequence ID | Source |
|---|---|---|---|---|---|---|
| 4 | NLIALSLGL | 27 | 9/9 (100%) | type II CRISPR RNA-guided endonuclease Cas9 | WP048800889.1 | *Streptococcus constellatus* |
| 5 | NLIALSLGL | 27 | 9/9 (100%) | type II CRISPR RNA-guided endonuclease Cas9 | WP002304487.1 | *Streptococcus mutans* |
| 6 | NLIALSLGL | 27 | 9/9 (100%) | type II CRISPR RNA-guided endonuclease Cas9 | WP049516684.1 | *Streptococcus anginosus* |
| 7 | NLIALSLGL | 27 | 9/9 (100%) | type II CRISPR RNA-guided endonuclease Cas9 | WP003079701.1 | *Streptococcus macacae* |
| 8 | NLIALSLGL | 27 | 9/9 (100%) | type II CRISPR RNA-guided endonuclease Cas9 | GAD40915.1 | *Streptococcus intermedius* SKS4 |
| 9 | NLIAFSLGL | 62 | 8/9 (89%) | Full = RNA polymerase-associated protein RapA; AltName: Full = ATP-dependent helicase HepA | Q6LV34.1 | *Photobacterium profundum* SS9 |
| 10 | NLISLSLGL | 63 | 8/9 (89%) | type II CRISPR RNA-guided endonuclease Cas9 | WP096633625.1 | *Streptococcus parauberis* |
| 11 | NLIALALGL | 64 | 8/9 (89%) | type II CRISPR RNA-guided endonuclease Cas9 | WP075103982.1 | *Streptococcus cuniculi* |
| 12 | NLIALALGL | 64 | 8/9 (89%) | type II CRISPR RNA-guided endonuclease Cas9 | WP058692367.1 | *Streptococcus gallolyticus* |
| 13 | NLIALALGL | 64 | 8/9 (89%) | type II CRISPR RNA-guided endonuclease Cas9 | WP061100419.1 | *Streptococcus pasteurianus* |
| 14 | NLIALALGL | 64 | 8/9 (89%) | type II CRISPR RNA-guided endonuclease Cas9 | WP018363470.1 | *Streptococcus caballi* |
| 15 | NLIALALGL | 64 | 8/9 (89%) | type II CRISPR RNA-guided endonuclease Cas9 | WP099412266.1 | *Streptococcus macedonicus* |
| 16 | NLIALALGL | 64 | 8/9 (89%) | type II CRISPR RNA-guided endonuclease Cas9 | WP014334983.1 | *Streptococcus infantarius* |
| 17 | DLIALYLGL | 65 | 7/9 (78%) | Full = NADH-quinone oxidoreductase subunit N; AltName: Full = NADH dehydrogenase I subunit N; AltName: Full = NDH-1 subunit N | A81421.1 | *Azorhizobium caulinodans* ORS 571 |
| 18 | NLLALALGL | 66 | 7/9 (78%) | type II CRISPR RNA-guided endonuclease Cas9 | WP007896501.1 | *Streptococcus pseudoporcinus* |
| 19 | NLIGLALGL | 67 | 7/9 (78%) | type II CRISPR RNA-guided endonuclease Cas9 | WP061587801.1 | *Streptococcus oralis* |
| 20 | NLVALALGL | 68 | 7/9 (78%) | type II CRISPR RNA-guided endonuclease Cas9 | WP074862269.1 | *Streptococcus equinus* |
| 21 | NLVALVLGL | 69 | 7/9 (78%) | type II CRISPR RNA-guided endonuclease Cas9 | WP020917064.1 | *Streptococcus lutetiensis* |
| 22 | SLIAFSLGL | 70 | 7/9 (78%) | ectoine/hydroxyectoine ABC transporter permease subunit EhuD | WP086160327.1 | *Streptomyces* sp. SCSIO 03032 |
| 23 | YLIALALGL | 71 | 7/9 (78%) | ectoine/hydroxyectoine ABC transporter permease subunit EhuD | WP026413155.1 | *Actinomadura oligospora* |

TABLE 5

Sequence homology of epitope β to amino acid sequences from known proteins

| | Sequence | Epitope SEQ ID NO: | Similarity (%) | Protein | Sequence ID | Source |
|---|---|---|---|---|---|---|
| 1 | ILEDIVLTL | 28 | 9/9 (100%) | type II CRISPR RNA-guided endonuclease Cas9 | WP084916602.1 | *Streptococcus dysgalactiae* |
| 2 | ILEDIVLTL | 28 | 9/9 (100%) | type II CRISPR RNA-guided endonuclease Cas9 | WP074484960.1 | *Streptococcus henryi* |
| 3 | ILEDIVLTL | 28 | 9/9 (100%) | type II CRISPR RNA-guided endonuclease Cas9 | WP003088697.1 | *Streptococcus ratti* |
| 4 | ILEDIVLTL | 28 | 9/9 (100%) | type II CRISPR RNA-guided endonuclease Cas9 | WP044681799.1 | *Streptococcus suis* |

TABLE 5-continued

Sequence homology of epitope β to amino acid sequences from known proteins

| | Sequence | Epitope SEQ ID NO: | Similarity (%) | Protein | Sequence ID | Source |
|---|---|---|---|---|---|---|
| 5 | ILEDIVLTL | 28 | 9/9 (100%) | type II CRISPR RNA-guided endonuclease Cas9 | WP024786433.1 | *Streptococcus mutans* |
| 6 | ILEDIVLTL | 28 | 9/9 (100%) | type II CRISPR RNA-guided endonuclease Cas9 | WP057491067.1 | *Streptococcus orisasini* |
| 7 | ILEDIVLTL | 28 | 9/9 (100%) | type II CRISPR RNA-guided endonuclease Cas9 | WP082312238.1 | *Streptococcus intermedius* |
| 8 | ILEGIVLTL | 72 | 8/9 (89%) | peptide chain release factor 2 | NP275123.1 | *Neisseria meningitidis* MC58 |
| 9 | ILEDIVQTL | 73 | 8/9 (89%) | type II CRISPR RNA-guided endonuclease Cas9 | EAO61901.1 | *Streptococcus agalactiae* |
| 10 | ILEDIVQTL | 73 | 8/9 (89%) | type II CRISPR RNA-guided endonuclease Cas9 | WP070454905.1 | *Streptococcus sp.* HMSC063D10 |
| 11 | VLEDIVLTL | 74 | 8/9 (89%) | type II CRISPR RNA-guided endonuclease Cas9 | WP075346866.1 | *Streptococcus sp.* 'coviae' |
| 12 | VLEDIVLSL | 75 | 7/9 (78%) | type II CRISPR RNA-guided endonuclease Cas9 | WP093650272.1 | *Streptococcus varani* |
| 13 | ILENIV HTL | 76 | 7/9 (78%) | type II CRISPR RNA-guided endonuclease Cas9 | KYF37509.1 | *Streptococcus mitis* |
| 14 | ILENIV HTL | 76 | 7/9 (78%) | type II CRISPR RNA-guided endonuclease Cas9 | WP084972088.1 | *Streptococcus oralis* |
| 15 | ILENIV HTL | 76 | 7/9 (78%) | type II CRISPR RNA-guided endonuclease Cas9 | WP045635197.1 | *Streptococcus gordonii* |

Figure 7A:
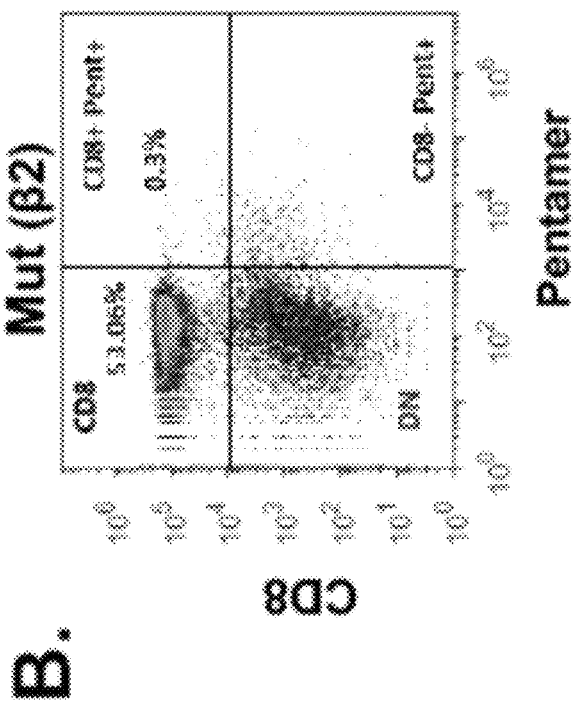

Next, the inventors focused on the immunodominant epitope β. Antigen-specific T cells were expanded for 18 days in vitro by coculturing healthy donor PBMCs with peptide β-pulsed autologous antigen presenting cells (APCs). Cas9-specific CD8+ T cell responses were assessed by flow cytometry. CD8+ T cells specific for the HLA-A*0201/β pentamer were detected after stimulation (3.09%; FIG. 7A).

Figure 7B:
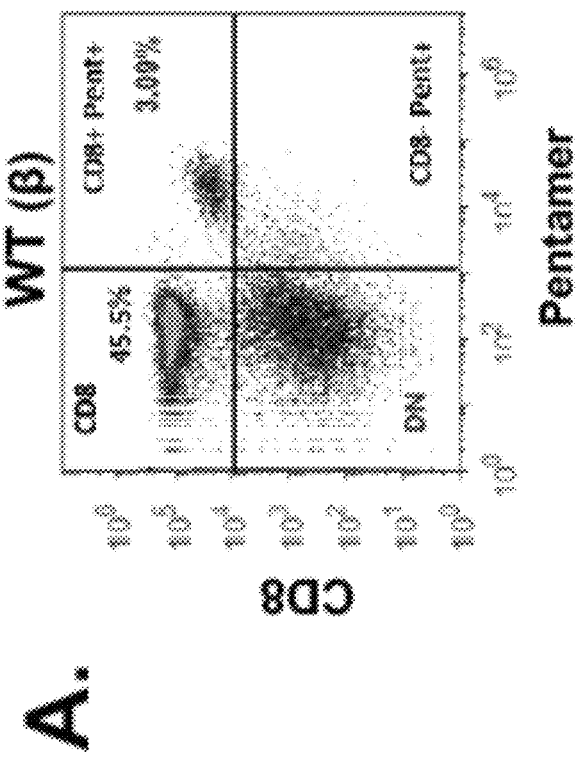
Figure 8:
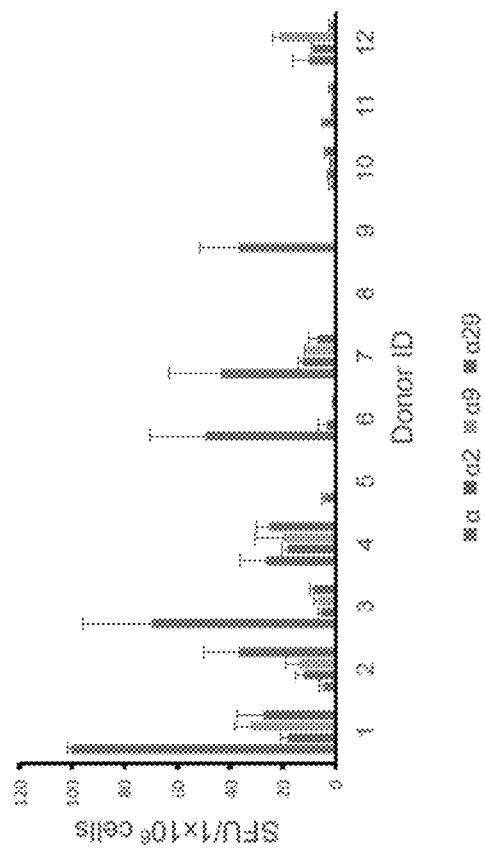
FIGS. 8A-8B demonstrate reduced T cell response to epitopes $\alpha$ and $\beta$ after mutation of the anchor residues. (A and B) IFN-$\gamma$ ELISpot for 12 healthy donor PBMCs stimulated with wild type or mutated peptide $\alpha$ (A) or $\beta$ (B). The average reduction was 8 fold from $\alpha$ to $\alpha$29 and 25 fold from $\beta$ to $\beta$29 (p<0.047). Data represent mean of triplicates and two independent replicates +/–SEM. Two-tailed p value is calculated for paired t tests. A representative ELISPOT image is represented in the FIG. 7D.
Figure 8:
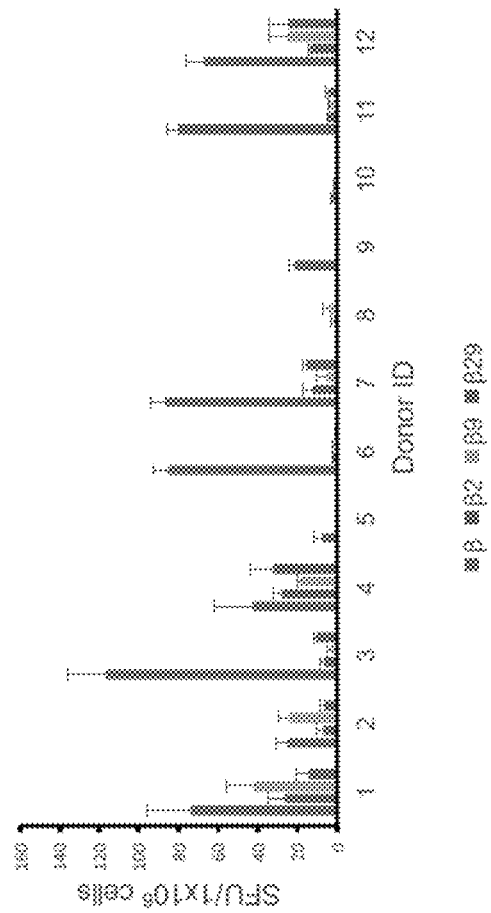

It was hypothesized that mutation of the MHC-binding anchor residues of the identified immunogenic epitopes would abolish specific T cell recognition (FIG. 7A). The epitope anchor residues (2nd and 9th) are not only necessary for peptide binding to the MHC groove, but are also crucial for recognition by the T cell receptor 36. The percentage of CD8+β pentamer+ T cells decreased to 0.3% when APCs were pulsed with the mutated peptide (02; FIG. 7B) compared with 3.09% with the wild type peptide (β; FIG. 7A). The reactivity of healthy donor T cells to modified peptides α or β with mutations in residues 2, 9, or both (sequences are shown in FIG. 7C) was measured using IFN-γ ELISpot assay. The epitope-specific T cell reactivity was markedly reduced with the mutant peptides (FIG. 7D, FIG. 8). The average reduction was 8 fold from α to α29 and 25 fold from β to β29 (n=12; p<0.047; FIG. 8).

Figures 7E, 7F, 7G, 7H, 7I, 7J:
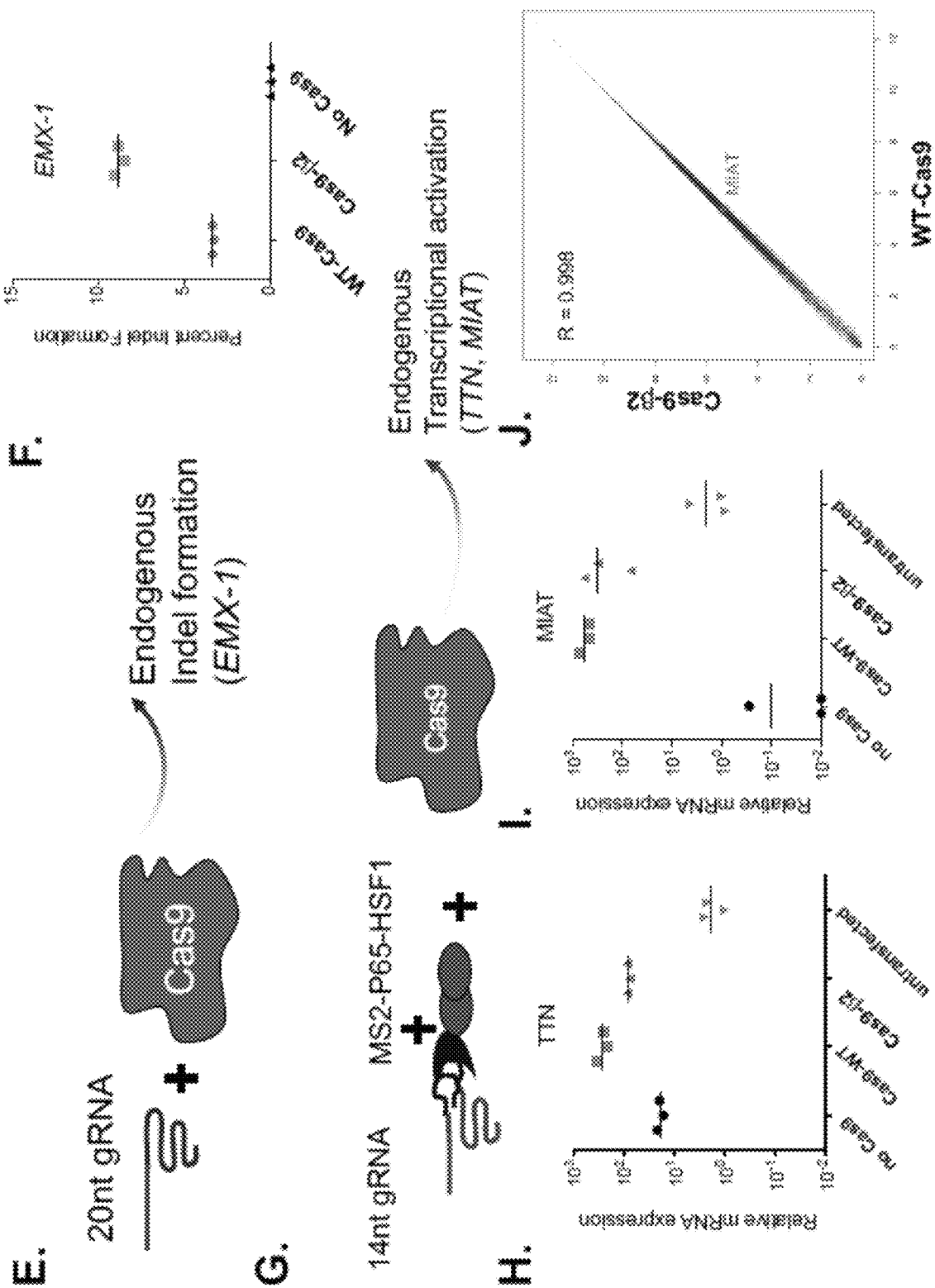
Figures 9A, 9B:
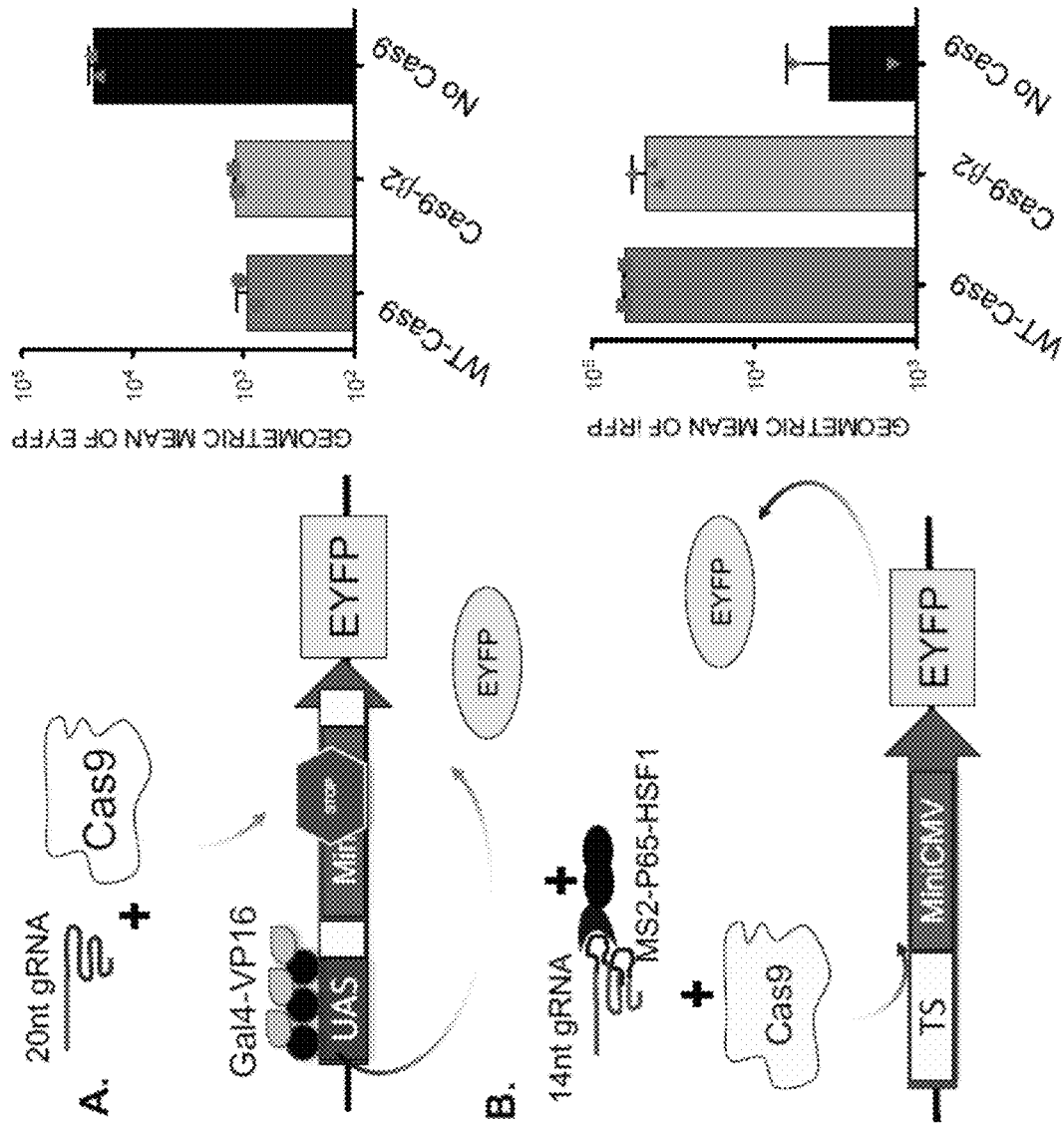
FIGS. 9A-9B. (A)(left) Schematic of the experiment assessing Cas9-$\beta$2 cleavage capacity at a synthetic promoter. Cells were transfected with either WT-Cas9, Cas9-$\beta$2, or an empty plasmid as well as 20 nt gRNA targeting a synthetic CRISPR promoter that harbors two gRNA target sites flanking a mini-CMV promoter. The targeting and cleavage at the promoter should disrupt the promoter and decrease EYFP expression. (A)(right) Bar graphs show mean +/–SD of geometric mean of EYFP expression 48 hours after the transfection in cells expressing >2×10$^2$ A.U of a transfection marker measured by flow cytometry (n=2 individual transfections represented by individual dots). (B)(left) Schematic of the experiment assessing Cas9-$\beta$2 transcriptional activation capacity at a synthetic promoter. Cells were transfected with either WTCas9, Cas9-$\beta$2 or an empty plasmid as well as aptamer binding transcriptional activation domains, and 14 nt gRNA targeting a synthetic CRISPR promoter that harbors multiple target sites upstream of a mini-CMV promoter. The targeting at the promoter should enable iRFP expression. (B(right) Bar graph shows mean +/–SD of geometric mean of iRFP expression 48 hours after the transfection in cells expressing >2×10$^2$ A.U of a transfection marker measured by flow cytometry (n=3 individual transfections represented by individual dots. n=2 for No Cas9 group).

A modified Cas9 construct was produced by mutating the second residue of peptide β (L616G; Cas9-β2) and tested the function of this new Cas9 variant in comparison with wild type Cas9 (WT-Cas9) in the context of DNA cleavage and transcriptional modulation. To examine the nuclease activity of Cas9-β2 and compare with WT-Cas9, Cas9-β2 or WT-Cas9 were targeted to an endogenous locus (EMX-1) and measured percent indel formation (FIGS. 7E, 7F). Our data demonstrate that Cas9-β2 retains nuclease capacity in the locus we studied as well as on a synthetic promoter (FIG. 7F, FIG. 9A). Next, it was determined whether Cas9-β2 can successfully recognize and bind its target DNA leading to transcriptional modulation. First, it was tested in the context of enhanced transgene expression from a synthetic CRISPR responsive promoter in HEK293 cells using 14 nt gRNAs and aptamer mediated recruitment of transcriptional modulators similar to what we had shown before (FIG. 9B). Having shown successful transgene activation, it was investigated whether this variant retains such capacity within the chromosomal contexts of endogenous genes. Cells were transfected with plasmids encoding Cas9-β2 or WT-Cas9 and 14 nt gRNAs against two different endogenous genes (TTN and MIAT). qRT-PCR analysis showed that this variant successfully led to target gene expression (FIGS. 7G-7I). To further characterize Cas9-β2 specificity, genome-wide RNA sequencing was performed after targeting Cas9-β2 or WT-Cas9 to the MIAT locus for transcriptional activation. The results demonstrated no significant increase in undesired off-target activity by Cas9-β2 as compared to WT-Cas9 (FIG. 7J).

Figures 10A, 10B, 10C, 10D, 10E, 10F:
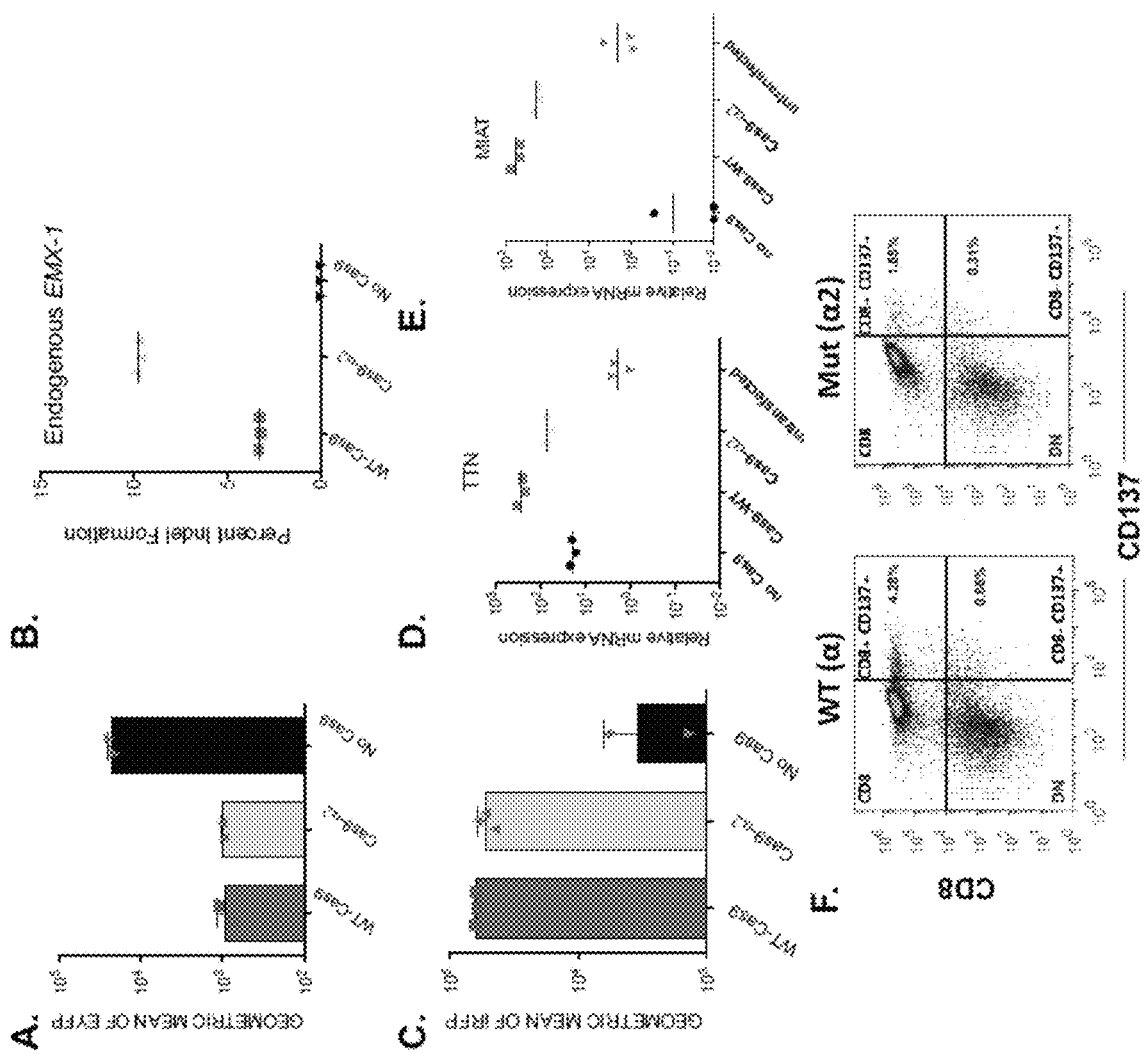
FIGS. 10A-10F. (A) Analysis of mutagenesis capacity of Cas9-$\alpha$2 as compared to WT Cas9 in a synthetic promoter. Bar graph shows mean +/–SD of geometric mean of EYFP expression 48 hr after transfection in cells expressing >2×10$^2$ A.U of a transfection marker measured by flow cytometry (n=2 individual transfections, represented by individual dots). (B) Mutagenesis in endogenous EMX-1 locus. Percentage of indel formation in EMX-1 locus. Dots represent three individual transfections. (C) Transcriptional modulation by Cas9-$\alpha$2 at a synthetic promoter. Bar graph is mean +/–SD of geometric mean of iRFP expression 48 hr after the transfection in cells expressing >2×10$^2$ A.U of a transfection marker measured by flow cytometry (n=3 individual transfections, n=2 for no Cas9 group represented by dots). (D, E) Shown is mRNA level relative to an untransfected control experiment. Each individual dot represent individual transfections. WT-Cas9 data and no Cas9 data for panels A and C are also presented in FIGS. 9A-9B. For B, D, and E, WT-Cas9 data and no Cas9 data are also presented in FIGS. 7A-7J. (F) Activated CD8+CD137+ T cells detected in PBMCs stimulated with peptide $\alpha$ was reduced in PBMCs stimulated with peptide $\alpha$2.

To show the extensibility of our approach, another Cas9 variant was generated by mutating the second residue of peptide α (L241G; Cas9-(2). Cas9-α2 also demonstrated DNA cleavage and transcriptional modulation functionality comparable with WT-Cas9 (FIGS. 10A-10E). When T cells were stimulated with APCs spiked with peptide α2, the percentage of CD8+CD137+ T cells (α marker of T cell activation) was decreased by 2.3 fold as compared to WT peptide α stimulation (FIG. 10F).

The detection of pre-existing B cell and T cell immunity to the most widely used nuclease ortholog of the CRISPR/Cas9 tool in a significant proportion of healthy humans confirms previous studies in mice and sheds light on the need for more studies of the immunological risks of this system. The CD8+ T cell immunity we observed is likely memory responses, as they are observed without ex vivo stimulation. Following 18 days of T cell stimulation by peptides α or β, expansion of naive T cells is not precluded. This suggests that the expression of Cas9 in naive individuals may trigger a T cell response that could prevent subsequent administration. This could be avoided by switching to Cas9 orthologs from other bacterial species, but attention needs to be given to individual and distinct immune repertoires. This can be difficult given the epitope conservation across Cas9 proteins from multiple *Streptococcus* species and resemblance to sequences from other bacterial proteins such as the common pathogen *N. meningitidis* that asymptomatically colonizes the nasopharynx in 10% of the population. Therefore, selective deimmunization (also known as immunosilencing) of Cas9 can represent an attractive alternative. Selective deimmunization can be an effective alternative for CRISPR applications in patients where systemic immunosuppression proves to be difficult, such as in patients with chronic infectious diseases. This strategy can be important particularly when longer expression of Cas9 will be desired for epigenetic therapy.

Conventional methods of deimmunizing non-human therapeutic proteins rely on trial-and-error mutagenesis, machine learning, and often includes deletion of whole regions of the protein. Here, as a general principle, it was determined that alteration of one of the anchor residues of an immunodominant epitope abolished specific T cell recognition. However, HLA allotype diversity and the existence of numerous epitopes in the large Cas9 protein complicate the process of complete deimmunization. The overall impact of removal of select immunodominant epitopes remains to be seen; similar approaches for other proteins have resulted in reduction and enhancement of the immunogenicity of subdominant epitopes. Non-specific immune suppressive approaches may complement these strategies for complete deimmunization. One attractive strategy is the co-expression of Cas9 with gRNAs targeting immune modulatory molecules such as programmed death-ligand 1 (PD-LI) or Indoleamine 2,3-Dioxygenase 1 (IDO1) to further boost immunosilencing. It is believed that deimmunized Cas9 will be useful for therapeutic CRISPR applications as a better understanding of the immunological consequences of this system develops.

The mutated Cas9 protein sequences are as follows, with peptides 85 (α) (SEQ ID NO:27) and 94 (β) (SEQ ID NO:28) in bold, underlined text:

```
Cas9-α2:
                                                        (SEQ ID NO: 2)
MDKKYSIGLDIGTNSVGWAVITDEYKVPSKKFKVLGNTDRHSIKKNLIGALLFDSGET

AEATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDLN

PDNSDVDKLFIQLVQTYNQLFEENPINASGVDAKAILSARLSKSRRLENLIAQLPGEKK

NGLFG**<u>NGIALSLGL</u>**TPNFKSNFDLAEDAKLQLSKDTYDDDLDNLLAQIGDQYADLFL

AAKNLSDAILLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRK

SEETITPWNFEEVVDKGASAQSFIERMTNFDKNLPNEKVLPKHSLLYEYFTVYNELTK

VKYVTEGMRKPAFLSGEQKKAIVDLLFKTNRKVTVKQLKEDYFKKIECFDSVEISGVE

DRFNASLGTYHDLLKIIKDKDFLDNEENED**<u>ILEDIVLTL</u>**TLFEDREMIEERLKTYAHLF

DDKVMKQLKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKVMGRHKPE

NIVIEMARENQTTQKGQKNSRERMKRIEEGIKELGSQILKEHPVENTQLQNEKLYLYY

LQNGRDMYVDQELDINRLSDYDVDHIVPQSFLKDDSIDNKVLTRSDKNRGKSDNVPS

EEVVKKMKNYWRQLLNAKLITQRKFDNLTKAERGGLSELDKAGFIKRQLVETRQITK

HVAQILDSRMNTKYDENDKLIREVKVITLKSKLVSDFRKDFQFYKVREINNYHHAHD

AYLNAVVGTALIKKYPKLESEFVYGDYKVYDVRKMIAKSEQEIGKATAKYFFYSNIM

NFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLK

SVKELLGITIMERSSFEKNPIDFLEAKGYKEVKKDLIIKLPKYSLFELENGRKRMLASA

GELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRK

RYTSTKEVLDATLIHQSITGLYETRIDLSQLGGD

Cas9-β2
                                                        (SEQ ID NO: 3)
MDKKYSIGLDIGTNSVGWAVITDEYKVPSKKFKVLGNTDRHSIKKNLIGALLFDSGET

AEATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDLN
```

```
PDNSDVDKLFIQLVQTYNQLFEENPINASGVDAKAILSARLSKSRRLENLIAQLPGEKK

NGLFGNLIALSLGLTPNFKSNFDLAEDAKLQLSKDTYDDDLDNLLAQIGDQYADLFL

AAKNLSDAILLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRK

SEETITPWNFEEVVDKGASAQSFIERMTNFDKNLPNEKVLPKHSLLYEYFTVYNELTK

VKYVTEGMRKPAFLSGEQKKAIVDLLFKTNRKVTVKQLKEDYFKKIECFDSVEISGVE

DRFNASLGTYHDLLKIIKDKDFLDNEENEDIGEDIVLTLTLFEDREMIEERLKTYAHLF

DDKVMKQLKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKVMGRHKPE

NIVIEMARENQTTQKGQKNSRERMKRIEEGIKELGSQILKEHPVENTQLQNEKLYLYY

LQNGRDMYVDQELDINRLSDYDVDHIVPQSFLKDDSIDNKVLTRSDKNRGKSDNVPS

EEVVKKMKNYWRQLLNAKLITQRKFDNLTKAERGGLSELDKAGFIKRQLVETRQITK

HVAQILDSRMNTKYDENDKLIREVKVITLKSKLVSDFRKDFQFYKVREINNYHHAHD

AYLNAVVGTALIKKYPKLESEFVYGDYKVYDVRKMIAKSEQEIGKATAKYFFYSNIM

NFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLK

SVKELLGITIMERSSFEKNPIDFLEAKGYKEVKKDLIIKLPKYSLFELENGRKRMLASA

GELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRK

RYTSTKEVLDATLIHQSITGLYETRIDLSQLGGD
```

Cas9-α2-β2
(SEQ ID NO: 4)

```
MDKKYSIGLDIGTNSVGWAVITDEYKVPSKKFKVLGNTDRHSIKKNLIGALLFDSGET

AEATRLKRTARRRYTRRKNRICYLQEIFSNEMAKVDDSFFHRLEESFLVEEDKKHERH

PIFGNIVDEVAYHEKYPTIYHLRKKLVDSTDKADLRLIYLALAHMIKFRGHFLIEGDLN

PDNSDVDKLFIQLVQTYNQLFEENPINASGVDAKAILSARLSKSRRLENLIAQLPGEKK

NGLFGNGIALSLGLTPNFKSNFDLAEDAKLQLSKDTYDDDLDNLLAQIGDQYADLFL

AAKNLSDAILLSDILRVNTEITKAPLSASMIKRYDEHHQDLTLLKALVRQQLPEKYKEI

FFDQSKNGYAGYIDGGASQEEFYKFIKPILEKMDGTEELLVKLNREDLLRKQRTFDNG

SIPHQIHLGELHAILRRQEDFYPFLKDNREKIEKILTFRIPYYVGPLARGNSRFAWMTRK

SEETITPWNFEEVVDKGASAQSFIERMTNFDKNLPNEKVLPKHSLLYEYFTVYNELTK

VKYVTEGMRKPAFLSGEQKKAIVDLLFKTNRKVTVKQLKEDYFKKIECFDSVEISGVE

DRFNASLGTYHDLLKIIKDKDFLDNEENEDIGEDIVLTLTLFEDREMIEERLKTYAHLF

DDKVMKQLKRRRYTGWGRLSRKLINGIRDKQSGKTILDFLKSDGFANRNFMQLIHDD

SLTFKEDIQKAQVSGQGDSLHEHIANLAGSPAIKKGILQTVKVVDELVKVMGRHKPE

NIVIEMARENQTTQKGQKNSRERMKRIEEGIKELGSQILKEHPVENTQLQNEKLYLYY

LQNGRDMYVDQELDINRLSDYDVDHIVPQSFLKDDSIDNKVLTRSDKNRGKSDNVPS

EEVVKKMKNYWRQLLNAKLITQRKFDNLTKAERGGLSELDKAGFIKRQLVETRQITK

HVAQILDSRMNTKYDENDKLIREVKVITLKSKLVSDFRKDFQFYKVREINNYHHAHD

AYLNAVVGTALIKKYPKLESEFVYGDYKVYDVRKMIAKSEQEIGKATAKYFFYSNIM
```

-continued

NFFKTEITLANGEIRKRPLIETNGETGEIVWDKGRDFATVRKVLSMPQVNIVKKTEVQ

TGGFSKESILPKRNSDKLIARKKDWDPKKYGGFDSPTVAYSVLVVAKVEKGKSKKLK

SVKELLGITIMERSSFEKNPIDFLEAKGYKEVKKDLIIKLPKYSLFELENGRKRMLASA

GELQKGNELALPSKYVNFLYLASHYEKLKGSPEDNEQKQLFVEQHKHYLDEIIEQISE

FSKRVILADANLDKVLSAYNKHRDKPIREQAENIIHLFTLTNLGAPAAFKYFDTTIDRK

RYTSTKEVLDATLIHQSITGLYETRIDLSQLGGD

Cas9-β2:

(SEQ ID NO: 6)
ATGGACTATAAGGACCACGACGGAGACTACAAGGATCATGATATTGATTACAAAGACGATGACGA

TAAGATGGCCCCAAAGAAGAAGCGGAAGGTCGGTATCCACGGAGTCCCAGCAGCCGACAAGAAG

TACAGCATCGGCCTGGACATCGGCACCAACTCTGTGGGCTGGGCCGTGATCACCGACGAGTACAA

GGTGCCCAGCAAGAAATTCAAGGTGCTGGGCAACACCGACCGGCACAGCATCAAGAAGAACCTG

ATCGGAGCCCTGCTGTTCGACAGCGGCGAAACAGCCGAGGCCACCCGGCTGAAGAGAACCGCCA

GAAGAAGATACACCAGACGGAAGAACCGGATCTGCTATCTGCAAGAGATCTTCAGCAACGAGAT

GGCCAAGGTGGACGACAGCTTCTTCCACAGACTGGAAGAGTCCTTCCTGGTGGAAGAGGATAAGA

AGCACGAGCGGCACCCCATCTTCGGCAACATCGTGGACGAGGTGGCCTACCACGAGAAGTACCCC

ACCATCTACCACCTGAGAAAGAAACTGGTGGACAGCACCGACAAGGCCGACCTGCGGCTGATCTA

TCTGGCCCTGGCCCACATGATCAAGTTCCGGGGCCACTTCCTGATCGAGGGCGACCTGAACCCCG

ACAACAGCGACGTGGACAAGCTGTTCATCCAGCTGGTGCAGACCTACAACCAGCTGTTCGAGGAA

AACCCCATCAACGCCAGCGGCGTGGACGCCAAGGCCATCCTGTCTGCCAGACTGAGCAAGAGCAG

ACGGCTGGAAAATCTGATCGCCCAGCTGCCCGGCGAGAAGAAGAATGGCCTGTTCGGAAACCTTA

TTGCCCTGAGCCTGGGCCTGACCCCCAACTTCAAGAGCAACTTCGACCTGGCCGAGGATGCCAAA

CTGCAGCTGAGCAAGGACACCTACGACGACGACCTGGACAACCTGCTGGCCCAGATCGGCGACCA

GTACGCCGACCTGTTTCTGGCCGCCAAGAACCTGTCCGACGCCATCCTGCTGAGCGACATCCTGAG

AGTGAACACCGAGATCACCAAGGCCCCCCTGAGCGCCTCTATGATCAAGAGATACGACGAGCACC

ACCAGGACCTGACCCTGCTGAAAGCTCTCGTGCGGCAGCAGCTGCCTGAGAAGTACAAAGAGATT

TTCTTCGACCAGAGCAAGAACGGCTACGCCGGCTACATTGACGGCGGAGCCAGCCAGGAAGAGTT

CTACAAGTTCATCAAGCCCATCCTGGAAAAGATGGACGGCACCGAGGAACTGCTCGTGAAGCTGA

ACAGAGAGGACCTGCTGCGGAAGCAGCGGACCTTCGACAACGGCAGCATCCCCCACCAGATCCAC

CTGGGAGAGCTGCACGCCATTCTGCGGCGGCAGGAAGATTTTTACCCATTCCTGAAGGACAACCG

GGAAAAGATCGAGAAGATCCTGACCTTCCGCATCCCCTACTACGTGGGCCCTCTGGCCAGGGGAA

ACAGCAGATTCGCCTGGATGACCAGAAAGAGCGAGGAAACCATCACCCCCTGGAACTTCGAGGA

AGTGGTGGACAAGGGCGCTTCCGCCCAGAGCTTCATCGAGCGGATGACCAACTTCGATAAGAACC

TGCCCAACGAGAAGGTGCTGCCCAAGCACAGCCTGCTGTACGAGTACTTCACCGTGTATAACGAG

CTGACCAAAGTGAAATACGTGACCGAGGGAATGAGAAAGCCCGCCTTCCTGAGCGGCGAGCAGA

AAAAGGCCATCGTGGACCTGCTGTTCAAGACCAACCGGAAAGTGACCGTGAAGCAGCTGAAAGA

GGACTACTTCAAGAAAATCGAGTGCTTCGACTCCGTGGAAATCTCCGGCGTGGAAGATCGGTTCA

ACGCCTCCCTGGGCACATACCACGATCTGCTGAAAATTATCAAGGACAAGGACTTCCTGGACAAT

GAGGAAAACGAGGACATTGGTGAAGATATCGTGCTGACCCTGACACTGTTTGAGGACAGAGAGAT

GATCGAGGAACGGCTGAAAACCTATGCCCACCTGTTCGACGACAAAGTGATGAAGCAGCTGAAGC

GGCGGAGATACACCGGCTGGGGCAGGCTGAGCCGGAAGCTGATCAACGGCATCCGGGACAAGCA

GTCCGGCAAGACAATCCTGGATTTCCTGAAGTCCGACGGCTTCGCCAACAGAAACTTCATGCAGC

-continued

```
TGATCCACGACGACAGCCTGACCTTTAAAGAGGACATCCAGAAAGCCCAGGTGTCCGGCCAGGGC

GATAGCCTGCACGAGCACATTGCCAATCTGGCCGGCAGCCCCGCCATTAAGAAGGGCATCCTGCA

GACAGTGAAGGTGGTGGACGAGCTCGTGAAAGTGATGGGCCGGCACAAGCCCGAGAACATCGTG

ATCGAAATGGCCAGAGAGAACCAGACCACCCAGAAGGGACAGAAGAACAGCCGCGAGAGAATG

AAGCGGATCGAAGAGGGCATCAAAGAGCTGGGCAGCCAGATCCTGAAAGAACACCCCGTGGAAA

ACACCCAGCTGCAGAACGAGAAGCTGTACCTGTACTACCTGCAGAATGGGCGGGATATGTACGTG

GACCAGGAACTGGACATCAACCGGCTGTCCGACTACGATGTGGACCATATCGTGCCTCAGAGCTT

TCTGAAGGACGACTCCATCGACAACAAGGTGCTGACCAGAAGCGACAAGAACCGGGGCAAGAGC

GACAACGTGCCCTCCGAAGAGGTCGTGAAGAAGATGAAGAACTACTGGCGGCAGCTGCTGAACG

CCAAGCTGATTACCCAGAGAAAGTTCGACAATCTGACCAAGGCCGAGAGAGGCGGCCTGAGCGA

ACTGGATAAGGCCGGCTTCATCAAGAGACAGCTGGTGGAAACCCGGCAGATCACAAAGCACGTG

GCACAGATCCTGGACTCCCGGATGAACACTAAGTACGACGAGAATGACAAGCTGATCCGGGAAGT

GAAAGTGATCACCCTGAAGTCCAAGCTGGTGTCCGATTTCCGGAAGGATTTCCAGTTTTACAAAGT

GCGCGAGATCAACAACTACCACCACGCCCACGACGCCTACCTGAACGCCGTCGTGGGAACCGCCC

TGATCAAAAAGTACCCTAAGCTGGAAAGCGAGTTCGTGTACGGCGACTACAAGGTGTACGACGTG

CGGAAGATGATCGCCAAGAGCGAGCAGGAAATCGGCAAGGCTACCGCCAAGTACTTCTTCTACAG

CAACATCATGAACTTTTTCAAGACCGAGATTACCCTGGCCAACGGCGAGATCCGGAAGCGGCCTC

TGATCGAGACAAACGGCGAAACCGGGGAGATCGTGTGGGATAAGGGCCGGGATTTTGCCACCGTG

CGGAAAGTGCTGAGCATGCCCCAAGTGAATATCGTGAAAAAGACCGAGGTGCAGACAGGCGGCT

TCAGCAAAGAGTCTATCCTGCCCAAGAGGAACAGCGATAAGCTGATCGCCAGAAAGAAGGACTG

GGACCCTAAGAAGTACGGCGGCTTCGACAGCCCCACCGTGGCCTATTCTGTGCTGGTGGTGGCCA

AAGTGGAAAAGGGCAAGTCCAAGAAACTGAAGAGTGTGAAAGAGCTGCTGGGGATCACCATCAT

GGAAAGAAGCAGCTTCGAGAAGAATCCCATCGACTTTCTGGAAGCCAAGGGCTACAAAGAAGTG

AAAAAGGACCTGATCATCAAGCTGCCTAAGTACTCCCTGTTCGAGCTGGAAAACGGCCGGAAGAG

AATGCTGGCCTCTGCCGGCGAACTGCAGAAGGGAAACGAACTGGCCCTGCCCTCCAAATATGTGA

ACTTCCTGTACCTGGCCAGCCACTATGAGAAGCTGAAGGGCTCCCCCGAGGATAATGAGCAGAAA

CAGCTGTTTGTGGAACAGCACAAGCACTACCTGGACGAGATCATCGAGCAGATCAGCGAGTTCTC

CAAGAGAGTGATCCTGGCCGACGCTAATCTGGACAAAGTGCTGTCCGCCTACAACAAGCACCGGG

ATAAGCCCATCAGAGAGCAGGCCGAGAATATCATCCACCTGTTTACCCTGACCAATCTGGGAGCC

CCTGCCGCCTTCAAGTACTTTGACACCACCATCGACCGGAAGAGGTACACCAGCACCAAAGAGGT

GCTGGACGCCACCCTGATCCACCAGAGCATCACCGGCCTGTACGAGACACGGATCGACCTGTCTC

AGCTGGGAGGCGACAAAAGGCCGGCGGCCACGAAAAAGGCCGGCCAGGCAAAAAAGAAAAAGT

AA

Cas9-α2:
                                                                 (SEQ ID NO: 7)
ATGGACTATAAGGACCACGACGGAGACTACAAGGATCATGATATTGATTACAAAGACGATGACGA

TAAGATGGCCCCAAAGAAGAAGCGGAAGGTCGGTATCCACGGAGTCCCAGCAGCCGACAAGAAG

TACAGCATCGGCCTGGACATCGGCACCAACTCTGTGGGCTGGGCCGTGATCACCGACGAGTACAA

GGTGCCCAGCAAGAAATTCAAGGTGCTGGGCAACACCGACCGGCACAGCATCAAGAAGAACCTG

ATCGGAGCCCTGCTGTTCGACAGCGGCGAAACAGCCGAGGCCACCCGGCTGAAGAGAACCGCCA

GAAGAAGATACACCAGACGGAAGAACCGGATCTGCTATCTGCAAGAGATCTTCAGCAACGAGAT
```

-continued

```
GGCCAAGGTGGACGACAGCTTCTTCCACAGACTGGAAGAGTCCTTCCTGGTGGAAGAGGATAAGA

AGCACGAGCGGCACCCCATCTTCGGCAACATCGTGGACGAGGTGGCCTACCACGAGAAGTACCCC

ACCATCTACCACCTGAGAAAGAAACTGGTGGACAGCACCGACAAGGCCGACCTGCGGCTGATCTA

TCTGGCCCTGGCCCACATGATCAAGTTCCGGGGCCACTTCCTGATCGAGGGCGACCTGAACCCCG

ACAACAGCGACGTGGACAAGCTGTTCATCCAGCTGGTGCAGACCTACAACCAGCTGTTCGAGGAA

AACCCCATCAACGCCAGCGGCGTGGACGCCAAGGCCATCCTGTCTGCCAGACTGAGCAAGAGCAG

ACGGCTGGAAAATCTGATCGCCCAGCTGCCCGGCGAGAAGAAGAATGGCCTGTTCGGAAACGGTA

TTGCCCTGAGCCTGGGCCTGACCCCCAACTTCAAGAGCAACTTCGACCTGGCCGAGGATGCCAAA

CTGCAGCTGAGCAAGGACACCTACGACGACGACCTGGACAACCTGCTGGCCCAGATCGGCGACCA

GTACGCCGACCTGTTTCTGGCCGCCAAGAACCTGTCCGACGCCATCCTGCTGAGCGACATCCTGAG

AGTGAACACCGAGATCACCAAGGCCCCCCTGAGCGCCTCTATGATCAAGAGATACGACGAGCACC

ACCAGGACCTGACCCTGCTGAAAGCTCTCGTGCGGCAGCAGCTGCCTGAGAAGTACAAAGAGATT

TTCTTCGACCAGAGCAAGAACGGCTACGCCGGCTACATTGACGGCGGAGCCAGCCAGGAAGAGTT

CTACAAGTTCATCAAGCCCATCCTGGAAAAGATGGACGGCACCGAGGAACTGCTCGTGAAGCTGA

ACAGAGAGGACCTGCTGCGGAAGCAGCGGACCTTCGACAACGGCAGCATCCCCCACCAGATCCAC

CTGGGAGAGCTGCACGCCATTCTGCGGCGGCAGGAAGATTTTTACCCATTCCTGAAGGACAACCG

GGAAAAGATCGAGAAGATCCTGACCTTCCGCATCCCCTACTACGTGGGCCCTCTGGCCAGGGGAA

ACAGCAGATTCGCCTGGATGACCAGAAAGAGCGAGGAAACCATCACCCCCTGGAACTTCGAGGA

AGTGGTGGACAAGGGCGCTTCCGCCCAGAGCTTCATCGAGCGGATGACCAACTTCGATAAGAACC

TGCCCAACGAGAAGGTGCTGCCCAAGCACAGCCTGCTGTACGAGTACTTCACCGTGTATAACGAG

CTGACCAAAGTGAAATACGTGACCGAGGGAATGAGAAAGCCCGCCTTCCTGAGCGGCGAGCAGA

AAAAGGCCATCGTGGACCTGCTGTTCAAGACCAACCGGAAAGTGACCGTGAAGCAGCTGAAAGA

GGACTACTTCAAGAAAATCGAGTGCTTCGACTCCGTGGAAATCTCCGGCGTGGAAGATCGGTTCA

ACGCCTCCCTGGGCACATACCACGATCTGCTGAAAATTATCAAGGACAAGGACTTCCTGGACAAT

GAGGAAAACGAGGACATTCTTGAAGATATCGTGCTGACCCTGACACTGTTTGAGGACAGAGAGAT

GATCGAGGAACGGCTGAAAACCTATGCCCACCTGTTCGACGACAAAGTGATGAAGCAGCTGAAGC

GGCGGAGATACACCGGCTGGGGCAGGCTGAGCCGGAAGCTGATCAACGGCATCCGGGACAAGCA

GTCCGGCAAGACAATCCTGGATTTCCTGAAGTCCGACGGCTTCGCCAACAGAAACTTCATGCAGC

TGATCCACGACGACAGCCTGACCTTTAAAGAGGACATCCAGAAAGCCCAGGTGTCCGGCCAGGGC

GATAGCCTGCACGAGCACATTGCCAATCTGGCCGGCAGCCCCGCCATTAAGAAGGGCATCCTGCA

GACAGTGAAGGTGGTGGACGAGCTCGTGAAAGTGATGGGCCGGCACAAGCCCGAGAACATCGTG

ATCGAAATGGCCAGAGAGAACCAGACCACCCAGAAGGGACAGAAGAACAGCCGCGAGAGAATG

AAGCGGATCGAAGAGGGCATCAAAGAGCTGGGCAGCCAGATCCTGAAAGAACACCCCGTGGAAA

ACACCCAGCTGCAGAACGAGAAGCTGTACCTGTACTACCTGCAGAATGGGCGGGATATGTACGTG

GACCAGGAACTGGACATCAACCGGCTGTCCGACTACGATGTGGACCATATCGTGCCTCAGAGCTT

TCTGAAGGACGACTCCATCGACAACAAGGTGCTGACCAGAAGCGACAAGAACCGGGGCAAGAGC

GACAACGTGCCCTCCGAAGAGGTCGTGAAGAAGATGAAGAACTACTGGCGGCAGCTGCTGAACG

CCAAGCTGATTACCCAGAGAAAGTTCGACAATCTGACCAAGGCCGAGAGAGGCGGCCTGAGCGA

ACTGGATAAGGCCGGCTTCATCAAGAGACAGCTGGTGGAAACCCGGCAGATCACAAAGCACGTG

GCACAGATCCTGGACTCCCGGATGAACACTAAGTACGACGAGAATGACAAGCTGATCCGGGAAGT

GAAAGTGATCACCCTGAAGTCCAAGCTGGTGTCCGATTTCCGGAAGGATTTCCAGTTTTACAAAGT
```

-continued

```
GCGCGAGATCAACAACTACCACCACGCCCACGACGCCTACCTGAACGCCGTCGTGGGAACCGCCC
TGATCAAAAAGTACCCTAAGCTGGAAAGCGAGTTCGTGTACGGCGACTACAAGGTGTACGACGTG
CGGAAGATGATCGCCAAGAGCGAGCAGGAAATCGGCAAGGCTACCGCCAAGTACTTCTTCTACAG
CAACATCATGAACTTTTTCAAGACCGAGATTACCCTGGCCAACGGCGAGATCCGGAAGCGGCCTC
TGATCGAGACAAACGGCGAAACCGGGGAGATCGTGTGGGATAAGGGCCGGGATTTTGCCACCGTG
CGGAAAGTGCTGAGCATGCCCCAAGTGAATATCGTGAAAAAGACCGAGGTGCAGACAGGCGGCT
TCAGCAAAGAGTCTATCCTGCCCAAGAGGAACAGCGATAAGCTGATCGCCAGAAAGAAGGACTG
GGACCCTAAGAAGTACGGCGGCTTCGACAGCCCCACCGTGGCCTATTCTGTGCTGGTGGTGGCCA
AAGTGGAAAAGGGCAAGTCCAAGAAACTGAAGAGTGTGAAAGAGCTGCTGGGGATCACCATCAT
GGAAAGAAGCAGCTTCGAGAAGAATCCCATCGACTTTCTGGAAGCCAAGGGCTACAAAGAAGTG
AAAAAGGACCTGATCATCAAGCTGCCTAAGTACTCCCTGTTCGAGCTGGAAAACGGCCGGAAGAG
AATGCTGGCCTCTGCCGGCGAACTGCAGAAGGGAAACGAACTGGCCCTGCCCTCCAAATATGTGA
ACTTCCTGTACCTGGCCAGCCACTATGAGAAGCTGAAGGGCTCCCCCGAGGATAATGAGCAGAAA
CAGCTGTTTGTGGAACAGCACAAGCACTACCTGGACGAGATCATCGAGCAGATCAGCGAGTTCTC
CAAGAGAGTGATCCTGGCCGACGCTAATCTGGACAAAGTGCTGTCCGCCTACAACAAGCACCGGG
ATAAGCCCATCAGAGAGCAGGCCGAGAATATCATCCACCTGTTTACCCTGACCAATCTGGGAGCC
CCTGCCGCCTTCAAGTACTTTGACACCACCATCGACCGGAAGAGGTACACCAGCACCAAAGAGGT
GCTGGACGCCACCCTGATCCACCAGAGCATCACCGGCCTGTACGAGACACGGATCGACCTGTCTC
AGCTGGGAGGCGACAAAAGGCCGGCGGCCACGAAAAAGGCCGGCCAGGCAAAAAAGAAAAAGT
AAG
```

Cas9-α2-β2
(SEQ ID NO: 8)
```
ATGGACTATAAGGACCACGACGGAGACTACAAGGATCATGATATTGATTACAAAGACGATGACGA
TAAGATGGCCCCAAAGAAGAAGCGGAAGGTCGGTATCCACGGAGTCCCAGCAGCCGACAAGAAG
TACAGCATCGGCCTGGACATCGGCACCAACTCTGTGGGCTGGGCCGTGATCACCGACGAGTACAA
GGTGCCCAGCAAGAAATTCAAGGTGCTGGGCAACACCGACCGGCACAGCATCAAGAAGAACCTG
ATCGGAGCCCTGCTGTTCGACAGCGGCGAAACAGCCGAGGCCACCCGGCTGAAGAGAACCGCCA
GAAGAAGATACACCAGACGGAAGAACCGGATCTGCTATCTGCAAGAGATCTTCAGCAACGAGAT
GGCCAAGGTGGACGACAGCTTCTTCCACAGACTGGAAGAGTCCTTCCTGGTGGAAGAGGATAAGA
AGCACGAGCGGCACCCCATCTTCGGCAACATCGTGGACGAGGTGGCCTACCACGAGAAGTACCCC
ACCATCTACCACCTGAGAAAGAAACTGGTGGACAGCACCGACAAGGCCGACCTGCGGCTGATCTA
TCTGGCCCTGGCCCACATGATCAAGTTCCGGGGCCACTTCCTGATCGAGGGCGACCTGAACCCCG
ACAACAGCGACGTGGACAAGCTGTTCATCCAGCTGGTGCAGACCTACAACCAGCTGTTCGAGGAA
AACCCCATCAACGCCAGCGGCGTGGACGCCAAGGCCATCCTGTCTGCCAGACTGAGCAAGAGCAG
ACGGCTGGAAAATCTGATCGCCCAGCTGCCCGGCGAGAAGAAGAATGGCCTGTTCGGAAACGGTA
TTGCCCTGAGCCTGGGCCTGACCCCCAACTTCAAGAGCAACTTCGACCTGGCCGAGGATGCCAAA
CTGCAGCTGAGCAAGGACACCTACGACGACGACCTGGACAACCTGCTGGCCCAGATCGGCGACCA
GTACGCCGACCTGTTTCTGGCCGCCAAGAACCTGTCCGACGCCATCCTGCTGAGCGACATCCTGAG
AGTGAACACCGAGATCACCAAGGCCCCCCTGAGCGCCTCTATGATCAAGAGATACGACGAGCACC
ACCAGGACCTGACCCTGCTGAAAGCTCTCGTGCGGCAGCAGCTGCCTGAGAAGTACAAAGAGATT
TTCTTCGACCAGAGCAAGAACGGCTACGCCGGCTACATTGACGGCGGAGCCAGCCAGGAAGAGTT
```

-continued

```
CTACAAGTTCATCAAGCCCATCCTGGAAAAGATGGACGGCACCGAGGAACTGCTCGTGAAGCTGA
ACAGAGAGGACCTGCTGCGGAAGCAGCGGACCTTCGACAACGGCAGCATCCCCCACCAGATCCAC
CTGGGAGAGCTGCACGCCATTCTGCGGCGGCAGGAAGATTTTTACCCATTCCTGAAGGACAACCG
GGAAAAGATCGAGAAGATCCTGACCTTCCGCATCCCCTACTACGTGGGCCCTCTGGCCAGGGGAA
ACAGCAGATTCGCCTGGATGACCAGAAAGAGCGAGGAAACCATCACCCCCTGGAACTTCGAGGA
AGTGGTGGACAAGGGCGCTTCCGCCCAGAGCTTCATCGAGCGGATGACCAACTTCGATAAGAACC
TGCCCAACGAGAAGGTGCTGCCCAAGCACAGCCTGCTGTACGAGTACTTCACCGTGTATAACGAG
CTGACCAAAGTGAAATACGTGACCGAGGGAATGAGAAAGCCCGCCTTCCTGAGCGGCGAGCAGA
AAAAGGCCATCGTGGACCTGCTGTTCAAGACCAACCGGAAAGTGACCGTGAAGCAGCTGAAAGA
GGACTACTTCAAGAAAATCGAGTGCTTCGACTCCGTGGAAATCTCCGGCGTGGAAGATCGGTTCA
ACGCCTCCCTGGGCACATACCACGATCTGCTGAAAATTATCAAGGACAAGGACTTCCTGGACAAT
GAGGAAAACGAGGACATTGGTGAAGATATCGTGCTGACCCTGACACTGTTTGAGGACAGAGAGAT
GATCGAGGAACGGCTGAAAACCTATGCCCACCTGTTCGACGACAAAGTGATGAAGCAGCTGAAGC
GGCGGAGATACACCGGCTGGGGCAGGCTGAGCCGGAAGCTGATCAACGGCATCCGGGACAAGCA
GTCCGGCAAGACAATCCTGGATTTCCTGAAGTCCGACGGCTTCGCCAACAGAAACTTCATGCAGC
TGATCCACGACGACAGCCTGACCTTTAAAGAGGACATCCAGAAAGCCCAGGTGTCCGGCCAGGGC
GATAGCCTGCACGAGCACATTGCCAATCTGGCCGGCAGCCCCGCCATTAAGAAGGGCATCCTGCA
GACAGTGAAGGTGGTGGACGAGCTCGTGAAAGTGATGGGCCGGCACAAGCCCGAGAACATCGTG
ATCGAAATGGCCAGAGAGAACCAGACCACCCAGAAGGGACAGAAGAACAGCCGCGAGAGAATG
AAGCGGATCGAAGAGGGCATCAAAGAGCTGGGCAGCCAGATCCTGAAAGAACACCCCGTGGAAA
ACACCCAGCTGCAGAACGAGAAGCTGTACCTGTACTACCTGCAGAATGGGCGGGATATGTACGTG
GACCAGGAACTGGACATCAACCGGCTGTCCGACTACGATGTGGACCATATCGTGCCTCAGAGCTT
TCTGAAGGACGACTCCATCGACAACAAGGTGCTGACCAGAAGCGACAAGAACCGGGGCAAGAGC
GACAACGTGCCCTCCGAAGAGGTCGTGAAGAAGATGAAGAACTACTGGCGGCAGCTGCTGAACG
CCAAGCTGATTACCCAGAGAAAGTTCGACAATCTGACCAAGGCCGAGAGAGGCGGCCTGAGCGA
ACTGGATAAGGCCGGCTTCATCAAGAGACAGCTGGTGGAAACCCGGCAGATCACAAAGCACGTG
GCACAGATCCTGGACTCCCGGATGAACACTAAGTACGACGAGAATGACAAGCTGATCCGGGAAGT
GAAAGTGATCACCCTGAAGTCCAAGCTGGTGTCCGATTTCCGGAAGGATTTCCAGTTTTACAAAGT
GCGCGAGATCAACAACTACCACCACGCCCACGACGCCTACCTGAACGCCGTCGTGGGAACCGCCC
TGATCAAAAAGTACCCTAAGCTGGAAAGCGAGTTCGTGTACGGCGACTACAAGGTGTACGACGTG
CGGAAGATGATCGCCAAGAGCGAGCAGGAAATCGGCAAGGCTACCGCCAAGTACTTCTTCTACAG
CAACATCATGAACTTTTTCAAGACCGAGATTACCCTGGCCAACGGCGAGATCCGGAAGCGGCCTC
TGATCGAGACAAACGGCGAAACCGGGGAGATCGTGTGGGATAAGGGCCGGGATTTTGCCACCGTG
CGGAAAGTGCTGAGCATGCCCCAAGTGAATATCGTGAAAAAGACCGAGGTGCAGACAGGCGGCT
TCAGCAAAGAGTCTATCCTGCCCAAGAGGAACAGCGATAAGCTGATCGCCAGAAAGAAGGACTG
GGACCCTAAGAAGTACGGCGGCTTCGACAGCCCCACCGTGGCCTATTCTGTGCTGGTGGTGGCCA
AAGTGGAAAAGGGCAAGTCCAAGAAACTGAAGAGTGTGAAAGAGCTGCTGGGGATCACCATCAT
GGAAAGAAGCAGCTTCGAGAAGAATCCCATCGACTTTCTGGAAGCCAAGGGCTACAAAGAAGTG
AAAAAGGACCTGATCATCAAGCTGCCTAAGTACTCCCTGTTCGAGCTGGAAAACGGCCGGAAGAG
AATGCTGGCCTCTGCCGGCGAACTGCAGAAGGGAAACGAACTGGCCCTGCCCTCCAAATATGTGA
ACTTCCTGTACCTGGCCAGCCACTATGAGAAGCTGAAGGGCTCCCCCGAGGATAATGAGCAGAAA
```

-continued

```
CAGCTGTTTGTGGAACAGCACAAGCACTACCTGGACGAGATCATCGAGCAGATCAGCGAGTTCTC

CAAGAGAGTGATCCTGGCCGACGCTAATCTGGACAAAGTGCTGTCCGCCTACAACAAGCACCGGG

ATAAGCCCATCAGAGAGCAGGCCGAGAATATCATCCACCTGTTTACCCTGACCAATCTGGGAGCC

CCTGCCGCCTTCAAGTACTTTGACACCACCATCGACCGGAAGAGGTACACCAGCACCAAAGAGGT

GCTGGACGCCACCCTGATCCACCAGAGCATCACCGGCCTGTACGAGACACGGATCGACCTGTCTC

AGCTGGGAGGCGACAAAAGGCCGGCGGCCACGAAAAAGGCCGGCCAGGCAAAAAAGAAAAAGT
```

We claim:

1. A method of altering the expression of at least one gene product in a subject, the method comprising:
   introducing into a cell from the subject an engineered Type II CRISPR-Cas system comprising a Cas9 protein and at least one guide RNA that hybridizes to a target sequence within a DNA molecule that encodes the at least one gene product in the cell, wherein the Cas9 protein comprises the amino acid sequence of SEQ ID NO:3 or SEQ ID NO:4, wherein the Cas9 protein has decreased immunogenicity as compared to the Cas9 protein of SEQ ID NO:1, and wherein expression of the at least one gene product is altered.

2. The method of claim 1, wherein the introducing step is performed ex vivo or in vivo.

3. The method of claim 1, further comprising screening a sample from the subject to detect the presence of an immune response to Cas9 in the subject.

4. The method of claim 3, wherein the sample comprises peripheral blood mononuclear cells.

5. The method of claim 1, wherein the Cas9 protein comprises the amino acid sequence of SEQ ID NO: 3.

6. The method of claim 1, wherein the Cas9 protein comprises the amino acid sequence of SEQ ID NO: 4.

* * * * *

UNITED STATES PATENT AND TRADEMARK OFFICE
CERTIFICATE OF CORRECTION

PATENT NO. : 11,208,640 B2
APPLICATION NO. : 16/632782
DATED : December 28, 2021
INVENTOR(S) : Radwa Ewaisha et al.

It is certified that error appears in the above-identified patent and that said Letters Patent is hereby corrected as shown below:

In the Specification

Column 3, Line 52, "FAX-1" should be --EMX-2--.

Column 15, Line 28, "IEDB consensus" should be --IEDBconsensus--.

Column 20, Line 17, "49.0/had" should be --49.0% had--.

Signed and Sealed this
Twelfth Day of April, 2022

Drew Hirshfeld
*Performing the Functions and Duties of the
Under Secretary of Commerce for Intellectual Property and
Director of the United States Patent and Trademark Office*

SEQUENCE LISTING

<160> NUMBER OF SEQ ID NOS: 82

<210> SEQ ID NO 1
<211> LENGTH: 1368
<212> TYPE: PRT
<213> ORGANISM: Streptococcus pyogenes

<400> SEQUENCE: 1

```
Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285
```

```
Leu Phe Leu Ala Ala Lys Asn Leu Ser Asp Ala Ile Leu Ser Asp
            290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
                355                 360                 365
Gln Glu Glu Phe Tyr Lys Phe Ile Lys Pro Ile Leu Glu Lys Met Asp
            370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
                435                 440                 445
Pro Tyr Tyr Val Gly Pro Leu Ala Arg Gly Asn Ser Arg Phe Ala Trp
            450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
                500                 505                 510
Leu Leu Tyr Glu Tyr Phe Thr Val Tyr Asn Glu Leu Thr Lys Val Lys
            515                 520                 525
Tyr Val Thr Glu Gly Met Arg Lys Pro Ala Phe Leu Ser Gly Glu Gln
            530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
            580                 585                 590
Thr Tyr His Asp Leu Leu Lys Ile Ile Lys Asp Lys Asp Phe Leu Asp
            595                 600                 605
Asn Glu Glu Asn Glu Asp Ile Leu Glu Asp Ile Val Leu Thr Leu Thr
610                 615                 620
Leu Phe Glu Asp Arg Glu Met Ile Glu Glu Arg Leu Lys Thr Tyr Ala
625                 630                 635                 640
His Leu Phe Asp Asp Lys Val Met Lys Gln Leu Lys Arg Arg Arg Tyr
                645                 650                 655
Thr Gly Trp Gly Arg Leu Ser Arg Lys Leu Ile Asn Gly Ile Arg Asp
            660                 665                 670
Lys Gln Ser Gly Lys Thr Ile Leu Asp Phe Leu Lys Ser Asp Gly Phe
                675                 680                 685
Ala Asn Arg Asn Phe Met Gln Leu Ile His Asp Asp Ser Leu Thr Phe
690                 695                 700
```

```
Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
        740                 745                 750

Arg His Lys Pro Glu Asn Ile Val Ile Glu Met Ala Arg Glu Asn Gln
                755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
        820                 825                 830

Leu Ser Asp Tyr Asp Val Asp His Ile Val Pro Gln Ser Phe Leu Lys
    835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
        900                 905                 910

Lys Ala Gly Phe Ile Lys Arg Gln Leu Val Glu Thr Arg Gln Ile Thr
    915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
        980                 985                 990

Val Gly Thr Ala Leu Ile Lys Lys Tyr Pro Lys Leu Glu Ser Glu Phe
    995                 1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
```

-continued

```
                    1115                1120                1125

Lys Lys Tyr Gly Gly Phe Asp Ser Pro Thr Val Ala Tyr Ser Val
            1130                1135                1140

Leu Val Val Ala Lys Val Glu Lys Gly Lys Ser Lys Lys Leu Lys
        1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
        1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
        1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
        1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
        1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
1355                1360                1365

<210> SEQ ID NO 2
<211> LENGTH: 1368
<212> TYPE: PRT
<213> ORGANISM: Artificial Sequence
<220> FEATURE:
<223> OTHER INFORMATION: Mutated Cas9 protein sequence

<400> SEQUENCE: 2

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
```

```
             100                 105                 110
His Glu Arg His Pro Ile Phe Gly Asn Ile Val Asp Glu Val Ala Tyr
             115                 120                 125
His Glu Lys Tyr Pro Thr Ile Tyr His Leu Arg Lys Leu Val Asp
         130                 135             140
Ser Thr Asp Lys Ala Asp Leu Arg Leu Ile Tyr Leu Ala Leu Ala His
145                 150                 155                 160
Met Ile Lys Phe Arg Gly His Phe Leu Ile Glu Gly Asp Leu Asn Pro
                 165                 170                 175
Asp Asn Ser Asp Val Asp Lys Leu Phe Ile Gln Leu Val Gln Thr Tyr
             180                 185                 190
Asn Gln Leu Phe Glu Glu Asn Pro Ile Asn Ala Ser Gly Val Asp Ala
         195                 200                 205
Lys Ala Ile Leu Ser Ala Arg Leu Ser Lys Ser Arg Arg Leu Glu Asn
     210                 215                 220
Leu Ile Ala Gln Leu Pro Gly Glu Lys Lys Asn Gly Leu Phe Gly Asn
225                 230                 235                 240
Gly Ile Ala Leu Ser Leu Gly Leu Thr Pro Asn Phe Lys Ser Asn Phe
                 245                 250                 255
Asp Leu Ala Glu Asp Ala Lys Leu Gln Leu Ser Lys Asp Thr Tyr Asp
             260                 265                 270
Asp Asp Leu Asp Asn Leu Leu Ala Gln Ile Gly Asp Gln Tyr Ala Asp
         275                 280                 285
Leu Phe Leu Ala Ala Lys Asn Leu Ser Asp Ala Ile Leu Leu Ser Asp
     290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                 325                 330                 335
Ala Leu Val Arg Gln Gln Leu Pro Glu Lys Tyr Lys Glu Ile Phe Phe
             340                 345                 350
Asp Gln Ser Lys Asn Gly Tyr Ala Gly Tyr Ile Asp Gly Gly Ala Ser
         355                 360                 365
Gln Glu Glu Phe Tyr Lys Phe Ile Lys Pro Ile Leu Glu Lys Met Asp
     370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                 405                 410                 415
Gly Glu Leu His Ala Ile Leu Arg Arg Gln Glu Asp Phe Tyr Pro Phe
             420                 425                 430
Leu Lys Asp Asn Arg Glu Lys Ile Glu Lys Ile Leu Thr Phe Arg Ile
         435                 440                 445
Pro Tyr Tyr Val Gly Pro Leu Ala Arg Gly Asn Ser Arg Phe Ala Trp
     450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                 485                 490                 495
Asn Phe Asp Lys Asn Leu Pro Asn Glu Lys Val Leu Pro Lys His Ser
             500                 505                 510
Leu Leu Tyr Glu Tyr Phe Thr Val Tyr Asn Glu Leu Thr Lys Val Lys
         515                 520                 525
```

```
Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
                580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
                660                 665                 670

Lys Gln Ser Gly Lys Thr Ile Leu Asp Phe Leu Lys Ser Asp Gly Phe
            675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
            755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
            835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
            915                 920                 925

Lys His Val Ala Gln Ile Leu Asp Ser Arg Met Asn Thr Lys Tyr Asp
930                 935                 940
```

```
Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
            995                1000                1005

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
```

```
            1340                1345                1350
Gly Leu Tyr Glu Thr Arg Ile Asp Leu Ser Gln Leu Gly Gly Asp
        1355                1360                1365

<210> SEQ ID NO 3
<211> LENGTH: 1368
<212> TYPE: PRT
<213> ORGANISM: Artificial Sequence
<220> FEATURE:
<223> OTHER INFORMATION: Mutated Cas9 protein sequence

<400> SEQUENCE: 3

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
```

```
            340             345             350
Asp Gln Ser Lys Asn Gly Tyr Ala Gly Tyr Ile Asp Gly Gly Ala Ser
            355             360             365
Gln Glu Glu Phe Tyr Lys Phe Ile Lys Pro Ile Leu Glu Lys Met Asp
            370             375             380
Gly Thr Glu Glu Leu Leu Val Lys Leu Asn Arg Glu Asp Leu Leu Arg
385             390             395             400
Lys Gln Arg Thr Phe Asp Asn Gly Ser Ile Pro His Gln Ile His Leu
                405             410             415
Gly Glu Leu His Ala Ile Leu Arg Arg Gln Glu Asp Phe Tyr Pro Phe
            420             425             430
Leu Lys Asp Asn Arg Glu Lys Ile Glu Lys Ile Leu Thr Phe Arg Ile
            435             440             445
Pro Tyr Tyr Val Gly Pro Leu Ala Arg Gly Asn Ser Arg Phe Ala Trp
            450             455             460
Met Thr Arg Lys Ser Glu Glu Thr Ile Thr Pro Trp Asn Phe Glu Glu
465             470             475             480
Val Val Asp Lys Gly Ala Ser Ala Gln Ser Phe Ile Glu Arg Met Thr
                485             490             495
Asn Phe Asp Lys Asn Leu Pro Asn Glu Lys Val Leu Pro Lys His Ser
            500             505             510
Leu Leu Tyr Glu Tyr Phe Thr Val Tyr Asn Glu Leu Thr Lys Val Lys
            515             520             525
Tyr Val Thr Glu Gly Met Arg Lys Pro Ala Phe Leu Ser Gly Glu Gln
            530             535             540
Lys Lys Ala Ile Val Asp Leu Leu Phe Lys Thr Asn Arg Lys Val Thr
545             550             555             560
Val Lys Gln Leu Lys Glu Asp Tyr Phe Lys Lys Ile Glu Cys Phe Asp
                565             570             575
Ser Val Glu Ile Ser Gly Val Glu Asp Arg Phe Asn Ala Ser Leu Gly
            580             585             590
Thr Tyr His Asp Leu Leu Lys Ile Ile Lys Asp Lys Asp Phe Leu Asp
            595             600             605
Asn Glu Glu Asn Glu Asp Ile Gly Glu Asp Ile Val Leu Thr Leu Thr
            610             615             620
Leu Phe Glu Asp Arg Glu Met Ile Glu Glu Arg Leu Lys Thr Tyr Ala
625             630             635             640
His Leu Phe Asp Asp Lys Val Met Lys Gln Leu Lys Arg Arg Arg Tyr
                645             650             655
Thr Gly Trp Gly Arg Leu Ser Arg Lys Leu Ile Asn Gly Ile Arg Asp
            660             665             670
Lys Gln Ser Gly Lys Thr Ile Leu Asp Phe Leu Lys Ser Asp Gly Phe
            675             680             685
Ala Asn Arg Asn Phe Met Gln Leu Ile His Asp Asp Ser Leu Thr Phe
            690             695             700
Lys Glu Asp Ile Gln Lys Ala Gln Val Ser Gly Gln Gly Asp Ser Leu
705             710             715             720
His Glu His Ile Ala Asn Leu Ala Gly Ser Pro Ala Ile Lys Lys Gly
                725             730             735
Ile Leu Gln Thr Val Lys Val Val Asp Glu Leu Val Lys Val Met Gly
            740             745             750
Arg His Lys Pro Glu Asn Ile Val Ile Glu Met Ala Arg Glu Asn Gln
            755             760             765
```

Thr Thr Gln Lys Gly Gln Lys Asn Ser Arg Glu Arg Met Lys Arg Ile
    770             775             780

Glu Glu Gly Ile Lys Glu Leu Gly Ser Gln Ile Leu Lys Glu His Pro
785             790             795             800

Val Glu Asn Thr Gln Leu Gln Asn Glu Lys Leu Tyr Leu Tyr Tyr Leu
            805             810             815

Gln Asn Gly Arg Asp Met Tyr Val Asp Gln Glu Leu Asp Ile Asn Arg
        820             825             830

Leu Ser Asp Tyr Asp Val Asp His Ile Val Pro Gln Ser Phe Leu Lys
    835             840             845

Asp Asp Ser Ile Asp Asn Lys Val Leu Thr Arg Ser Asp Lys Asn Arg
850             855             860

Gly Lys Ser Asp Asn Val Pro Ser Glu Val Val Lys Lys Met Lys
865             870             875             880

Asn Tyr Trp Arg Gln Leu Leu Asn Ala Lys Leu Ile Thr Gln Arg Lys
            885             890             895

Phe Asp Asn Leu Thr Lys Ala Glu Arg Gly Gly Leu Ser Glu Leu Asp
        900             905             910

Lys Ala Gly Phe Ile Lys Arg Gln Leu Val Glu Thr Arg Gln Ile Thr
    915             920             925

Lys His Val Ala Gln Ile Leu Asp Ser Arg Met Asn Thr Lys Tyr Asp
    930             935             940

Glu Asn Asp Lys Leu Ile Arg Glu Val Lys Val Ile Thr Leu Lys Ser
945             950             955             960

Lys Leu Val Ser Asp Phe Arg Lys Asp Phe Gln Phe Tyr Lys Val Arg
            965             970             975

Glu Ile Asn Asn Tyr His His Ala His Asp Ala Tyr Leu Asn Ala Val
        980             985             990

Val Gly Thr Ala Leu Ile Lys Lys Tyr Pro Lys Leu Glu Ser Glu Phe
    995             1000            1005

Val Tyr Gly Asp Tyr Lys Val Tyr Asp Val Arg Lys Met Ile Ala
    1010            1015            1020

Lys Ser Glu Gln Glu Ile Gly Lys Ala Thr Ala Lys Tyr Phe Phe
    1025            1030            1035

Tyr Ser Asn Ile Met Asn Phe Phe Lys Thr Glu Ile Thr Leu Ala
    1040            1045            1050

Asn Gly Glu Ile Arg Lys Arg Pro Leu Ile Glu Thr Asn Gly Glu
    1055            1060            1065

Thr Gly Glu Ile Val Trp Asp Lys Gly Arg Asp Phe Ala Thr Val
    1070            1075            1080

Arg Lys Val Leu Ser Met Pro Gln Val Asn Ile Val Lys Lys Thr
    1085            1090            1095

Glu Val Gln Thr Gly Gly Phe Ser Lys Glu Ser Ile Leu Pro Lys
    1100            1105            1110

Arg Asn Ser Asp Lys Leu Ile Ala Arg Lys Lys Asp Trp Asp Pro
    1115            1120            1125

Lys Lys Tyr Gly Gly Phe Asp Ser Pro Thr Val Ala Tyr Ser Val
    1130            1135            1140

Leu Val Val Ala Lys Val Glu Lys Gly Lys Ser Lys Lys Leu Lys
    1145            1150            1155

Ser Val Lys Glu Leu Leu Gly Ile Thr Ile Met Glu Arg Ser Ser
    1160            1165            1170

```
Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 4
<211> LENGTH: 1368
<212> TYPE: PRT
<213> ORGANISM: Artificial Sequence
<220> FEATURE:
<223> OTHER INFORMATION: Mutated Cas9 protein sequence

<400> SEQUENCE: 4

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160
```

-continued

```
Met Ile Lys Phe Arg Gly His Phe Leu Ile Glu Gly Asp Leu Asn Pro
                165                 170                 175
Asp Asn Ser Asp Val Asp Lys Leu Phe Ile Gln Leu Val Gln Thr Tyr
            180                 185                 190
Asn Gln Leu Phe Glu Glu Asn Pro Ile Asn Ala Ser Gly Val Asp Ala
        195                 200                 205
Lys Ala Ile Leu Ser Ala Arg Leu Ser Lys Ser Arg Arg Leu Glu Asn
    210                 215                 220
Leu Ile Ala Gln Leu Pro Gly Glu Lys Lys Asn Gly Leu Phe Gly Asn
225                 230                 235                 240
Gly Ile Ala Leu Ser Leu Gly Leu Thr Pro Asn Phe Lys Ser Asn Phe
                245                 250                 255
Asp Leu Ala Glu Asp Ala Lys Leu Gln Leu Ser Lys Asp Thr Tyr Asp
            260                 265                 270
Asp Asp Leu Asp Asn Leu Leu Ala Gln Ile Gly Asp Gln Tyr Ala Asp
        275                 280                 285
Leu Phe Leu Ala Ala Lys Asn Leu Ser Asp Ala Ile Leu Leu Ser Asp
    290                 295                 300
Ile Leu Arg Val Asn Thr Glu Ile Thr Lys Ala Pro Leu Ser Ala Ser
305                 310                 315                 320
Met Ile Lys Arg Tyr Asp Glu His His Gln Asp Leu Thr Leu Leu Lys
                325                 330                 335
Ala Leu Val Arg Gln Gln Leu Pro Glu Lys Tyr Lys Glu Ile Phe Phe
            340                 345                 350
Asp Gln Ser Lys Asn Gly Tyr Ala Gly Tyr Ile Asp Gly Gly Ala Ser
        355                 360                 365
Gln Glu Glu Phe Tyr Lys Phe Ile Lys Pro Ile Leu Glu Lys Met Asp
    370                 375                 380
Gly Thr Glu Glu Leu Leu Val Lys Leu Asn Arg Glu Asp Leu Leu Arg
385                 390                 395                 400
Lys Gln Arg Thr Phe Asp Asn Gly Ser Ile Pro His Gln Ile His Leu
                405                 410                 415
Gly Glu Leu His Ala Ile Leu Arg Arg Gln Glu Asp Phe Tyr Pro Phe
            420                 425                 430
Leu Lys Asp Asn Arg Glu Lys Ile Glu Lys Ile Leu Thr Phe Arg Ile
        435                 440                 445
Pro Tyr Tyr Val Gly Pro Leu Ala Arg Gly Asn Ser Arg Phe Ala Trp
    450                 455                 460
Met Thr Arg Lys Ser Glu Glu Thr Ile Thr Pro Trp Asn Phe Glu Glu
465                 470                 475                 480
Val Val Asp Lys Gly Ala Ser Ala Gln Ser Phe Ile Glu Arg Met Thr
                485                 490                 495
Asn Phe Asp Lys Asn Leu Pro Asn Glu Lys Val Leu Pro Lys His Ser
            500                 505                 510
Leu Leu Tyr Glu Tyr Phe Thr Val Tyr Asn Glu Leu Thr Lys Val Lys
        515                 520                 525
Tyr Val Thr Glu Gly Met Arg Lys Pro Ala Phe Leu Ser Gly Glu Gln
    530                 535                 540
Lys Lys Ala Ile Val Asp Leu Leu Phe Lys Thr Asn Arg Lys Val Thr
545                 550                 555                 560
Val Lys Gln Leu Lys Glu Asp Tyr Phe Lys Lys Ile Glu Cys Phe Asp
                565                 570                 575
Ser Val Glu Ile Ser Gly Val Glu Asp Arg Phe Asn Ala Ser Leu Gly
```

```
            580             585             590
Thr Tyr His Asp Leu Leu Lys Ile Ile Lys Asp Lys Asp Phe Leu Asp
            595             600             605

Asn Glu Glu Asn Glu Asp Ile Gly Glu Asp Ile Val Leu Thr Leu Thr
            610             615             620

Leu Phe Glu Asp Arg Glu Met Ile Glu Glu Arg Leu Lys Thr Tyr Ala
625             630             635             640

His Leu Phe Asp Asp Lys Val Met Lys Gln Leu Lys Arg Arg Arg Tyr
            645             650             655

Thr Gly Trp Gly Arg Leu Ser Arg Lys Leu Ile Asn Gly Ile Arg Asp
            660             665             670

Lys Gln Ser Gly Lys Thr Ile Leu Asp Phe Leu Lys Ser Asp Gly Phe
            675             680             685

Ala Asn Arg Asn Phe Met Gln Leu Ile His Asp Asp Ser Leu Thr Phe
            690             695             700

Lys Glu Asp Ile Gln Lys Ala Gln Val Ser Gly Gln Gly Asp Ser Leu
705             710             715             720

His Glu His Ile Ala Asn Leu Ala Gly Ser Pro Ala Ile Lys Lys Gly
            725             730             735

Ile Leu Gln Thr Val Lys Val Val Asp Glu Leu Val Lys Val Met Gly
            740             745             750

Arg His Lys Pro Glu Asn Ile Val Ile Glu Met Ala Arg Glu Asn Gln
            755             760             765

Thr Thr Gln Lys Gly Gln Lys Asn Ser Arg Glu Arg Met Lys Arg Ile
            770             775             780

Glu Glu Gly Ile Lys Glu Leu Gly Ser Gln Ile Leu Lys Glu His Pro
785             790             795             800

Val Glu Asn Thr Gln Leu Gln Asn Glu Lys Leu Tyr Leu Tyr Tyr Leu
            805             810             815

Gln Asn Gly Arg Asp Met Tyr Val Asp Gln Glu Leu Asp Ile Asn Arg
            820             825             830

Leu Ser Asp Tyr Asp Val Asp His Ile Val Pro Gln Ser Phe Leu Lys
            835             840             845

Asp Asp Ser Ile Asp Asn Lys Val Leu Thr Arg Ser Asp Lys Asn Arg
            850             855             860

Gly Lys Ser Asp Asn Val Pro Ser Glu Glu Val Val Lys Lys Met Lys
865             870             875             880

Asn Tyr Trp Arg Gln Leu Leu Asn Ala Lys Leu Ile Thr Gln Arg Lys
            885             890             895

Phe Asp Asn Leu Thr Lys Ala Glu Arg Gly Gly Leu Ser Glu Leu Asp
            900             905             910

Lys Ala Gly Phe Ile Lys Arg Gln Leu Val Glu Thr Arg Gln Ile Thr
            915             920             925

Lys His Val Ala Gln Ile Leu Asp Ser Arg Met Asn Thr Lys Tyr Asp
            930             935             940

Glu Asn Asp Lys Leu Ile Arg Glu Val Lys Val Ile Thr Leu Lys Ser
945             950             955             960

Lys Leu Val Ser Asp Phe Arg Lys Asp Phe Gln Phe Tyr Lys Val Arg
            965             970             975

Glu Ile Asn Asn Tyr His His Ala His Asp Ala Tyr Leu Asn Ala Val
            980             985             990

Val Gly Thr Ala Leu Ile Lys Lys  Tyr Pro Lys Leu Glu  Ser Glu Phe
            995             1000            1005
```

Val Tyr Gly Asp Tyr Lys Val Tyr Asp Val Arg Lys Met Ile Ala
    1010                1015                1020

Lys Ser Glu Gln Glu Ile Gly Lys Ala Thr Ala Lys Tyr Phe Phe
    1025                1030                1035

Tyr Ser Asn Ile Met Asn Phe Phe Lys Thr Glu Ile Thr Leu Ala
    1040                1045                1050

Asn Gly Glu Ile Arg Lys Arg Pro Leu Ile Glu Thr Asn Gly Glu
    1055                1060                1065

Thr Gly Glu Ile Val Trp Asp Lys Gly Arg Asp Phe Ala Thr Val
    1070                1075                1080

Arg Lys Val Leu Ser Met Pro Gln Val Asn Ile Val Lys Lys Thr
    1085                1090                1095

Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365

<210> SEQ ID NO 5
<211> LENGTH: 4107
<212> TYPE: DNA
<213> ORGANISM: Streptococcus pyogenes

<400> SEQUENCE: 5

```
atggataaga aatactcaat aggcttagat atcggcacaa atagcgtcgg atgggcggtg      60
atcactgatg aatataaggt tccgtctaaa aagttcaagg ttctgggaaa tacagaccgc     120
cacagtatca aaaaaaatct tatagggct cttttatttg acagtggaga dacagcggaa     180
gcgactcgtc tcaaacggac agctcgtaga aggtatacac gtcggaagaa tcgtatttgt     240
tatctacagg agattttttc aaatgagatg gcgaaagtag atgatagttt ctttcatcga     300
cttgaagagt ctttttttggt ggaagaagac aagaagcatg aacgtcatcc tatttttgga     360
aatatagtag atgaagttgc ttatcatgag aaatatccaa ctatctatca tctgcgaaaa     420
aaattggtag attctactga taaagcggat ttgcgcttaa tctatttggc cttagcgcat     480
atgattaagt ttcgtggtca ttttttgatt gagggagatt taaatcctga taatagtgat     540
gtggacaaac tatttatcca gttggtacaa acctacaatc aattatttga agaaaaccct     600
attaacgcaa gtggagtaga tgctaaagcg attctttctg cacgattgag taaatcaaga     660
cgattagaaa atctcattgc tcagctcccc ggtgagaaga aaaatggctt atttgggaat     720
ctcattgctt tgtcattggg tttgacccct aatttttaaat caaattttga tttggcagaa     780
gatgctaaat tacagctttc aaaagatact tacgatgatg atttagataa tttattggcg     840
caaattggag atcaatatgc tgatttgttt ttggcagcta agaatttatc agatgctatt     900
ttactttcag atatcctaag agtaaatact gaaataacta aggctcccct atcagcttca     960
atgattaaac gctacgatga acatcatcaa gacttgactc ttttaaaagc tttagttcga    1020
caacaacttc cagaaaagta taagaaaatc ttttttgatc aatcaaaaaa cggatatgca    1080
ggttatattg atgggggagc tagccaagaa gaattttata aatttatcaa accaattta    1140 gaaaaatgg atggtactga ggaattattg gtgaaactaa atcgtgaaga tttgctgcgc    1200
aagcaacgga cctttgacaa cggctctatt ccccatcaaa ttcacttggg tgagctgcat    1260
gctattttga aagacaagaa agacttttat ccatttttaa aagacaatcg tgagaagatt    1320
gaaaaaatct tgactttcg aattccttat tatgttggtc cattggcgcg tggcaatagt    1380
cgttttgcat ggatgactcg gaagtctgaa gaaacaatta ccccatggaa ttttgaagaa    1440
gttgtcgata aggtgcttc agctcaatca tttattgaac gcatgacaaa ctttgataaa    1500
aatcttccaa atgaaaaagt actaccaaaa catagtttgc tttatgagta ttttacggtt    1560
tataacgaat tgacaaaggt caaatatgtt actgaaggaa tgcgaaaacc agcatttctt    1620
tcaggtgaac agaagaaagc cattgttgat ttactcttca aaacaaatcg aaaagtaacc    1680
gttaagcaat taaagaaga ttatttcaaa aaaatagaat gttttgatag tgttgaaatt    1740
tcaggagttg aagatagatt taatgcttca ttaggtacct accatgattt gctaaaaatt    1800
attaaagata aagattttt ggataatgaa gaaaatgaag atatcttaga ggatatgtt    1860 ttaacattga ccttatttga agatagggag atgattgagg aaagacttaa acatatgct    1920 cacctctttg atgataaggt gatgaaacag cttaaacgtc gccgttatac tggttgggga    1980
cgtttgtctc gaaaattgat taatggtatt agggataagc aatctggcaa acaatatta    2040 gatttttga aatcagatgg ttttgccaat cgcaatttta tgcagctgat ccatgatgat    2100
agtttgacat ttaaagaaga cattcaaaaa gcacaagtgt ctggacaagg cgatagttta    2160
catgaacata ttgcaaattt agctggtagc cctgctatta aaaaggtat tttacagact    2220 gtaaaagttg ttgatgaatt ggtcaaagta atggggcggc ataagccaga aaatatcgtt    2280
attgaaatgg cacgtgaaaa tcagacaact caaaagggcc agaaaaattc gcgagagcgt    2340
```

```
atgaaacgaa tcgaagaagg tatcaaagaa ttaggaagtc agattcttaa agagcatcct    2400
gttgaaaata ctcaattgca aaatgaaaag ctctatctct attatctcca aaatggaaga    2460
gacatgtatg tggaccaaga attagatatt aatcgtttaa gtgattatga tgtcgatcac    2520
attgttccac aaagtttcct aaagacgat  tcaatagaca ataaggtctt aacgcgttct    2580
gataaaaatc gtggtaaatc ggataacgtt ccaagtgaag aagtagtcaa aagatgaaa     2640
aactattgga gacaacttct aaacgccaag ttaatcactc aacgtaagtt tgataattta    2700
acgaaagctg aacgtggagg tttgagtgaa cttgataaag ctggttttat caaacgccaa    2760
ttggttgaaa ctcgccaaat cactaagcat gtggcacaaa ttttggatag tcgcatgaat    2820
actaaatacg atgaaaatga taaacttatt cgagaggtta agtgattac  cttaaaatct    2880
aaattagttt ctgacttccg aaaagatttc caattctata agtacgtga  gattaacaat    2940
taccatcatg cccatgatgc gtatctaaat gccgtcgttg gaactgcttt gattaagaaa    3000
tatccaaaac ttgaatcgga gtttgtctat ggtgattata agtttatga  tgttcgtaaa    3060
atgattgcta agtctgagca agaaataggc aaagcaaccg caaatatttt cttttactct    3120
aatatcatga acttcttcaa aacagaaatt acacttgcaa atggagagat tcgcaaacgc    3180
cctctaatcg aaactaatgg ggaaactgga gaaattgtct gggataaagg gcgagatttt    3240
gccacagtgc gcaaagtatt gtccatgccc caagtcaata ttgtcaagaa aacagaagta    3300
cagacaggcg gattctccaa ggagtcaatt ttaccaaaaa gaaattcgga caagcttatt    3360
gctcgtaaaa aagactggga tccaaaaaaa tatggtggtt ttgatagtcc aacggtagct    3420
tattcagtcc tagtggttgc taaggtggaa aaagggaaat cgaagaagtt aaaatccgtt    3480
aaagagttac tagggatcac aattatgaaa agaagttcct ttgaaaaaaa tccgattgac    3540
ttttagaag  ctaaaggata taggaagtt  aaaaaagact taatcattaa actacctaaa    3600
tatagtcttt ttgagttaga aaacggtcgt aacggatgc  tggctagtgc cggagaatta    3660
caaaaaggaa atgagctggc tctgccaagc aaatatgtga  ttttttata tttagctagt    3720
cattatgaaa agttgaaggg tagtccagaa gataacgaac aaaaacaatt gtttgtggag    3780
cagcataagc attatttaga tgagattatt gagcaaatca gtgaatttc  taagcgtgtt    3840
atttagcag  atgccaattt agataaagtt cttagtgcat ataacaaaca tagagacaaa    3900
ccaatacgtg aacaagcaga aaatattatt catttattta cgttgacgaa tcttggagct    3960
cccgctgctt ttaaatattt tgatacaaca attgatcgta acgatatac  gtctacaaaa    4020
gaagttttag atgccactct tatccatcaa tccatcactg gtctttatga aacacgcatt    4080
gatttgagtc agctaggagg tgactga                                       4107
```

<210> SEQ ID NO 6
<211> LENGTH: 4272
<212> TYPE: DNA
<213> ORGANISM: Artificial Sequence
<220> FEATURE:
<223> OTHER INFORMATION: Cas9-Beta2

<400> SEQUENCE: 6

```
atggactata aggaccacga cggagactac aaggatcatg atattgatta caaagacgat      60
gacgataaga tggccccaaa gaagaagcgg aaggtcggta tccacggagt cccagcagcc     120
gacaagaagt acagcatcgg cctggacatc ggcaccaact ctgtgggctg gccgtgatc     180
accgacgagt acaaggtgcc cagcaagaaa ttcaaggtgc tgggcaacac cgaccggcac     240
```

```
agcatcaaga agaacctgat cggagccctg ctgttcgaca gcggcgaaac agccgaggcc    300
acccggctga agagaaccgc cagaagaaga tacaccagac ggaagaaccg gatctgctat    360
ctgcaagaga tcttcagcaa cgagatggcc aaggtggacg acagcttctt ccacagactg    420
gaagagtcct tcctggtgga agaggataag aagcacgagc ggcaccccat cttcggcaac    480
atcgtggacg aggtggccta ccacgagaag taccccacca tctaccacct gagaaagaaa    540 ctggtgggaca gcaccgacaa ggccgacctg cggctgatct atctggccct ggcccacatg    600
atcaagttcc ggggccactt cctgatcgag ggcgacctga accccgacaa cagcgacgtg    660
gacaagctgt tcatccagct ggtgcagacc tacaaccagc tgttcgagga aaacccccatc    720 aacgccagcg gcgtggacgc caaggccatc ctgtctgcca gactgagcaa gagcagacgg    780
ctggaaaatc tgatcgccca gctgcccggc gagaagaaga tggcctgtt cggaaacctt    840 attgccctga gcctgggcct gaccccccaac ttcaagagca cttcgacct ggccgaggat    900 gccaaactgc agctgagcaa ggacacctac gacgacgacc tggacaacct gctggcccag    960
atcggcgacc agtacgccga cctgtttctg gccgccaaga acctgtccga cgccatcctg   1020
ctgagcgaca tcctgagagt gaacaccgag atcaccaagg ccccccctgag cgcctctatg   1080 atcaagagat acgacgagca ccaccaggac ctgacctgc tgaaagctct cgtgcggcag   1140
cagctgcctg agaagtacaa agagattttc ttcgaccaga gcaagaacgg ctacgccggc   1200
tacattgacg gcgagccag ccaggaagag ttctacaagt catcaagcc catcctggaa   1260 aagatggacg gcaccgagga actgctcgtg aagctgaaca gagaggacct gctgcggaag   1320
cagcggacct tcgacaacgg cagcatcccc caccagatcc acctgggaga gctgcacgcc   1380
attctgcggc ggcaggaaga ttttttaccca ttcctgaagg acaaccggga aaagatcgag   1440
aagatcctga ccttccgcat cccctactac gtgggccctc tggccagggg aaacagcaga   1500
ttcgcctgga tgaccagaaa gagcgaggaa accatcaccc cctggaactt cgaggaagtg   1560
gtggacaagg gcgcttccgc ccagagcttc atcgagcgga tgaccaactt cgataagaac   1620
ctgcccaacg agaaggtgct gcccaagcac agcctgctgt acgagtactt caccgtgtat   1680
aacgagctga ccaaagtgaa atacgtgacc gagggaatga aaagcccgc cttcctgagc   1740 ggcgagcaga aaaaggccat cgtggacctg ctgttcaaga ccaaccggaa agtgaccgtg   1800
aagcagctga aagaggacta cttcaagaaa atcgagtgct tcgactccgt ggaaatctcc   1860
ggcgtggaag atcggttcaa cgcctccctg ggcacatacc acgatctgct gaaaattatc   1920
aaggacaagg acttcctgga caatgaggaa aacgaggaca ttggtgaaga tatcgtgctg   1980
accctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg gacaagcagt ccgcaagac aatcctggat   2160 ttcctgaagt ccgacggctt cgccaacaga aacttcatgc agctgatcca cgacgacagc   2220
ctgaccttta aagaggacat ccagaaagcc caggtgtccg ccagggcga tagcctgcac   2280 gagcacattg ccaatctggc cggcagcccc gccattaaga agggcatcct gcagacagtg   2340
aaggtggtgg acgagctcgt gaaagtgatg ggccggcaca agcccgagaa catcgtgatc   2400
gaaatggcca gagagaacca gaccacccag aagggacaga gaacagccg cgagagaatg   2460 aagcggatcg aagagggcat caaagagctg ggcagccaga tcctgaaaga acaccccgtg   2520
gaaaacaccc agctgcagaa cgagaagctg tacctgtact acctgcagaa tgggcggat   2580 atgtacgtgg accaggaact ggacatcaac cggctgtccg actacgatgt ggaccatatc   2640
```

```
gtgcctcaga gctttctgaa ggacgactcc atcgacaaca aggtgctgac cagaagcgac    2700
aagaaccggg gcaagagcga caacgtgccc tccgaagagg tcgtgaagaa gatgaagaac    2760
tactggcggc agctgctgaa cgccaagctg attacccaga gaaagttcga caatctgacc    2820
aaggccgaga gaggcggcct gagcgaactg gataaggccg gcttcatcaa gagacagctg    2880
gtggaaaccc ggcagatcac aaagcacgtg gcacagatcc tggactcccg gatgaacact    2940
aagtacgacg agaatgacaa gctgatccgg gaagtgaaag tgatcaccct gaagtccaag    3000
ctggtgtccg atttccggaa ggatttccag ttttacaaag tgcgcgagat caacaactac    3060
caccacgccc acgacgccta cctgaacgcc gtcgtgggaa ccgccctgat caaaaagtac    3120
cctaagctgg aaagcgagtt cgtgtacggc gactacaagg tgtacgacgt gcggaagatg    3180
atcgccaaga gcgagcagga aatcggcaag gctaccgcca gtacttcttc tacagcaac    3240 atcatgaact ttttcaagac cgagattacc ctggccaacg gcgagatccg gaagcggcct    3300
ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga cagcgataa gctgatcgcc    3480 agaaagaagg actgggaccc taagaagtac ggcggcttcg acagccccac cgtggcctat    3540
tctgtgctgg tggtggccaa agtggaaaag ggcaagtcca gaaactgaa gagtgtgaaa    3600 gagctgctgg ggatcaccat catggaaaga agcagcttcg agaagaatcc catcgacttt    3660
ctggaagcca agggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gccctccaaa tatgtgaact tcctgtacct ggccagccac    3840
tatgagaagc tgaagggctc ccccgaggat aatgagcaga acagctgtt tgtggaacag    3900 cacaagcact acctggacga gatcatcgag cagatcagcg agttctccaa gagagtgatc    3960
ctggccgacg ctaatctgga caaagtgctg tccgcctaca acaagcaccg ggataagccc    4020
atcagagagc aggccgagaa tatcatccac ctgtttaccc tgaccaatct gggagccccct    4080 gccgccttca gtactttga caccaccatc gaccggaaga ggtacaccag caccaaagag    4140
gtgctggacg ccaccctgat ccaccagagc atcaccggcc tgtacgagac acggatcgac    4200
ctgtctcagc tgggaggcga caaaaggccg gcggccacga aaaaggccgg ccaggcaaaa    4260
aagaaaaagt aa                                                       4272
```

<210> SEQ ID NO 7
<211> LENGTH: 4273
<212> TYPE: DNA
<213> ORGANISM: Artificial Sequence
<220> FEATURE:
<223> OTHER INFORMATION: Cas9-alpha2

<400> SEQUENCE: 7

```
atggactata aggaccacga cggagactac aaggatcatg atattgatta caaagacgat     60
gacgataaga tggcccccaa gaagaagcgg aaggtcggta ccacggagt cccagcagcc    120 gacaagaagt acagcatcgg cctggacatc ggcaccaact ctgtgggctg gccgtgatc    180 accgacgagt acaaggtgcc cagcaagaaa ttcaaggtgc tgggcaacac cgaccggcac    240
agcatcaaga gaacctgat cggagccctg ctgttcgaca cggcgaaaac agccgaggcc    300
acccggctga agagaaccgc cagaagaaga taccccgac ggaagaaccg gatctgctat    360
```

```
ctgcaagaga tcttcagcaa cgagatggcc aaggtggacg acagcttctt ccacagactg      420
gaagagtcct tcctggtgga agaggataag aagcacgagc ggcaccccat cttcggcaac      480
atcgtggacg aggtggccta ccacgagaag taccccacca tctaccacct gagaaagaaa      540
ctggtggaca gcaccgacaa ggccgacctg cggctgatct atctggccct ggcccacatg      600
atcaagttcc ggggccactt cctgatcgag ggcgacctga ccccgacaa cagcgacgtg      660 gacaagctgt tcatccagct ggtgcagacc tacaaccagc tgttcgagga aaaccccatc      720
aacgccagcg gcgtggacgc caaggccatc ctgtctgcca gactgagcaa gagcagacgg      780
ctggaaaatc tgatcgccca gctgcccggc gagaagaaga tggcctgtt cggaaacggt      840 attgccctga gcctgggcct gaccccccaac ttcaagagca acttcgacct ggccgaggat      900
gccaaactgc agctgagcaa ggacacctac gacgacgacc tggacaacct gctggcccag      960
atcggcgacc agtacgccga cctgtttctg gccgccaaga acctgtccga cgccatcctg     1020
ctgagcgaca tcctgagagt gaacaccgag atcaccaagg ccccctgag cgcctctatg      1080 atcaagagat acgacgagca ccaccaggac ctgaccctgc tgaaagctct cgtgcggcag     1140
cagctgcctg agaagtacaa agagattttc ttcgaccaga gcaagaacgg ctacgccggc     1200
tacattgacg gcggagccag ccaggaagag ttctacaagt tcatcaagcc catcctggaa     1260
aagatggacg gcaccgagga actgctcgtg aagctgaaca gagaggacct gctgcggaag     1320
cagcggacct cgacaacgg cagcatcccc caccagatcc acctgggaga gctgcacgcc     1380
attctgcggc ggcaggaaga ttttacccca ttcctgaagg acaaccggga aaagatcgag     1440
aagatcctga ccttccgcat ccctactac gtgggccctc tggccagggg aaacagcaga     1500
ttcgcctgga tgaccagaaa gagcgaggaa accatcaccc cctggaactt cgaggaagtg     1560
gtggacaagg gcgcttccgc ccagagcttc atcgagcgga tgaccaactt cgataagaac     1620
ctgcccaacg agaaggtgct gcccaagcac agcctgctgt acgagtactt caccgtgtat     1680
aacgagctga ccaaagtgaa atacgtgacc gagggaatga gaaagcccgc cttcctgagc     1740
ggcgagcaga aaaaggccat cgtggacctg ctgttcaaga ccaaccggaa agtgaccgtg     1800
aagcagctga aagaggacta cttcaagaaa atcgagtgct tcgactccgt ggaaatctcc     1860
ggcgtggaag atcggttcaa cgcctccctg ggcacatacc acgatctgct gaaaattatc     1920
aaggacaagg acttcctgga caatgaggaa acgaggaca ttcttgaaga tatcgtgctg     1980
accctgacac tgtttgagga cagagagatg atcgaggaac ggctgaaaac ctatgcccac     2040
ctgttcgacg acaaagtgat gaagcagctg aagcggcgga gatacaccgg ctggggcagg     2100
ctgagccgga agctgatcaa cggcatccgg gacaagcagt ccggcaagac aatcctggat     2160
ttcctgaagt ccgacggctt cgccaacaga aacttcatgc agctgatcca cgacgacagc     2220
ctgaccttta aagaggacat ccagaaagcc caggtgtccg gccagggcga tagcctgcac     2280
gagcacattg ccaatctggc cggcagcccc gccattaaga agggcatcct gcagacagtg     2340
aaggtggtgg acgagctcgt gaaagtgatg ggccggcaca gcccgagaa catcgtgatc     2400 gaaatggcca gagagaacca gaccacccag aagggacaga gaacagccg cgagagaatg     2460 aagcggatcg aagagggcat caaagagctg ggcagccaga tcctgaaaga acaccccgtg     2520
gaaaacaccc agctgcagaa cgagaagctg tacctgtact acctgcagaa tgggcgggat     2580
atgtacgtgg accaggaact ggacatcaac cggctgtccg actacgatgt ggaccatatc     2640
gtgcctcaga gctttctgaa ggacgactcc atcgacaaca aggtgctgac cagaagcgac     2700
aagaaccggg gcaagagcga caacgtgccc tccgaagagg tcgtgaagaa gatgaagaac     2760
```

```
tactggcggc agctgctgaa cgccaagctg attacccaga gaaagttcga caatctgacc    2820
aaggccgaga gaggcggcct gagcgaactg ataaggccg gcttcatcaa gagacagctg    2880
gtggaaaccc ggcagatcac aaagcacgtg gcacagatcc tggactcccg gatgaacact    2940
aagtacgacg agaatgacaa gctgatccgg gaagtgaaag tgatcaccct gaagtccaag    3000
ctggtgtccg atttccggaa ggatttccag ttttacaaag tgcgcgagat caacaactac    3060
caccacgccc acgacgccta cctgaacgcc gtcgtgggaa ccgccctgat caaaaagtac    3120
cctaagctgg aaagcgagtt cgtgtacggc gactacaagg tgtacgacgt gcggaagatg    3180
atcgccaaga gcgagcagga aatcggcaag gctaccgcca agtacttctt ctacagcaac    3240
atcatgaact tttcaagac cgagattacc ctggccaacg gcgagatccg gaagcggcct    3300
ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga cagcgataa gctgatcgcc    3480
agaaagaagg actgggaccc taagaagtac ggcggcttcg acagccccac cgtggcctat    3540
tctgtgctgg tggtggccaa agtggaaaag ggcaagtcca gaaaactgaa gagtgtgaaa    3600
gagctgctgg ggatcaccat catggaaaga agcagcttcg agaagaatcc catcgacttt    3660
ctggaagcca agggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gccctccaaa tatgtgaact tcctgtacct ggccagccac    3840
tatgagaagc tgaagggctc ccccgaggat aatgagcaga acagctgtt tgtggaacag    3900
cacaagcact acctggacga gatcatcgag cagatcagcg agttctccaa gagagtgatc    3960
ctggccgacg ctaatctgga caaagtgctg tccgcctaca caagcaccg gataagccc    4020
atcagagagc aggccgagaa tatcatccac ctgtttaccc tgaccaatct gggagccct    4080
gccgccttca gtactttga caccaccatc gaccggaaga ggtacaccag caccaaagag    4140
gtgctggacg ccaccctgat ccaccagagc atcaccggcc tgtacgagac acggatcgac    4200
ctgtctcagc tgggaggcga caaaaggccg gcggccacga aaaaggccgg ccaggcaaaa    4260
aagaaaaagt aag                                                       4273
```

<210> SEQ ID NO 8
<211> LENGTH: 4270
<212> TYPE: DNA
<213> ORGANISM: Artificial Sequence
<220> FEATURE:
<223> OTHER INFORMATION: Cas9-alpha2-beta2

<400> SEQUENCE: 8

```
atggactata aggaccacga cggagactac aaggatcatg atattgatta caaagacgat    60
gacgataaga tggcccccaa gaagaagcgg aaggtcggta tccacggagt cccagcagcc    120
gacaagaagt acagcatcgg cctggacatc ggcaccaact ctgtgggctg gccgtgatc    180
accgacgagt acaaggtgcc cagcaagaaa ttcaaggtgc tgggcaacac cgaccggcac    240
agcatcaaga gaacctgat cggagccctg ctgttcgaca cggcgaaac agccgaggcc    300
acccggctga gagaaccgc cagaagaaga tacaccagac ggaagaaccg gatctgctat    360
ctgcaagaga tcttcagcaa cgagatggcc aaggtggacg acagcttctt ccacagactg    420
gaagagtcct tcctggtgga agaggataag aagcacgagc ggcaccccat cttcggcaac    480
```

```
atcgtggacg aggtggccta ccacgagaag taccccacca tctaccacct gagaaagaaa    540
ctggtggaca gcaccgacaa ggccgacctg cggctgatct atctggccct ggcccacatg    600
atcaagttcc ggggccactt cctgatcgag ggcgacctga accccgacaa cagcgacgtg    660
gacaagctgt tcatccagct ggtgcagacc tacaaccagc tgttcgagga aaacccatc     720
aacgccagcg gcgtggacgc caaggccatc ctgtctgcca gactgagcaa gagcagacgg    780
ctggaaaatc tgatcgccca gctgcccggc gagaagaaga tggcctgtt cggaaacggt     840
attgccctga gcctgggcct gaccccaac ttcaagagca acttcgacct ggccgaggat     900
gccaaactgc agctgagcaa ggacacctac gacgacgacc tggacaacct gctggcccag    960
atcggcgacc agtacgccga cctgtttctg gccgccaaga acctgtccga cgccatcctg   1020
ctgagcgaca tcctgagagt gaacaccgag atcaccaagg ccccctgag cgcctctatg    1080
atcaagagat acgacgagca ccaccaggac ctgaccctgc tgaaagctct cgtgcggcag   1140
cagctgcctg agaagtacaa agagattttc ttcgaccaga gcaagaacgg ctacgccggc   1200
tacattgacg gcggagccag ccaggaagag ttctacaagt tcatcaagcc catcctggaa   1260
aagatggacg gcaccgagga actgctcgtg aagctgaaca gagaggacct gctgcggaag   1320
cagcggacct tcgacaacgg cagcatcccc caccagatcc acctgggaga gctgcacgcc   1380
attctgcggc ggcaggaaga tttttaccca ttcctgaagg acaaccggga aaagatcgag   1440
aagatcctga ccttccgcat ccctactac gtggccctc tggccagggg aaacagcaga    1500
ttcgcctgga tgaccagaaa gagcgaggaa accatcaccc cctggaactt cgaggaagtg   1560
gtggacaagg gcgcttccgc ccagagcttc atcgagcgga tgaccaactt cgataagaac   1620
ctgcccaacg agaaggtgct gcccaagcac agcctgctgt acgagtactt caccgtgtat   1680
aacgagctga ccaaagtgaa atacgtgacc gagggaatga gaaagcccgc cttcctgagc   1740
ggcgagcaga aaaaggccat cgtggacctg ctgttcaaga ccaaccggaa agtgaccgtg   1800
aagcagctga aagaggacta cttcaagaaa atcgagtgct tcgactccgt ggaaatctcc   1860
ggcgtggaag atcggttcaa cgcctccctg ggcacatacc acgatctgct gaaaattatc   1920
aaggacaagg acttcctgga caatgaggaa aacgaggaca ttggtgaaga tatcgtgctg   1980
accctgacac tgtttgagga cagagagatg atcgaggaac ggctgaaaac ctatgcccac   2040
ctgttcgacg acaaagtgat gaagcagctg aagcggcgga gatacaccgg ctggggcagg   2100
ctgagccgga agctgatcaa cggcatccgg gacaagcagt ccggcaagac aatcctggat   2160
ttcctgaagt ccgacggctt cgccaacaga aacttcatgc agctgatcca cgacgacagc   2220
ctgacctta aagaggacat ccagaaagcc caggtgtccg gccagggcga tagcctgcac   2280
gagcacattg ccaatctggc cggcagcccc gccattaaga agggcatcct gcagacagtg   2340
aaggtggtgg acgagctcgt gaaagtgatg ggccggcaca gcccgagaa catcgtgatc   2400
gaaatggcca gagagaacca gaccacccag aagggacaga gaacagccg cgagagaatg   2460
aagcggatcg aagagggcat caaagagctg ggcagccaga tcctgaaaga acaccccgtg   2520
gaaaacaccc agctgcagaa cgagaagctg tacctgtact acctgcagaa tgggcgggat   2580
atgtacgtgg accaggaact ggacatcaac cggctgtccg actacgatgt ggaccatatc   2640
gtgcctcaga gctttctgaa ggacgactcc atcgacaaca aggtgctgac cagaagcgac   2700
aagaaccggg gcaagagcga caacgtgccc tccgaagagg tcgtgaagaa gatgaagaac   2760
tactggcggc agctgctgaa cgccaagctg attcccaga gaaagttcga caatctgacc   2820
aaggccgaga gaggcggcct gagcgaactg gataaggccg gcttcatcaa gagacagctg   2880
```

-continued

```
gtggaaaccc ggcagatcac aaagcacgtg gcacagatcc tggactcccg gatgaacact    2940
aagtacgacg agaatgacaa gctgatccgg gaagtgaaag tgatcaccct gaagtccaag    3000
ctggtgtccg atttccggaa ggatttccag ttttacaaag tgcgcgagat caacaactac    3060
caccacgccc acgacgccta cctgaacgcc gtcgtgggaa ccgccctgat caaaaagtac    3120
cctaagctgg aaagcgagtt cgtgtacggc gactacaagg tgtacgacgt gcggaagatg    3180
atcgccaaga gcgagcagga aatcggcaag gctaccgcca agtacttctt ctacagcaac    3240
atcatgaact ttttcaagac cgagattacc ctggccaacg gcgagatccg gaagcggcct    3300
ctgatcgaga caaacggcga aaccggggag atcgtgtggg ataagggccg ggattttgcc    3360
accgtgcgga aagtgctgag catgccccaa gtgaatatcg tgaaaaagac cgaggtgcag    3420
acaggcggct tcagcaaaga gtctatcctg cccaagagga cagcgataa gctgatcgcc    3480 agaaagaagg actgggaccc taagaagtac ggcggcttcg acagccccac cgtggcctat    3540
tctgtgctgg tggtggccaa agtggaaaag ggcaagtcca agaaactgaa gagtgtgaaa    3600
gagctgctgg ggatcaccat catggaaaga agcagcttcg agaagaatcc catcgacttt    3660
ctggaagcca agggctacaa agaagtgaaa aaggacctga tcatcaagct gcctaagtac    3720
tccctgttcg agctggaaaa cggccggaag agaatgctgg cctctgccgg cgaactgcag    3780
aagggaaacg aactggccct gcccctccaaa tatgtgaact tcctgtacct ggccagccac    3840
tatgagaagc tgaagggctc ccccgaggat aatgagcaga acagctgtt tgtggaacag    3900 cacaagcact acctggacga gatcatcgag cagatcagcg agttctccaa gagagtgatc    3960
ctggccgacg ctaatctgga caaagtgctg tccgcctaca acaagcaccg ggataagccc    4020
atcagagagc aggccgagaa tatcatccac ctgtttaccc tgaccaatct gggagcccct    4080
gccgccttca gtactttga caccaccatc gaccggaaga ggtacaccag caccaaagag    4140
gtgctggacg ccaccctgat ccaccagagc atcaccggcc tgtacgagac acggatcgac    4200
ctgtctcagc tgggaggcga caaaaggccg gcggccacga aaaaggccgg ccaggcaaaa    4260
aagaaaaagt                                                           4270
```

<210> SEQ ID NO 9
<211> LENGTH: 14
<212> TYPE: DNA
<213> ORGANISM: Artificial Sequence
<220> FEATURE:
<223> OTHER INFORMATION: MIAT-14bp gRNA

<400> SEQUENCE: 9
gaggctgagc gcac                                                       14

<210> SEQ ID NO 10
<211> LENGTH: 14
<212> TYPE: DNA
<213> ORGANISM: Artificial Sequence
<220> FEATURE:
<223> OTHER INFORMATION: TTN-14bp gRNA

<400> SEQUENCE: 10
ggaagtctcc tttg                                                       14

<210> SEQ ID NO 11
<211> LENGTH: 20
<212> TYPE: DNA
<213> ORGANISM: Artificial Sequence
<220> FEATURE:

<223> OTHER INFORMATION: Reporter2-20bp gRNA

<400> SEQUENCE: 11
gtcccctcca ccccacagtg                                                    20

<210> SEQ ID NO 12
<211> LENGTH: 15
<212> TYPE: DNA
<213> ORGANISM: Artificial Sequence
<220> FEATURE:
<223> OTHER INFORMATION: CR10-14bp-gRNA

<400> SEQUENCE: 12
gcatcaggaa catgt                                                         15

<210> SEQ ID NO 13
<211> LENGTH: 24
<212> TYPE: DNA
<213> ORGANISM: Artificial Sequence
<220> FEATURE:
<223> OTHER INFORMATION: EMX1- 20bp gRNA

<400> SEQUENCE: 13
caccgagtcc gagcagaaga agaa                                               24

<210> SEQ ID NO 14
<211> LENGTH: 40
<212> TYPE: DNA
<213> ORGANISM: Artificial Sequence
<220> FEATURE:
<223> OTHER INFORMATION: Cas9 fragment1-FW

<400> SEQUENCE: 14
ttttggtctc taggtccacc atggactata aggaccacga                              40

<210> SEQ ID NO 15
<211> LENGTH: 33
<212> TYPE: DNA
<213> ORGANISM: Artificial Sequence
<220> FEATURE:
<223> OTHER INFORMATION: Cas9 fragment1-RV

<400> SEQUENCE: 15
tttggtctca gaacagctgg ttgtaggtct gca                                     33

<210> SEQ ID NO 16
<211> LENGTH: 35
<212> TYPE: DNA
<213> ORGANISM: Artificial Sequence
<220> FEATURE:
<223> OTHER INFORMATION: Cas9 fragment2-FW

<400> SEQUENCE: 16
ttttggtctc taccaaccgg aaagtgaccg tgaag                                   35

<210> SEQ ID NO 17
<211> LENGTH: 34
<212> TYPE: DNA
<213> ORGANISM: Artificial Sequence
<220> FEATURE:
<223> OTHER INFORMATION: Cas9 fragment2-RV

<400> SEQUENCE: 17
ttttggtctc aaagcttact ttttcttttt tgcc                                    34

```
<210> SEQ ID NO 18
<211> LENGTH: 20
<212> TYPE: DNA
<213> ORGANISM: Artificial Sequence
<220> FEATURE:
<223> OTHER INFORMATION: qPCRMIAT-FW

<400> SEQUENCE: 18
tggctggggt ttgaaccttt                                         20

<210> SEQ ID NO 19
<211> LENGTH: 20
<212> TYPE: DNA
<213> ORGANISM: Artificial Sequence
<220> FEATURE:
<223> OTHER INFORMATION: qPCR-MIAT RV

<400> SEQUENCE: 19
aggaagctgt tccagactgc                                         20

<210> SEQ ID NO 20
<211> LENGTH: 20
<212> TYPE: DNA
<213> ORGANISM: Artificial Sequence
<220> FEATURE:
<223> OTHER INFORMATION: qPCRTTN FW

<400> SEQUENCE: 20
tgttgccact ggtgctaaag                                         20

<210> SEQ ID NO 21
<211> LENGTH: 20
<212> TYPE: DNA
<213> ORGANISM: Artificial Sequence
<220> FEATURE:
<223> OTHER INFORMATION: qPCR-TTN-RV

<400> SEQUENCE: 21
acagcagtct tctccgcttc                                         20

<210> SEQ ID NO 22
<211> LENGTH: 20
<212> TYPE: DNA
<213> ORGANISM: Artificial Sequence
<220> FEATURE:
<223> OTHER INFORMATION: PCR-EMX1-FW

<400> SEQUENCE: 22 ccatccccctt ctgtgaatgt                                        20

<210> SEQ ID NO 23
<211> LENGTH: 20
<212> TYPE: DNA
<213> ORGANISM: Artificial Sequence
<220> FEATURE:
<223> OTHER INFORMATION: PCR-EMX1-RV

<400> SEQUENCE: 23
ggagattgga gacacggaga                                         20

<210> SEQ ID NO 24
<211> LENGTH: 10
<212> TYPE: PRT
<213> ORGANISM: Artificial Sequence
<220> FEATURE:
<223> OTHER INFORMATION: synthetic
```

```
<400> SEQUENCE: 24

Tyr Leu Asn Ala Val Val Gly Thr Ala Leu
1               5                   10

<210> SEQ ID NO 25
<211> LENGTH: 10
<212> TYPE: PRT
<213> ORGANISM: Artificial Sequence
<220> FEATURE:
<223> OTHER INFORMATION: synthetic

<400> SEQUENCE: 25

Ile Leu Ala Asp Ala Asn Leu Asp Lys Val
1               5                   10

<210> SEQ ID NO 26
<211> LENGTH: 9
<212> TYPE: PRT
<213> ORGANISM: Artificial Sequence
<220> FEATURE:
<223> OTHER INFORMATION: synthetic

<400> SEQUENCE: 26

Gly Leu Phe Gly Asn Leu Ile Ala Leu
1               5

<210> SEQ ID NO 27
<211> LENGTH: 9
<212> TYPE: PRT
<213> ORGANISM: Artificial Sequence
<220> FEATURE:
<223> OTHER INFORMATION: synthetic

<400> SEQUENCE: 27

Asn Leu Ile Ala Leu Ser Leu Gly Leu
1               5

<210> SEQ ID NO 28
<211> LENGTH: 9
<212> TYPE: PRT
<213> ORGANISM: Artificial Sequence
<220> FEATURE:
<223> OTHER INFORMATION: synthetic

<400> SEQUENCE: 28

Ile Leu Glu Asp Ile Val Leu Thr Leu
1               5

<210> SEQ ID NO 29
<211> LENGTH: 10
<212> TYPE: PRT
<213> ORGANISM: Artificial Sequence
<220> FEATURE:
<223> OTHER INFORMATION: synthetic

<400> SEQUENCE: 29

Asp Ile Leu Glu Asp Ile Val Leu Thr Leu
1               5                   10

<210> SEQ ID NO 30
<211> LENGTH: 9
<212> TYPE: PRT
<213> ORGANISM: Artificial Sequence
<220> FEATURE:
<223> OTHER INFORMATION: synthetic

<400> SEQUENCE: 30
```

```
Ser Leu His Glu His Ile Ala Asn Leu
1               5
```

<210> SEQ ID NO 31
<211> LENGTH: 9
<212> TYPE: PRT
<213> ORGANISM: Artificial Sequence
<220> FEATURE:
<223> OTHER INFORMATION: synthetic

<400> SEQUENCE: 31

```
His Leu Gly Glu Leu His Ala Ile Leu
1               5
```

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

```
Ile Leu Leu Ser Asp Ile Leu Arg Val
1               5
```

<210> SEQ ID NO 33
<211> LENGTH: 10
<212> TYPE: PRT
<213> ORGANISM: Artificial Sequence
<220> FEATURE:
<223> OTHER INFORMATION: synthetic

<400> SEQUENCE: 33

```
Val Leu Ser Met Pro Gln Val Asn Ile Val
1               5                   10
```

<210> SEQ ID NO 34
<211> LENGTH: 10
<212> TYPE: PRT
<213> ORGANISM: Artificial Sequence
<220> FEATURE:
<223> OTHER INFORMATION: synthetic

<400> SEQUENCE: 34

```
Ser Leu His Glu His Ile Ala Asn Leu Ala
1               5                   10
```

<210> SEQ ID NO 35
<211> LENGTH: 10
<212> TYPE: PRT
<213> ORGANISM: Artificial Sequence
<220> FEATURE:
<223> OTHER INFORMATION: synthetic

<400> SEQUENCE: 35

```
Leu Ile Ile Lys Leu Pro Lys Tyr Ser Leu
1               5                   10
```

<210> SEQ ID NO 36
<211> LENGTH: 10
<212> TYPE: PRT
<213> ORGANISM: Artificial Sequence
<220> FEATURE:
<223> OTHER INFORMATION: synthetic

<400> SEQUENCE: 36

```
Thr Leu Ile His Gln Ser Ile Thr Gly Leu
1               5                   10

<210> SEQ ID NO 37
<211> LENGTH: 10
<212> TYPE: PRT
<213> ORGANISM: Artificial Sequence
<220> FEATURE:
<223> OTHER INFORMATION: synthetic

<400> SEQUENCE: 37

Lys Leu Pro Lys Tyr Ser Leu Phe Glu Leu
1               5                   10

<210> SEQ ID NO 38
<211> LENGTH: 10
<212> TYPE: PRT
<213> ORGANISM: Artificial Sequence
<220> FEATURE:
<223> OTHER INFORMATION: synthetic

<400> SEQUENCE: 38

Asn Ile Met Asn Phe Phe Lys Thr Glu Ile
1               5                   10

<210> SEQ ID NO 39
<211> LENGTH: 9
<212> TYPE: PRT
<213> ORGANISM: Artificial Sequence
<220> FEATURE:
<223> OTHER INFORMATION: synthetic

<400> SEQUENCE: 39

Ser Leu Leu Tyr Glu Tyr Phe Thr Val
1               5

<210> SEQ ID NO 40
<211> LENGTH: 10
<212> TYPE: PRT
<213> ORGANISM: Artificial Sequence
<220> FEATURE:
<223> OTHER INFORMATION: synthetic

<400> SEQUENCE: 40

Ile Ile His Leu Phe Thr Leu Thr Asn Leu
1               5                   10

<210> SEQ ID NO 41
<211> LENGTH: 10
<212> TYPE: PRT
<213> ORGANISM: Artificial Sequence
<220> FEATURE:
<223> OTHER INFORMATION: synthetic

<400> SEQUENCE: 41

Arg Leu Ser Arg Lys Leu Ile Asn Gly Ile
1               5                   10

<210> SEQ ID NO 42
<211> LENGTH: 10
<212> TYPE: PRT
<213> ORGANISM: Artificial Sequence
<220> FEATURE:
<223> OTHER INFORMATION: synthetic

<400> SEQUENCE: 42

Ala Leu Pro Ser Lys Tyr Val Asn Phe Leu
```

```
<210> SEQ ID NO 43
<211> LENGTH: 9
<212> TYPE: PRT
<213> ORGANISM: Artificial Sequence
<220> FEATURE:
<223> OTHER INFORMATION: synthetic

<400> SEQUENCE: 43

Ala Leu Ile Lys Lys Tyr Pro Lys Leu
1               5

<210> SEQ ID NO 44
<211> LENGTH: 9
<212> TYPE: PRT
<213> ORGANISM: Artificial Sequence
<220> FEATURE:
<223> OTHER INFORMATION: synthetic

<400> SEQUENCE: 44

Arg Leu Glu Asn Leu Ile Ala Gln Leu
1               5

<210> SEQ ID NO 45
<211> LENGTH: 9
<212> TYPE: PRT
<213> ORGANISM: Artificial Sequence
<220> FEATURE:
<223> OTHER INFORMATION: synthetic

<400> SEQUENCE: 45

Tyr Leu Ala Ser His Tyr Glu Lys Leu
1               5

<210> SEQ ID NO 46
<211> LENGTH: 9
<212> TYPE: PRT
<213> ORGANISM: Artificial Sequence
<220> FEATURE:
<223> OTHER INFORMATION: synthetic

<400> SEQUENCE: 46

Tyr Leu Asp Glu Ile Ile Glu Gln Ile
1               5

<210> SEQ ID NO 47
<211> LENGTH: 9
<212> TYPE: PRT
<213> ORGANISM: Artificial Sequence
<220> FEATURE:
<223> OTHER INFORMATION: synthetic

<400> SEQUENCE: 47

Ile Met Asn Phe Phe Lys Thr Glu Ile
1               5

<210> SEQ ID NO 48
<211> LENGTH: 10
<212> TYPE: PRT
<213> ORGANISM: Artificial Sequence
<220> FEATURE:
<223> OTHER INFORMATION: synthetic

<400> SEQUENCE: 48

Tyr Leu Gln Asn Gly Arg Asp Met Tyr Val
1               5                   10
```

```
<210> SEQ ID NO 49
<211> LENGTH: 9
<212> TYPE: PRT
<213> ORGANISM: Artificial Sequence
<220> FEATURE:
<223> OTHER INFORMATION: synthetic

<400> SEQUENCE: 49

Arg Met Leu Ala Ser Ala Gly Glu Leu
1               5

<210> SEQ ID NO 50
<211> LENGTH: 10
<212> TYPE: PRT
<213> ORGANISM: Artificial Sequence
<220> FEATURE:
<223> OTHER INFORMATION: synthetic

<400> SEQUENCE: 50

Lys Met Ile Ala Lys Ser Glu Gln Glu Ile
1               5                   10

<210> SEQ ID NO 51
<211> LENGTH: 9
<212> TYPE: PRT
<213> ORGANISM: Artificial Sequence
<220> FEATURE:
<223> OTHER INFORMATION: synthetic

<400> SEQUENCE: 51

Ser Gln Ile Leu Lys Glu His Pro Val
1               5

<210> SEQ ID NO 52
<211> LENGTH: 9
<212> TYPE: PRT
<213> ORGANISM: Artificial Sequence
<220> FEATURE:
<223> OTHER INFORMATION: synthetic

<400> SEQUENCE: 52

Lys Val Val Asp Glu Leu Val Lys Val
1               5

<210> SEQ ID NO 53
<211> LENGTH: 10
<212> TYPE: PRT
<213> ORGANISM: Artificial Sequence
<220> FEATURE:
<223> OTHER INFORMATION: synthetic

<400> SEQUENCE: 53

Phe Leu Glu Ala Lys Gly Tyr Lys Glu Val
1               5                   10

<210> SEQ ID NO 54
<211> LENGTH: 10
<212> TYPE: PRT
<213> ORGANISM: Artificial Sequence
<220> FEATURE:
<223> OTHER INFORMATION: synthetic

<400> SEQUENCE: 54

His Met Ile Lys Phe Arg Gly His Phe Leu
1               5                   10
```

```
<210> SEQ ID NO 55
<211> LENGTH: 9
<212> TYPE: PRT
<213> ORGANISM: Artificial Sequence
<220> FEATURE:
<223> OTHER INFORMATION: synthetic

<400> SEQUENCE: 55

Leu Leu Phe Lys Thr Asn Arg Lys Val
1               5

<210> SEQ ID NO 56
<211> LENGTH: 9
<212> TYPE: PRT
<213> ORGANISM: Artificial Sequence
<220> FEATURE:
<223> OTHER INFORMATION: synthetic

<400> SEQUENCE: 56

Lys Leu Val Asp Ser Thr Asp Lys Ala
1               5

<210> SEQ ID NO 57
<211> LENGTH: 10
<212> TYPE: PRT
<213> ORGANISM: Artificial Sequence
<220> FEATURE:
<223> OTHER INFORMATION: synthetic

<400> SEQUENCE: 57

Thr Ile Thr Pro Trp Asn Phe Glu Glu Val
1               5                   10

<210> SEQ ID NO 58
<211> LENGTH: 10
<212> TYPE: PRT
<213> ORGANISM: Artificial Sequence
<220> FEATURE:
<223> OTHER INFORMATION: synthetic

<400> SEQUENCE: 58

Gln Leu Phe Glu Glu Asn Pro Ile Asn Ala
1               5                   10

<210> SEQ ID NO 59
<211> LENGTH: 10
<212> TYPE: PRT
<213> ORGANISM: Artificial Sequence
<220> FEATURE:
<223> OTHER INFORMATION: synthetic

<400> SEQUENCE: 59

Phe Thr Val Tyr Asn Glu Leu Thr Lys Val
1               5                   10

<210> SEQ ID NO 60
<211> LENGTH: 9
<212> TYPE: PRT
<213> ORGANISM: Artificial Sequence
<220> FEATURE:
<223> OTHER INFORMATION: synthetic

<400> SEQUENCE: 60

Ile Thr Pro Trp Asn Phe Glu Glu Val
1               5
```

```
<210> SEQ ID NO 61
<211> LENGTH: 9
<212> TYPE: PRT
<213> ORGANISM: Artificial Sequence
<220> FEATURE:
<223> OTHER INFORMATION: synthetic

<400> SEQUENCE: 61

Phe Gln Phe Tyr Lys Val Arg Glu Ile
1               5

<210> SEQ ID NO 62
<211> LENGTH: 9
<212> TYPE: PRT
<213> ORGANISM: Artificial Sequence
<220> FEATURE:
<223> OTHER INFORMATION: synthetic

<400> SEQUENCE: 62

Asn Leu Ile Ala Phe Ser Leu Gly Leu
1               5

<210> SEQ ID NO 63
<211> LENGTH: 9
<212> TYPE: PRT
<213> ORGANISM: Artificial Sequence
<220> FEATURE:
<223> OTHER INFORMATION: synthetic

<400> SEQUENCE: 63

Asn Leu Ile Ser Leu Ser Leu Gly Leu
1               5

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Asn Leu Ile Ala Leu Ala Leu Gly Leu
1               5

<210> SEQ ID NO 65
<211> LENGTH: 9
<212> TYPE: PRT
<213> ORGANISM: Artificial Sequence
<220> FEATURE:
<223> OTHER INFORMATION: synthetic

<400> SEQUENCE: 65

Asp Leu Ile Ala Leu Tyr Leu Gly Leu
1               5

<210> SEQ ID NO 66
<211> LENGTH: 9
<212> TYPE: PRT
<213> ORGANISM: Artificial Sequence
<220> FEATURE:
<223> OTHER INFORMATION: synthetic

<400> SEQUENCE: 66

Asn Leu Leu Ala Leu Ala Leu Gly Leu
1               5

<210> SEQ ID NO 67
```

```
<211> LENGTH: 9
<212> TYPE: PRT
<213> ORGANISM: Artificial Sequence
<220> FEATURE:
<223> OTHER INFORMATION: synthetic

<400> SEQUENCE: 67

Asn Leu Ile Gly Leu Ala Leu Gly Leu
1               5

<210> SEQ ID NO 68
<211> LENGTH: 9
<212> TYPE: PRT
<213> ORGANISM: Artificial Sequence
<220> FEATURE:
<223> OTHER INFORMATION: synthetic

<400> SEQUENCE: 68

Asn Leu Val Ala Leu Ala Leu Gly Leu
1               5

<210> SEQ ID NO 69
<211> LENGTH: 9
<212> TYPE: PRT
<213> ORGANISM: Artificial Sequence
<220> FEATURE:
<223> OTHER INFORMATION: synthetic

<400> SEQUENCE: 69

Asn Leu Val Ala Leu Val Leu Gly Leu
1               5

<210> SEQ ID NO 70
<211> LENGTH: 9
<212> TYPE: PRT
<213> ORGANISM: Artificial Sequence
<220> FEATURE:
<223> OTHER INFORMATION: synthetic

<400> SEQUENCE: 70

Ser Leu Ile Ala Phe Ser Leu Gly Leu
1               5

<210> SEQ ID NO 71
<211> LENGTH: 9
<212> TYPE: PRT
<213> ORGANISM: Artificial Sequence
<220> FEATURE:
<223> OTHER INFORMATION: synthetic

<400> SEQUENCE: 71

Tyr Leu Ile Ala Leu Ala Leu Gly Leu
1               5

<210> SEQ ID NO 72
<211> LENGTH: 9
<212> TYPE: PRT
<213> ORGANISM: Artificial Sequence
<220> FEATURE:
<223> OTHER INFORMATION: synthetic

<400> SEQUENCE: 72

Ile Leu Glu Gly Ile Val Leu Thr Leu
1               5

<210> SEQ ID NO 73
<211> LENGTH: 9
```

```
<212> TYPE: PRT
<213> ORGANISM: Artificial Sequence
<220> FEATURE:
<223> OTHER INFORMATION: synthetic

<400> SEQUENCE: 73

Ile Leu Glu Asp Ile Val Gln Thr Leu
1               5

<210> SEQ ID NO 74
<211> LENGTH: 9
<212> TYPE: PRT
<213> ORGANISM: Artificial Sequence
<220> FEATURE:
<223> OTHER INFORMATION: synthetic

<400> SEQUENCE: 74

Val Leu Glu Asp Ile Val Leu Thr Leu
1               5

<210> SEQ ID NO 75
<211> LENGTH: 9
<212> TYPE: PRT
<213> ORGANISM: Artificial Sequence
<220> FEATURE:
<223> OTHER INFORMATION: synthetic

<400> SEQUENCE: 75

Val Leu Glu Asp Ile Val Leu Ser Leu
1               5

<210> SEQ ID NO 76
<211> LENGTH: 9
<212> TYPE: PRT
<213> ORGANISM: Artificial Sequence
<220> FEATURE:
<223> OTHER INFORMATION: synthetic

<400> SEQUENCE: 76

Ile Leu Glu Asn Ile Val His Thr Leu
1               5

<210> SEQ ID NO 77
<211> LENGTH: 9
<212> TYPE: PRT
<213> ORGANISM: Artificial Sequence
<220> FEATURE:
<223> OTHER INFORMATION: synthetic

<400> SEQUENCE: 77

Asn Gly Ile Ala Leu Ser Leu Gly Leu
1               5

<210> SEQ ID NO 78
<211> LENGTH: 9
<212> TYPE: PRT
<213> ORGANISM: Artificial Sequence
<220> FEATURE:
<223> OTHER INFORMATION: synthetic

<400> SEQUENCE: 78

Asn Leu Ile Ala Leu Ser Leu Gly Gly
1               5

<210> SEQ ID NO 79
<211> LENGTH: 9
<212> TYPE: PRT
```

```
<213> ORGANISM: Artificial Sequence
<220> FEATURE:
<223> OTHER INFORMATION: synthetic

<400> SEQUENCE: 79

Asn Gly Ile Ala Leu Ser Leu Gly Gly
1               5

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Ile Gly Glu Asp Ile Val Leu Thr Leu
1               5

<210> SEQ ID NO 81
<211> LENGTH: 9
<212> TYPE: PRT
<213> ORGANISM: Artificial Sequence
<220> FEATURE:
<223> OTHER INFORMATION: synthetic

<400> SEQUENCE: 81

Ile Leu Glu Asp Ile Val Leu Thr Gly
1               5

<210> SEQ ID NO 82
<211> LENGTH: 9
<212> TYPE: PRT
<213> ORGANISM: Artificial Sequence
<220> FEATURE:
<223> OTHER INFORMATION: synthetic

<400> SEQUENCE: 82

Ile Gly Glu Asp Ile Val Leu Thr Gly
1               5
```